(12) United States Patent
Baselga et al.

(10) Patent No.: US 11,248,229 B2
(45) Date of Patent: Feb. 15, 2022

(54) INHIBITION OF KMT2D FOR THE TREATMENT OF CANCER

(71) Applicant: MEMORIAL SLOAN-KETTERING CANCER CENTER, New York, NY (US)

(72) Inventors: Jose Baselga, New York, NY (US); Eneda Toska, Edgewater, NJ (US); Scott Armstrong, Wayland, MA (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/409,446

(22) Filed: May 10, 2019

(65) Prior Publication Data

US 2019/0270997 A1 Sep. 5, 2019

Related U.S. Application Data

(63) Continuation of application No. PCT/US2017/061073, filed on Nov. 10, 2017.

(60) Provisional application No. 62/420,324, filed on Nov. 10, 2016.

(51) Int. Cl.
| | |
|---|---|
| C12N 15/113 | (2010.01) |
| A61P 35/00 | (2006.01) |
| A61K 31/713 | (2006.01) |
| A61K 45/06 | (2006.01) |
| A61K 31/4439 | (2006.01) |
| A61K 31/454 | (2006.01) |

(52) U.S. Cl.
CPC ...... *C12N 15/1137* (2013.01); *A61K 31/4439* (2013.01); *A61K 31/454* (2013.01); *A61K 31/713* (2013.01); *A61K 45/06* (2013.01); *A61P 35/00* (2018.01); *C12N 2310/122* (2013.01); *C12N 2320/31* (2013.01)

(58) Field of Classification Search
None
See application file for complete search history.

(56) References Cited

U.S. PATENT DOCUMENTS

| 6,506,559 B1 | 1/2003 | Fire et al. | |
|---|---|---|---|
| 6,573,099 B2 | 6/2003 | Graham | |
| 2014/0377258 A1 | 12/2014 | Stern et al. | |
| 2015/0352076 A1* | 12/2015 | Sakai | A61K 31/5377 514/232.2 |
| 2016/0303134 A1 | 10/2016 | Liu et al. | |
| 2016/0339035 A1* | 11/2016 | Berger | A61K 31/136 |

FOREIGN PATENT DOCUMENTS

| WO | WO 1999/032619 A1 | 7/1999 |
|---|---|---|
| WO | WO 2001/036646 A1 | 5/2001 |
| WO | WO 2001/068836 A2 | 9/2001 |
| WO | WO 2012/052745 A1 | 4/2012 |
| WO | WO 2013/049581 A1 | 4/2013 |
| WO | WO 2015/108940 A2 | 7/2015 |
| WO | WO 2016/073956 A1 | 5/2016 |

OTHER PUBLICATIONS

Andre et al., "SOLAR-1: A phase III study of alpelisib + fulvestrant in men and postmenopausal women with HR+/HER2—advanced breast cancer (BC) progressing on or after prior aromatase inhibitor therapy," J Clin Oncol 34 (2016).
Baselga et al., "SANDPIPER: Phase III study of the PI3-kinase (PI3K) inhibitor taselisib (GDC-0032) plus fulvestrant in patients (pts) with estrogen receptor (ER)-positive, HER2-negative locally advanced or metastatic breast cancer (BC) enriched for pts with PIK3CA-mutant tumors," J Clin Oncol 34 (2016).
Bolger et al., "Trimmomatic: a flexible trimmer for Illumina sequence data," Bioinformatics 30, 2114-2120, doi:10.1093/bioinformatics/btu170 (2014).
Bosch et al., "PI3K inhibition results in enhanced estrogen receptor function and dependence in hormone receptor-positive breast cancer," Science translational medicine 7, 283ra251, doi:10.1126/scitranslmed.aaa4442 (2015).
Brummelkamp et al. "Stable suppression of tumorigenicity by virus-mediated RNA interference," Cancer Cell vol. 2 pp. 243-247 (2002).
Buenrostro et al., "Transposition of native chromatin for multimodal regulatory analysis and personal epigenomics," Nature methods 10, 1213-1218, doi:10.1038/nmeth.2688 (2013).
Cancer Genome Atlas Network, "Comprehensive molecular portraits of human breast tumors," Nature 490, 61-70, doi:10.1038/nature11412 (2012).
Cantley et al., "The phosphoinositide 3-kinase pathway," Science 296, 1655-1657, doi:10.1126/science.296.5573.1655 (2002).
Cha et al., "Akt-mediated phosphorylation of EZH2 suppresses methylation of lysine 27 in histone H3," Science 310, 306-310, doi:10.1126/science.1118947 (2005).
Cheon et al., "Identification of KMT2D and KDM6A mutations by exome sequencing in Korean patients with Kabuki syndrome," J. Hum. Genet. 59 (6):321-5 (2014).
Ciriello et al., "Comprehensive Molecular Portraits of Invasive Lobular Breast Cancer," Cell 163, 506-519, doi:10.1016/j.cell.2015.09.033 (2015).
Costa et al., "Measurement of PIP3 levels reveals an unexpected role for p110beta in early adaptive responses to p110alpha-specific inhibitors in luminal breast cancer," Cancer cell 27, 97-108, doi:10.1016/j.ccell.2014.11.007 (2015).

(Continued)

*Primary Examiner* — Sean McGarry
(74) *Attorney, Agent, or Firm* — Baker Botts L.L.P.

(57) ABSTRACT

The presently disclosed subject matter relates to the administration of a KMT2D inhibitor for the treatment of a cancer. The present invention is based on the discovery that upon PI3K inhibition, KMT2D activity is upregulated, resulting in an increase in the expression of genes involved in breast cancer cell proliferation and tumor growth. Accordingly, the present invention provides methods for treating a subject that has cancer by administering a therapeutically effective amount of an KMT2D inhibitor.

8 Claims, 35 Drawing Sheets

Figure 1B:
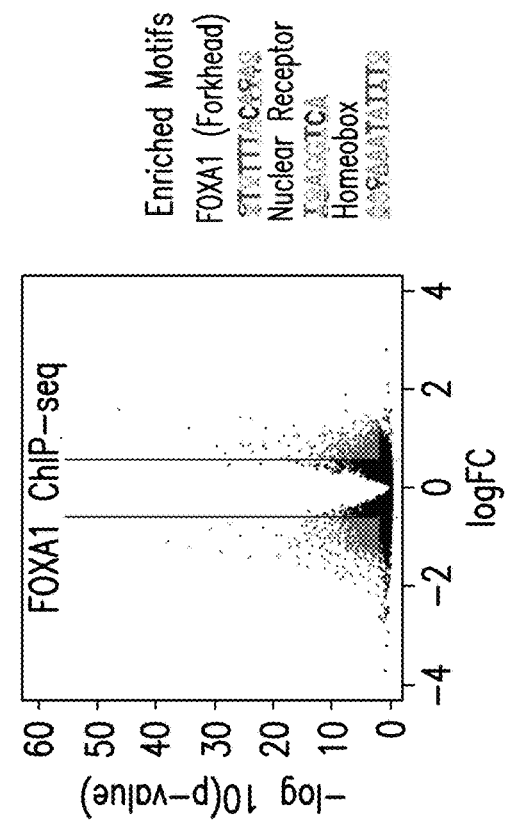

Specification includes a Sequence Listing.

(56) References Cited

OTHER PUBLICATIONS

Eeckhoute et al., "Cell-type selective chromatin remodeling defines the active subset of FOXA1-bound enhancers," Genome research 19, 372-380, doi:10.1101/gr.084582.108 (2009).
Engelman, "Targeting PI3K signaling in cancer: opportunities, challenges and limitations," Nature reviews. Cancer 9, 550-562, doi:10.1038/nrc2664 (2009).
Erdjument-Bromage et al., "Examination of micro-tip reversed-phase liquid chromatographic extraction of peptide pools for mass spectrometric analysis," Journal of chromatography, A 826, 167-181 (1998).
Fritsch et al., "Characterization of the novel and specific PI3Kalpha inhibitor NVP-BYL719 and development of the patient stratification strategy for clinical trials," Molecular cancer therapeutics 13, 1117-1129, doi:10.1158/1535-7163.MCT-13-0865 (2014).
Gentleman et al., "Bioconductor: open software development for computational biology and bioinformatics," Genome Biol 5, R80, doi:10.1186/gb-2004-5-10-r80 (2004).
Green et al., "Oestrogen-receptor-mediated transcription and the influence of co-factors and chromatin state," Nature reviews. Cancer 7, 713-722, doi:10.1038/nrc2211 (2007).
Guo et al., "KMT2D maintains neoplastic cell proliferation and global histone H3 lysine 4 monomethylation,"Oncotarget 4(11): 2144-2153 (2013).
Hannon, "RNA interference," Nature vol. 418 pp. 244-251 (2002).
Hayakawa et al., "Synthesis and biological evaluation of sulfonylhydrazone-substituted imidazo[1,2-a]pyridines as novel PI3 kinase p110alpha inhibitors," Bioorg. Med. Chem. 15(17):5837-5844, (2007).
Heinz et al., "Simple combinations of lineage-determining transcription factors prime cis-regulatory elements required for macrophage and B cell identities," Mol Cell 38, 576-589, doi:10.1016/j.molcel.2010.05.004 (2010).
Herz et al., "Enhancer-associated H3K4 monomethylation by Trithorax-related, the *Drosophila homolog* of mammalian Mll3/Mll4," Genes & development 26, 2604-2620, doi:10.1101/gad.201327.112 (2012).
Herz et al., "Enhancer Malfunction in Cancer," Molecular Cell 53, 859-866, doi:10.1016/j.molcel.2014.02.033 (2014).
Hu et al., "The MLL3/MLL4 branches of the COMPASS family function as major histone H3K4 monomethylases at enhancers," Molecular and cellular biology 33, 4745-4754, doi:10.1128/MCB.01181-13 (2013).
Hurtado et al., "FOXA1 is a key determinant of estrogen receptor function and endocrine response," Nature genetics 43, 27-33, doi:10.1038/ng.730 (2011).
ISR for International Patent Application No. PCT/US2017/061073 dated Feb. 20, 2018.
Janku, F. et al. Phase I study of the PI3Kα inhibitor BYL719 plus fulvestrant in patients with PIK3CA-altered and wild type ER+/HER2—locally advanced or metastatic breast cancer. Cancer research 75, PD5-5-PD5-5, doi:10.1158/1538-7445.sabcs14-pd5-5 (2015).
Je et al., "Mutational and expressional analysis of MLL genes in gastric and colorectal cancers with microsatellite instability," Neoplasma 60(2):188-95 (2013).
Juric et al., "Abstract CT-01: BYL719, a next generation PI3K alpha specific inhibitor: Preliminary safety, PK, and efficacy results from the first-in-human study," Cancer research 72, CT-01-CT-01 (2012).
Juric et al., Abstract LB-64: GDC-0032, a beta isoform-sparing PI3K inhibitor: Results of a first-in-human phase Ia dose escalation study, Cancer research 73, LB-64-LB-64 (2013).
Juric et al., "Ph1b study of the PI3K inhibitor GDC-0032 in combination with fulvestrant in patients with hormone receptor-positive advanced breast cancer," Cancer research 73, doi:10.1158/0008-5472.SABCS13-PD1-3 (2013).
Juric et al., "Convergent loss of PTEN leads to clinical resistance to a PI3Kalpha inhibitor," Nature 518, 240-244, doi:10.1038/nature13948 (2015).
Kantidakis et al., "Mutation of cancer driver MLL2 results in transcription stress and genome instability," Genes & Dev. 30:408-420 (2016).
Kim et al. "UTX and MLL4 Coordinately Regulate Transcriptional Programs for Cell Proliferation and Invasiveness in Breast Cancer Cells," Cancer Research, vol. 74, pp. 1705-1717 (2014).
Kooistra et al., "Molecular mechanisms and potential functions of histone demethylases," Nature reviews. Molecular cell biology 13, 297-311, doi:10.1038/nrm3327 (2012).
Langmead et al., "Ultrafast and memory-efficient alignment of short DNA sequences to the human genome," Genome Biol 10, R25, doi:10.1186/gb-2009-10-3-r25 (2009).
Li et al., "Measuring reproducibility of high-throughput experiments," The Annals of Applied Statistics 5, 1752-1779 (2011).
Lupien et al., "FoxA1 translates epigenetic signatures into enhancer-driven lineage-specific transcription," Cell 132, 958-970, doi:10.1016/j.cell.2008.01.018 (2008).
Magnani et al., "PBX1 Genomic Pioneer Function Drives ERalpha Signaling Underlying Progression in Breast Cancer," PLoS genetics 7, e1002368, doi:10.1371/journal.pgen.1002368 (2011).
Manning et al., "AKT/PKB Signaling: Navigating Downstream," Cell 129, 1261-1274, doi:10.1016/j.cell.2007.06.009 (2007).
Mayer et al., "A Phase Ib Study of Alpelisib (BYL719), a PI3Kalpha-Specific Inhibitor, with Letrozole in ER+/HER2-Negative Metastatic Breast Cancer," Clinical cancer research: an official journal of the American Association for Cancer Research, doi:10.1158/1078-0432.CCR-16-0134 (2016).
Micale et al., "Mutation spectrum of MLL2 in a cohort of kabuki syndrome patients," Orphanet Journal of Rare Diseases. 6:38-45 (2011).
Mo et al., "Identification of the MLL2 Complex as a Coactivator for Estrogen Eeceptor alpha," The Journal of biological chemistry 281, 15714-15720, doi:10.1074/jbc.M513245200 (2006).
Natarajan et al., "Epigenetic regulator MLL2 shows altered expression in cancer cell lines and tumors from human breast and colon," Cancer Cell Int. 10:13 (2010).
Pearce et al., "The nuts and bolts of AGC protein kinases," Nature reviews. Molecular cell biology 11, 9-22, doi:10.1038/nrm2822 (2010).
Ramirez et al., "deepTools: a flexible platform for exploring deep-sequencing data," Nucleic Acids Res 42, W187-191, doi:10.1093/nar/gku365 (2014).
Reagan-Shaw et al., "Dose translation from animal to human studies revisited," The FASEB J., vol. 22: 659-661 (2008).
Robinson et al., "edgeR: a Bioconductor package for differential expression analysis of digital gene expression data," Bioinformatics 26, 139-140, doi:10.1093/bioinformatics/btp616 (2010).
Sandoval et al., "Going Beyond Genetics to Discover Cancer Targets," Genome Biology, vol. 18, No. 95, pp. 1-3 (2017).
Shilatifard, "The COMPASS Family of Histone H3K4 Methylases: Mechanisms of Regulation in Development and Disease Pathogenesis," Annual review of biochemistry 81, 65-95, doi:10.1146/annurev-biochem-051710-134100 (2012).
Spangle et al., "PI3K/AKT Signaling Regulates H3K4 Methylation in Breast Cancer," Cell reports 15, 2692-2704, doi:10.1016/j.celrep.2016.05.046 (2016).
Thorpe et al., "PI3K in cancer: divergent roles of isoforms, modes of activation and therapeutic targeting," Nature reviews. Cancer 15, 7-24, doi:10.1038/nrc3860 (2015).
Toska et al., "PI3K Pathway Regulates ER-Dependent Transcription in Breast Cancer Through the Epigenetic Regulator KMT2D," Science, vol. 355, pp. 1324-1330 (2017).
Tuschl et al., "Targeted MRNA degradation by double-stranded RNA in vitro," Genes & Development, pp. 3191-3197 (1999).
Winter et al., "Selective Target Protein Degradation via Phthalimide Conjugation," Science, vol. 348, pp. 1376-1381 (2015).
Zhang et al., Model-based analysis of ChIP-Seq (MACS), Genome Biol 9, R137, doi:10.1186/gb-2008-9-9-r137 (2008).
Zhu et al., "ChIPpeakAnno: a Bioconductor package to annotate ChIP-seq and ChIP-chip data," BMC Bioinformatics 11, 237, doi:10.1186/1471-2105-11-237 (2010).

(56) References Cited

OTHER PUBLICATIONS

Ye et al., "MLL2 protein is a prognostic marker for gastrointestinal diffuse large B-cell lymphoma," Int. J. Clin. Exp. Pathol. 8(10):13043-13050 (2015).
Supplementary European Search Report dated May 25, 2020 corresponding to European Patent Application No. EP 17869265.
Koren et al., "Tackling Resistance to PI3K Inhibition by Targeting the Epigenome," Cancer Cell, 31, 616-618, XP085004711 (2016).

* cited by examiner

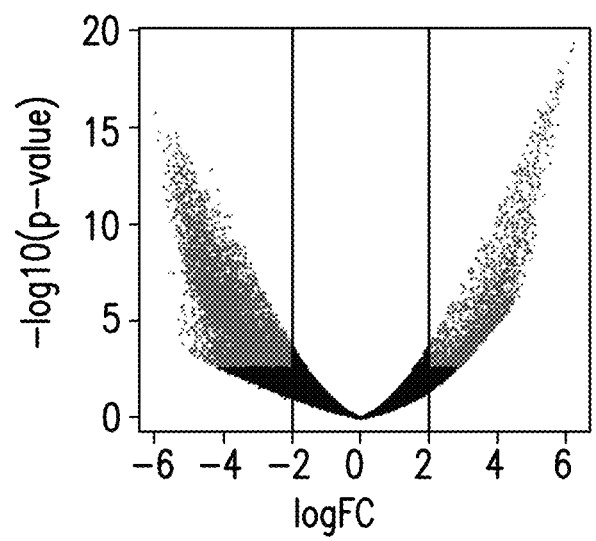
FIG. 2A
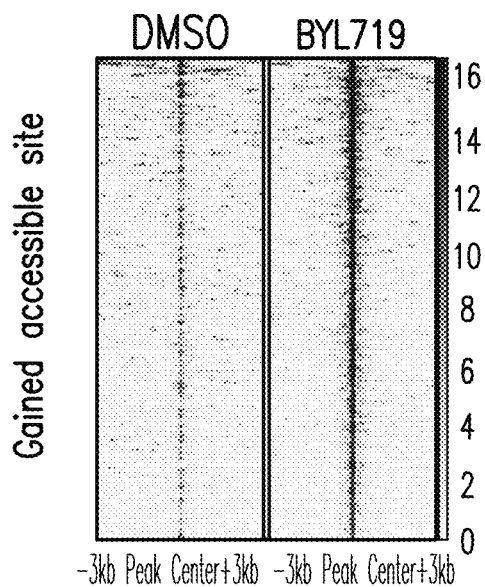
FIG. 2B
Enriched Motifs on Accessible sites
ERE (Nuclear Receptor)
FOXA1 (Forkhead)
PBX1 (Homeobox)
FIG. 2C Enriched Motifs on Accessible sites ATAC-seq Patient 1
- Esrra (Nuclear Receptor)
- FOXA1 (Forkhead)
- PBX1 (Homeobox)

ATAC-seq Patient 2
- ERE (Nuclear Receptor)
- Forkhead
- PBX1 (Homeobox)

FIG. 2E

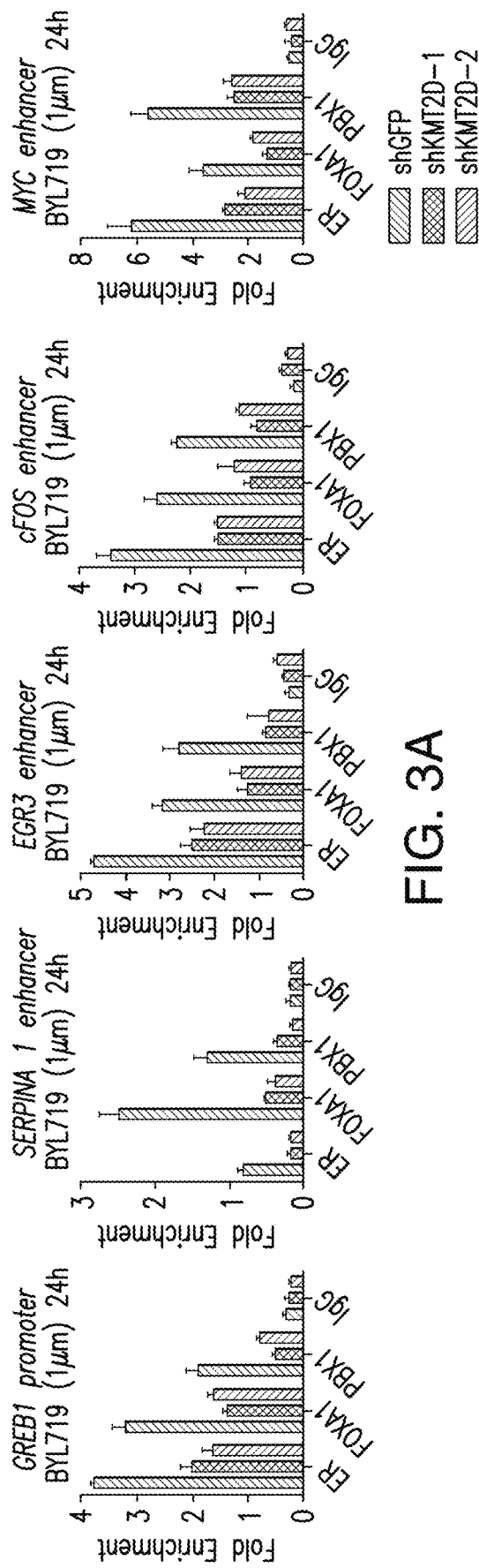
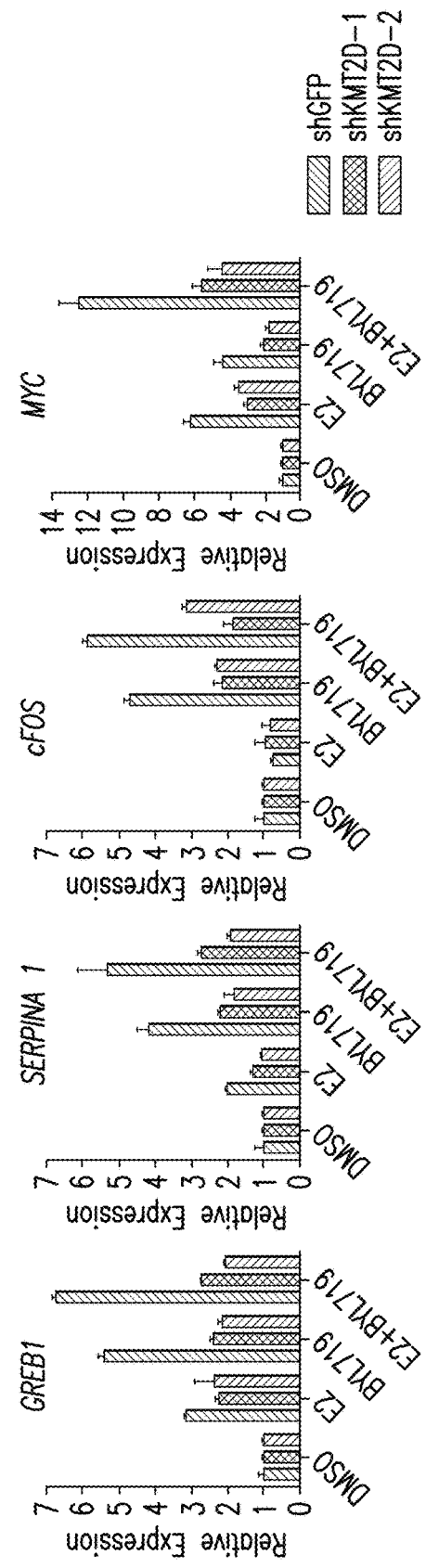
FIG. 3A
FIG. 3B

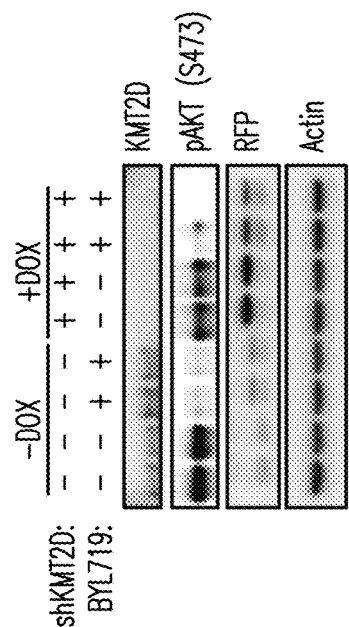
FIG. 3C
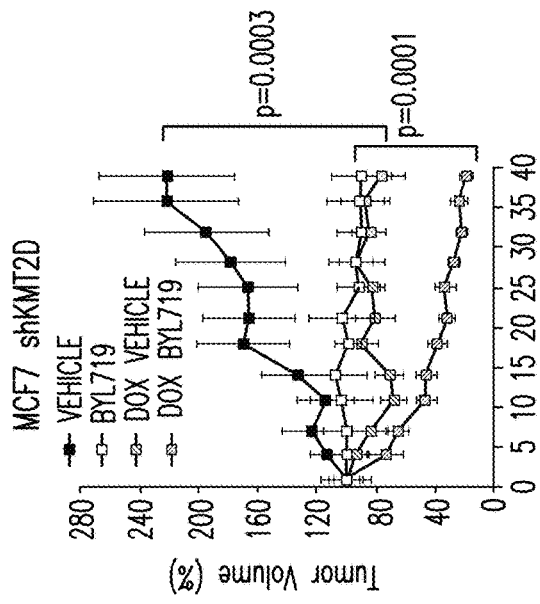
FIG. 3D
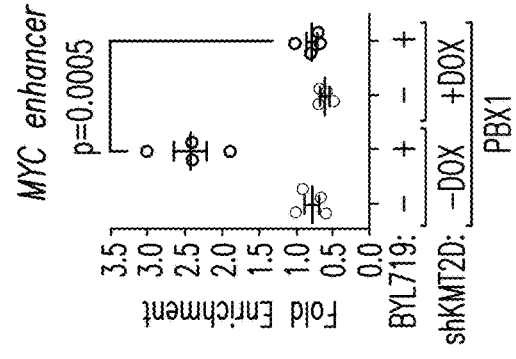
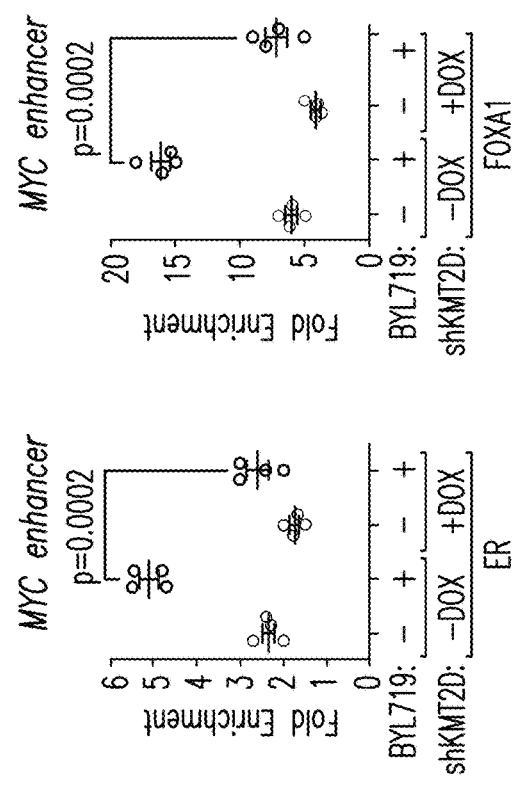
FIG. 3E

|  | S1331 |  | S1762 |
|---|---|---|---|
| H. sapiens | GRARLKST |  | RRGRKKSK |
| P. troglodytes | GRARLKST |  | RRGRKKSK |
| M. musculus | GRARLKST |  | RRARKKSK |
| X. laevis | GRSRLKST |  | RRGRKKSK |
| D. rerio | GRGRGRSR |  | RRGRKKSK |
| AGC consensus site | RXRXXS/T |  | RXRXXS/T |

FIG. 4A

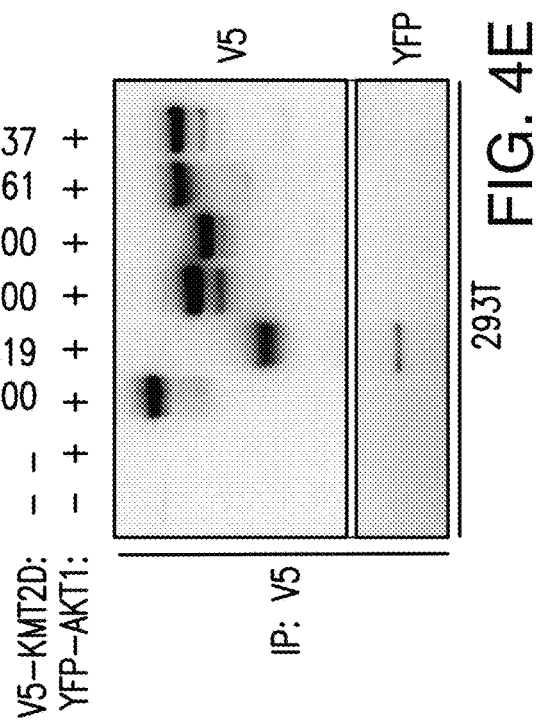
FIG. 4E
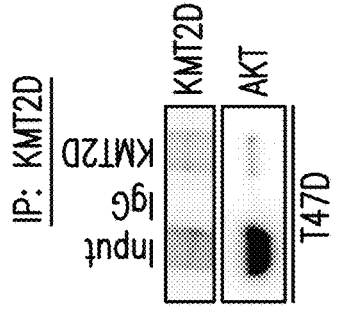
FIG. 4C
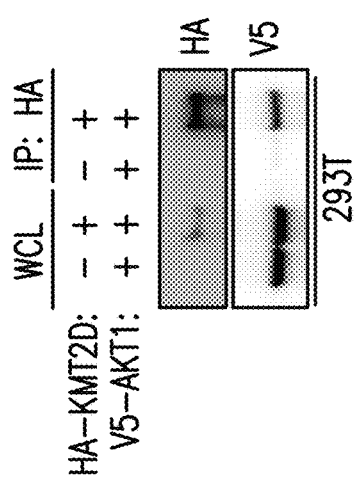
FIG. 4B
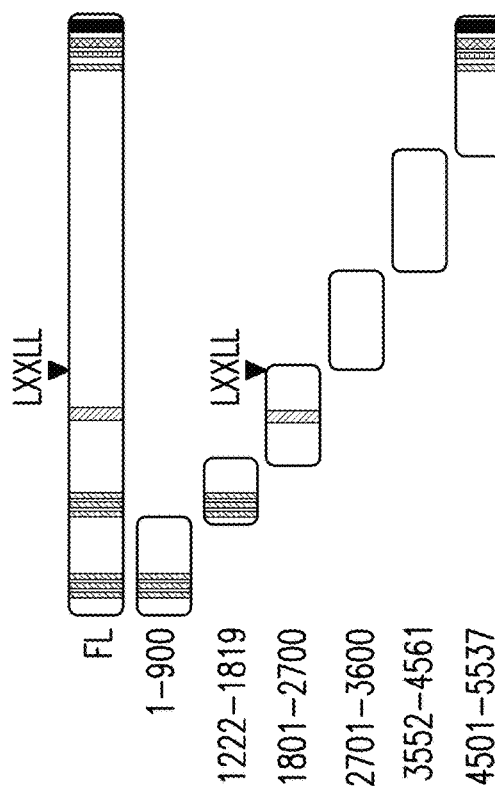
FIG. 4D

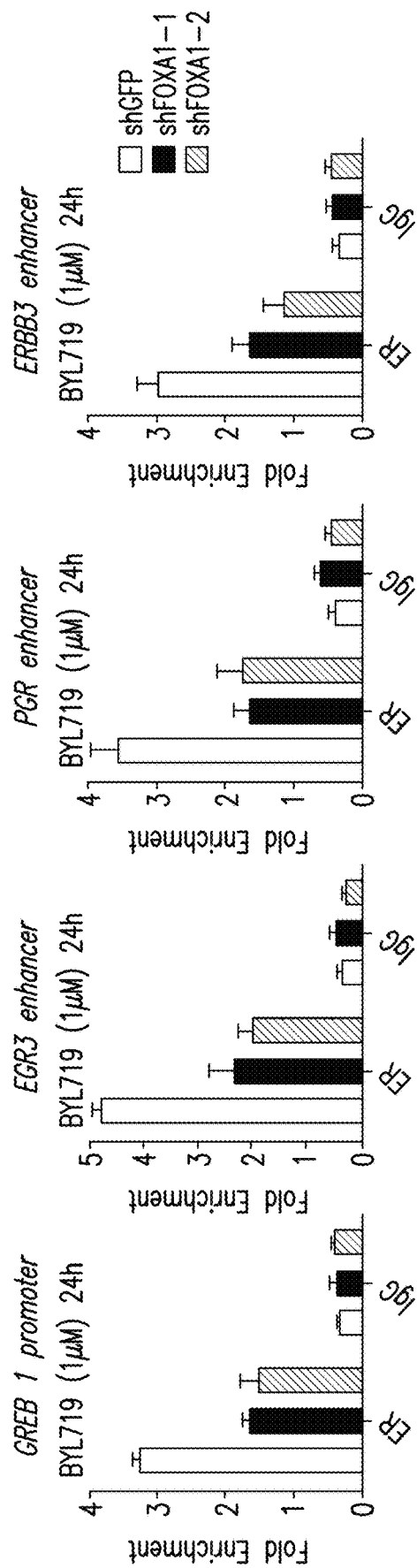
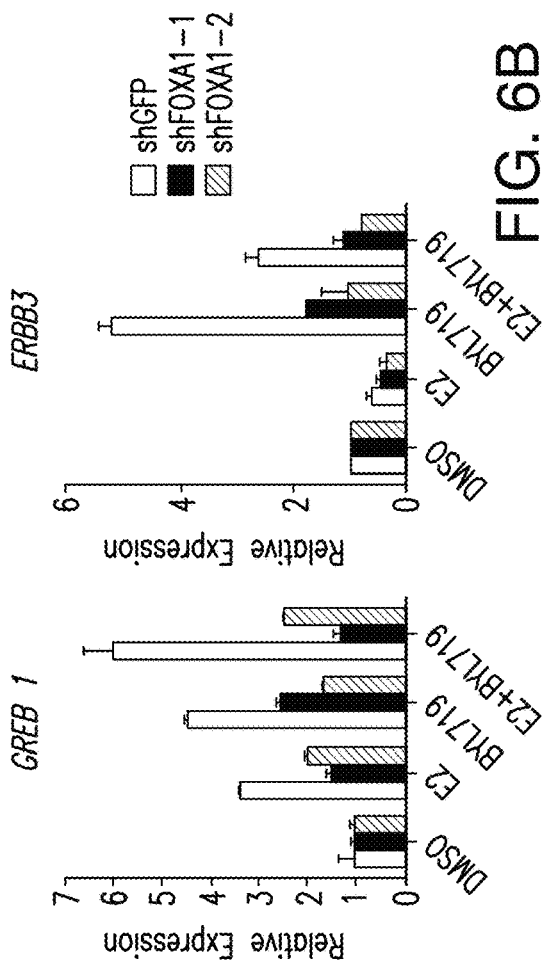
FIG. 6A
FIG. 6B

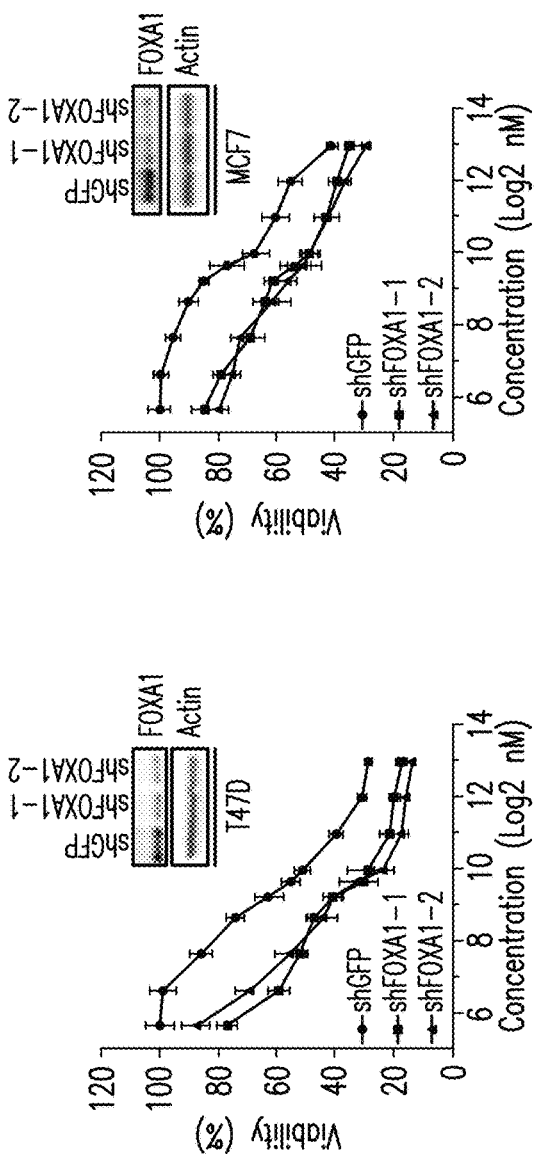
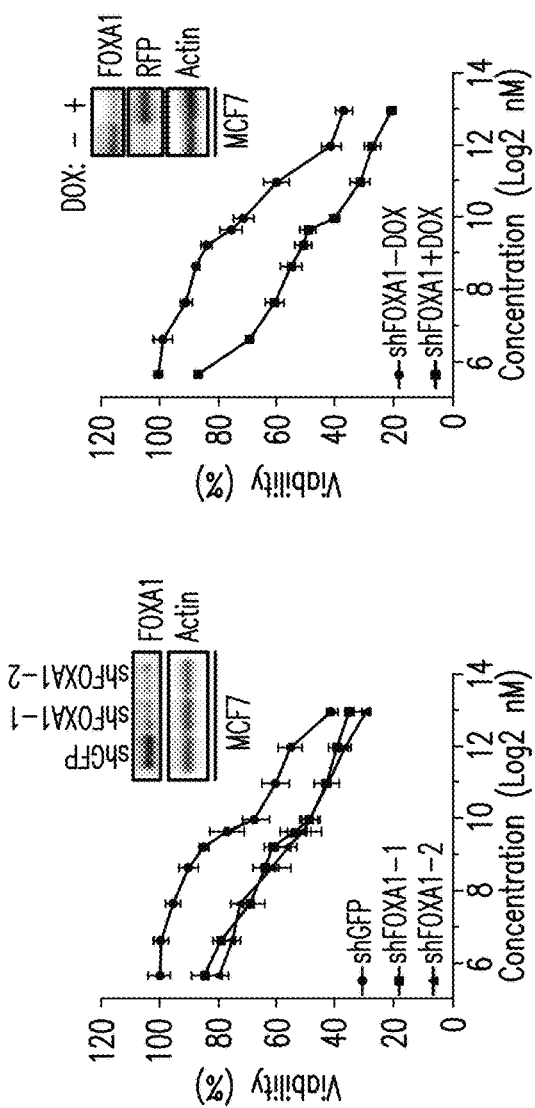
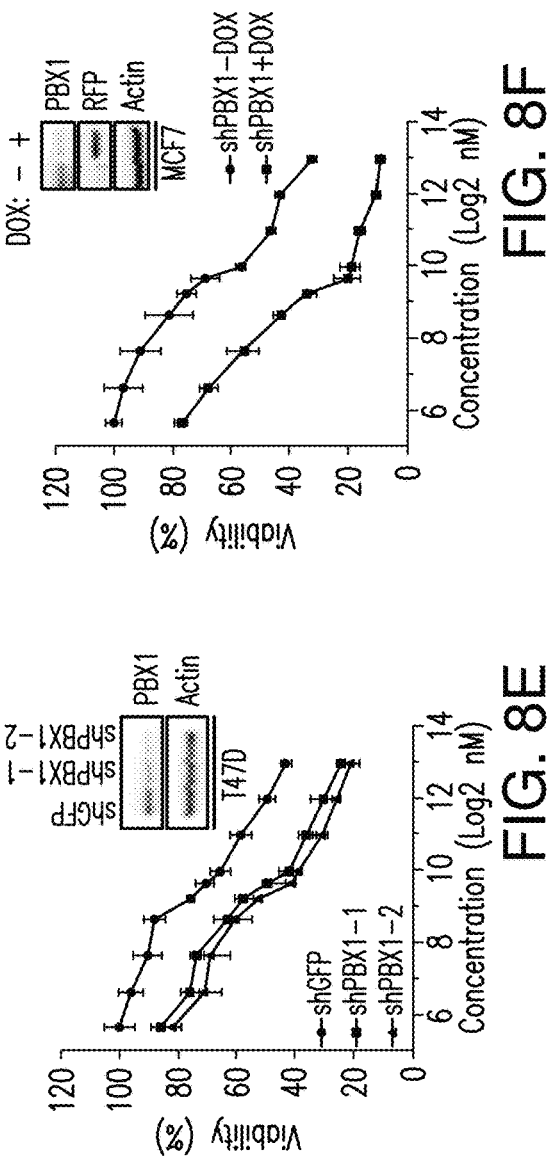
FIG. 8A  FIG. 8B  FIG. 8C
FIG. 8D  FIG. 8E  FIG. 8F

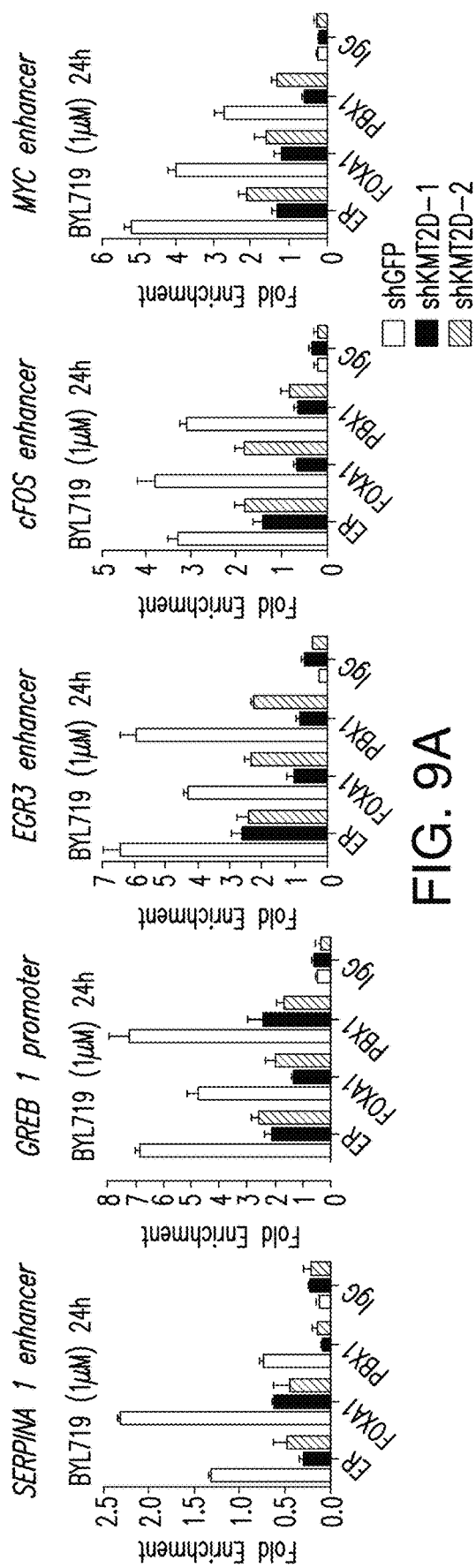
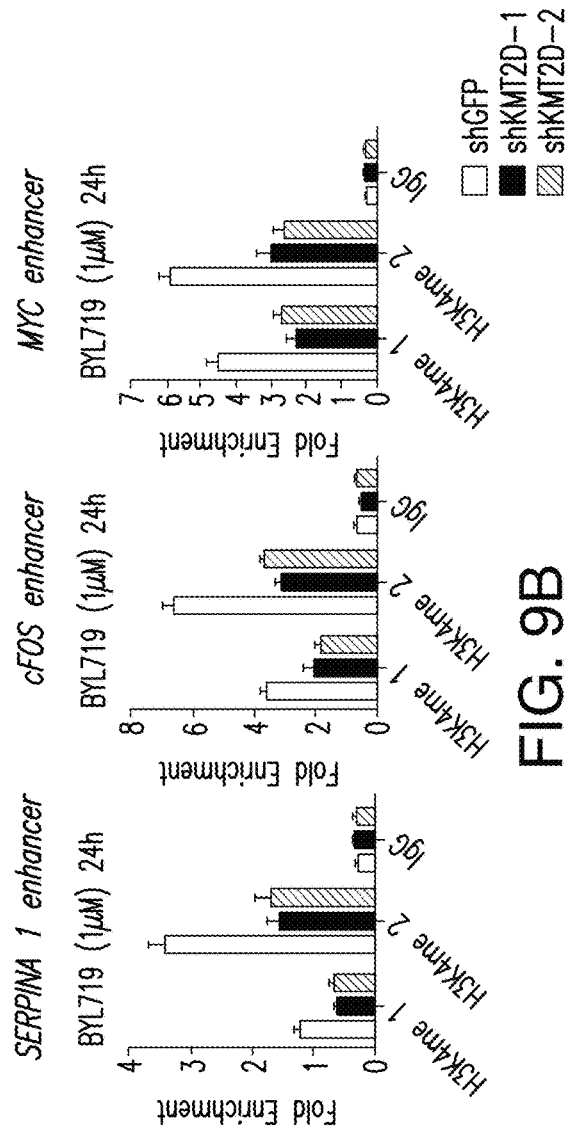
FIG. 9A
FIG. 9B

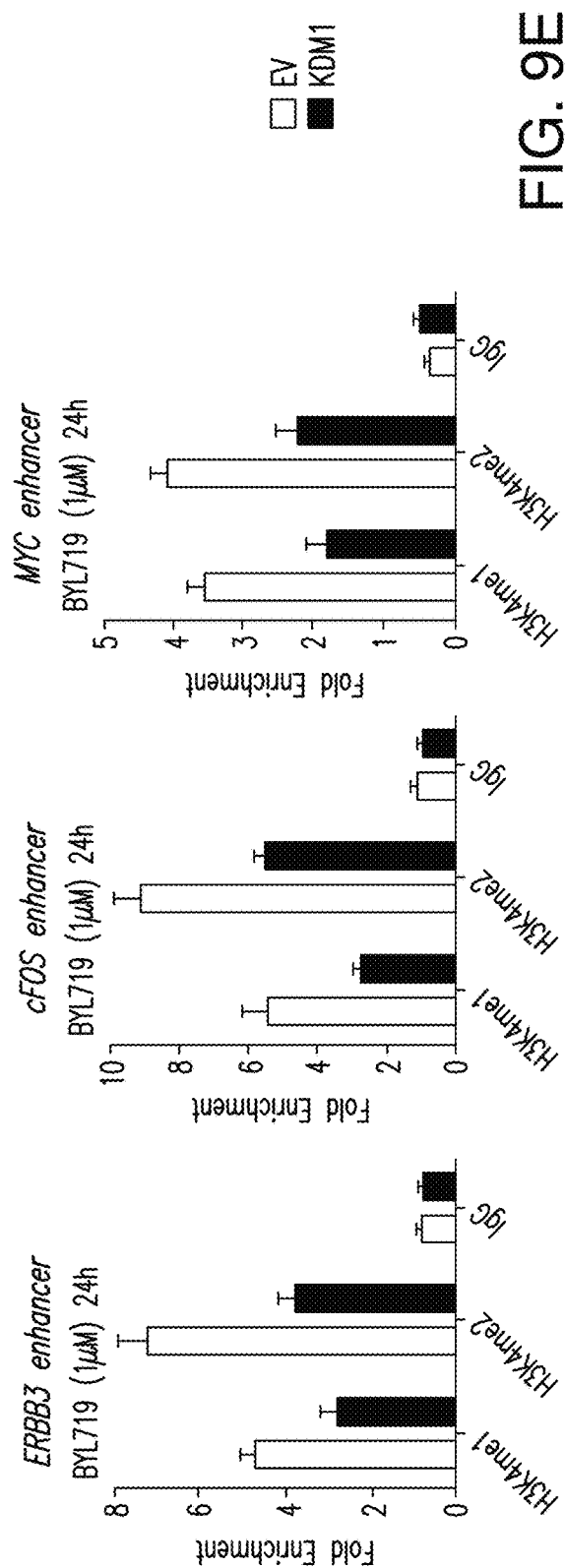
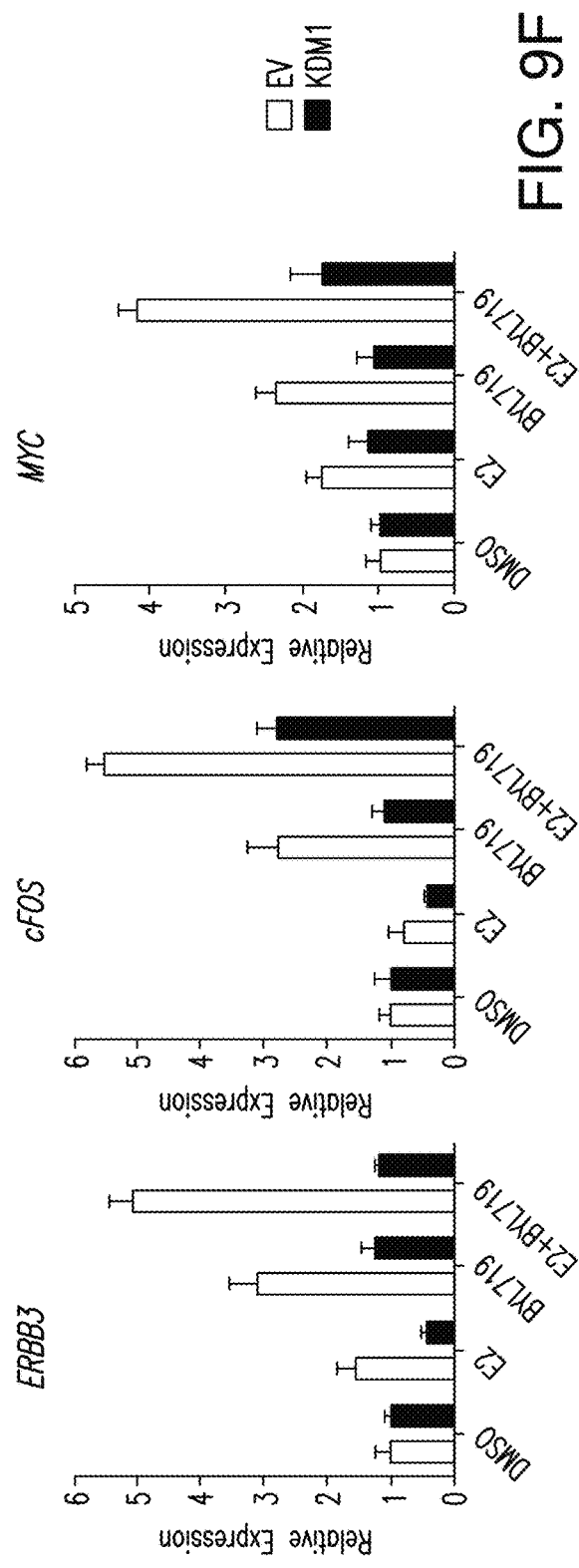
FIG. 9E
FIG. 9F

Figure 11I:
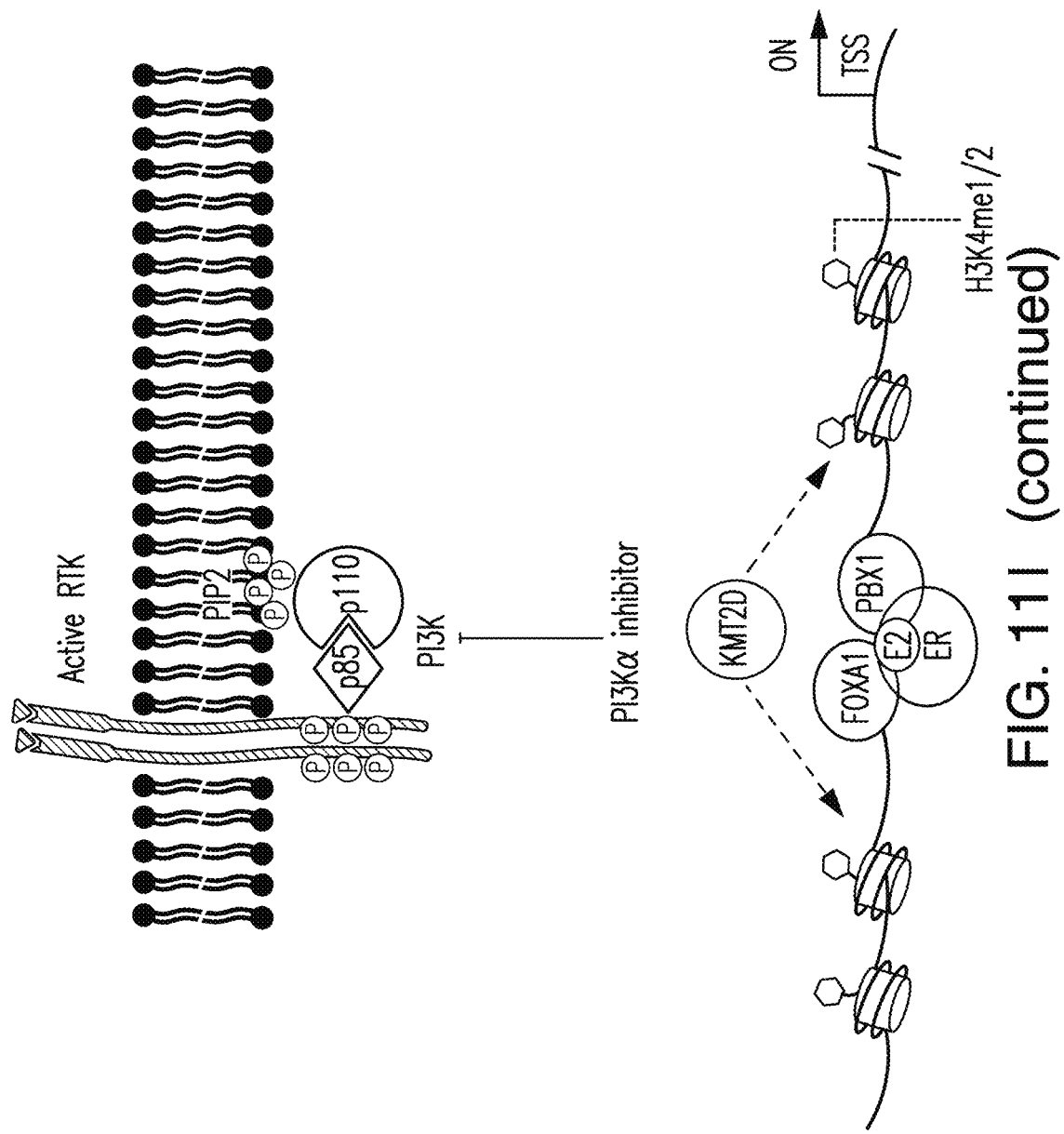

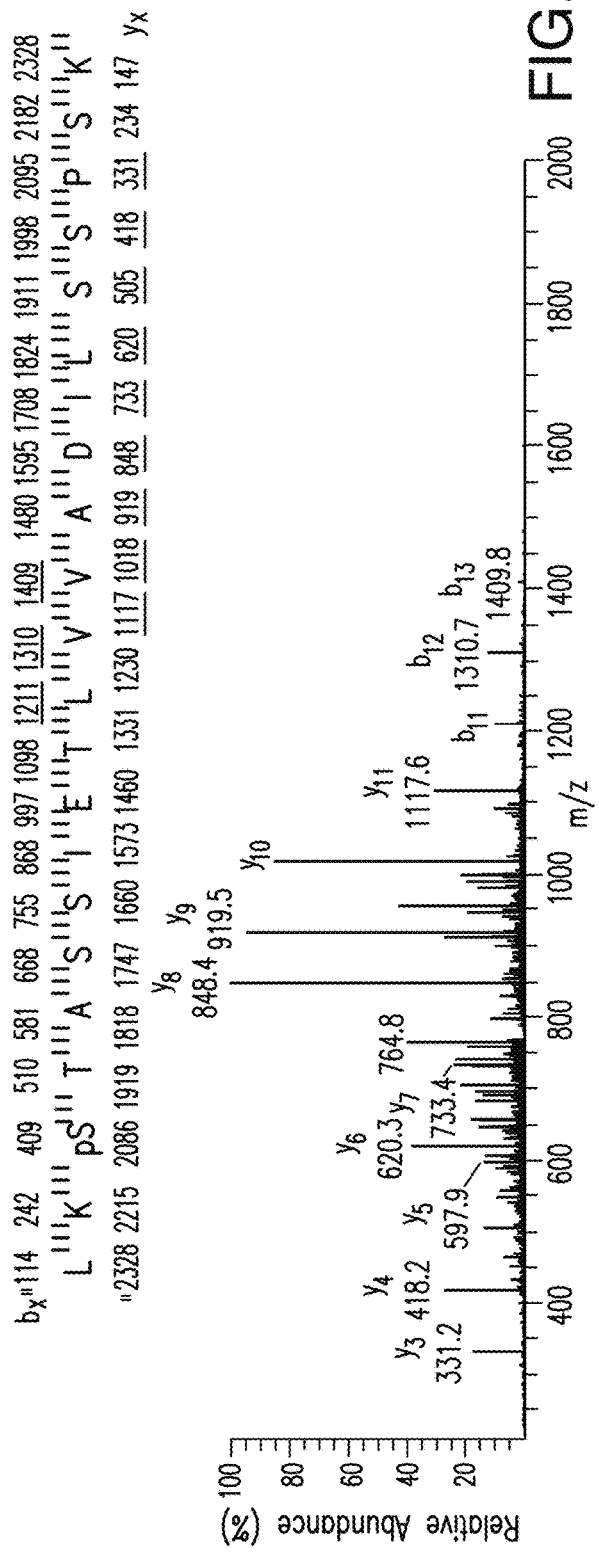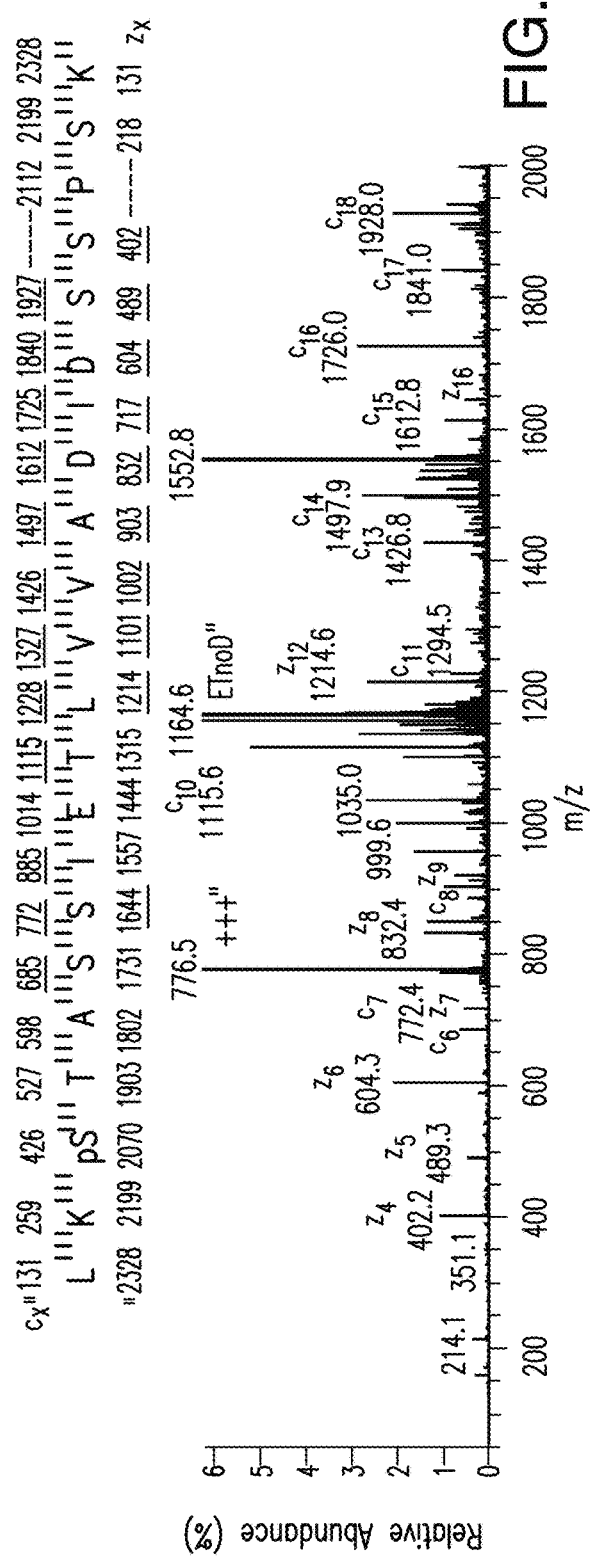
FIG. 11A
FIG. 11B

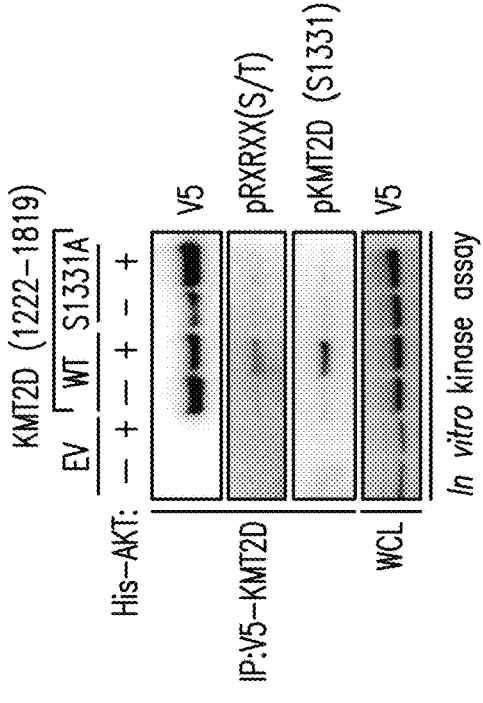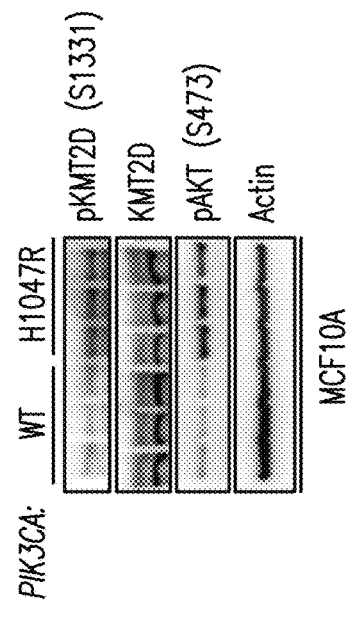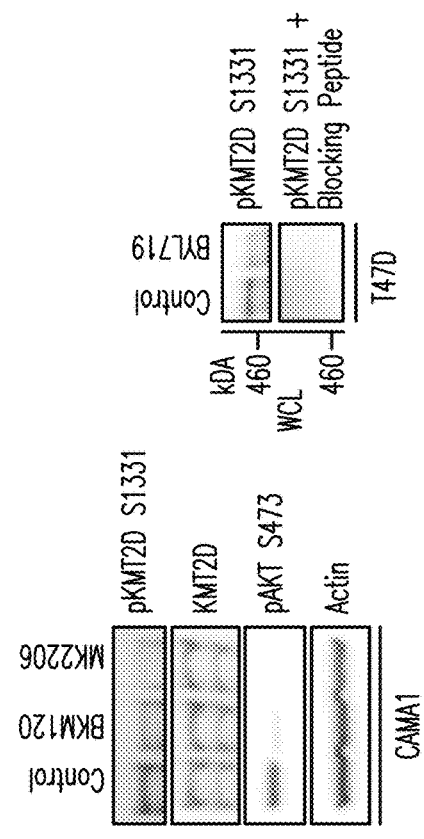
FIG. 11C
FIG. 11D
FIG. 11E
FIG. 11F
FIG. 11G
FIG. 11H

INHIBITION OF KMT2D FOR THE TREATMENT OF CANCER

CROSS REFERENCE TO RELATED APPLICATIONS

The present application is a continuation of International Application No. PCT/US2017/061073, filed Nov. 10, 2017, which claims priority to U.S. Provisional Application No. 62/420,324, filed Nov. 10, 2016, the contents of all of which are incorporated by reference herein in their entireties.

SEQUENCE LISTING

The instant application contains a Sequence Listing which has been submitted electronically in ASCII format and is hereby incorporated by reference in its entirety. Said ASCII copy, created on May 10, 2019, is named 072734_0873_SL.txt and is 9,833 bytes in size.

1. INTRODUCTION

The present invention relates to the administration of a KMT2D inhibitor for the treatment of a cancer, and also to the administration of a KMT2D inhibitor in combination with a PI3Kα inhibitor for the treatment of a cancer.

2. BACKGROUND OF THE INVENTION

Myeloid/lymphoid or mixed-lineage leukemia protein 2 (KMT2D) is an enzyme that is encoded by the Histone-lysine N-methyltransferase 2D (KMT2D) gene. KMT2D is also known as MLL2 and MLL4 in the literature (see, e.g., Kantidakis et al., Genes & Dev. 30:408-420 (2016) and Guo et al., Oncotarget 4(11): 2144-2153 (2013)). KMT2D is a member of the SET (Su(var)3-9, Enhancer-of-zeste, Trithorax) family of proteins, and exhibits histone methyltransferase activity via its highly conserved SET domain (Micale et al., Orphanet Journal of Rare Diseases. 6:38-45 (2011)). KMT2D has been shown to methylate the lysine 4 position of histone H3 (H3K4), which is a chromatin modification that correlates with transcriptionally active chromatin (Nataraj an et al., Cancer Cell Int. 10:13 (2010)). KMT2D has been shown to be a key regulator of gene expression during cellular differentiation of diverse tissues (Guo et al., Oncotarget. 4(11):2144-53 (2013)).

KMT2D is commonly mutated in patients suffering from Kabuki syndrome, a rare pediatric congenital disorder characterized by short stature, skeletal, visceral and dermatoglyphic abnormalities, cardiac anomalies and immunological defects (Cheon et al., J. Hum. Genet. 59 (6):321-5 (2014)). KMT2D mutations have also been detected in small cell lung cancer, renal carcinoma, prostate cancer, gastric carcinoma and large B-cell lymphoma, and have been shown to exhibit oncogenic activity (Natarajan et al. (2010); Je et al., Neoplasma 60(2): 188-95 (2013); Haige et al., Int. J. Clin. Exp. Pathol. 8(10):13043-13050 (2015)).

3. SUMMARY OF THE INVENTION

This present invention relates to the administration of a KMT2D inhibitor for the treatment of a cancer. The present invention is based, at least in part, on the discovery that upon PI3K inhibition, KMT2D activity is upregulated, resulting in an increase in the expression of genes involved in cancer cell proliferation and tumor growth.

In certain embodiments, the present invention provides a method for treating a subject having a cancer that includes administering, to the subject, a therapeutically effective amount of a KMT2D inhibitor. In certain embodiments, the cancer is breast cancer. In certain embodiments, the method can further include administering, to the subject, a therapeutically effective amount of a second anti-cancer agent. For example, and not by way of limitation, the second anti-cancer agent can be a PI3Kα inhibitor, e.g., BYL719. In certain embodiments, a PI3Kα inhibitor, e.g., BYL719, may be administered prior to a KMT2D inhibitor. In certain other embodiments, a PI3Kα inhibitor, e.g., BYL719, may be administered concurrently with a KMT2D inhibitor such that their therapeutic effects overlap. In certain other embodiments, a PI3Kα inhibitor, e.g., BYL719, may be administered essentially simultaneously with a KMT2D inhibitor. In certain other embodiments, a PI3Kα inhibitor, e.g., BYL719, may be administered after a KMT2D inhibitor. In certain embodiments, a cycle of treatment with a PI3Kα inhibitor, e.g., BYL719, may be administered prior to a cycle of treatment with a KMT2D inhibitor. In certain other embodiments, a cycle of treatment with PI3Kα inhibitor, e.g., BYL719, may be administered concurrently with a cycle of treatment with KMT2D inhibitor such that their therapeutic effects overlap. In certain other embodiments, a cycle of treatment with a PI3Kα inhibitor, e.g., BYL719, may be administered essentially simultaneously with a cycle of treatment with a KMT2D inhibitor. In certain other embodiments, a cycle of treatment with PI3Kα inhibitor, e.g., BYL719, may be administered after a cycle of treatment with a KMT2D inhibitor.

The present invention further provides a method of reducing or inhibiting the growth of a tumor comprising administering to the tumor and/or contacting the tumor with a therapeutically effective amount of a KMT2D inhibitor. In certain embodiments, a method of the present invention results in the targeted degradation of KMT2D, e.g., by administering an inhibitor and/or compound that interacts with KMT2D and is conjugated to a phthalimide, e.g., a phthalimide derivative. In certain embodiments, the present invention provides a method of reducing or inhibiting the growth or proliferation rate of a cancer cell comprising administering to the cancer cell and/or contacting the cancer cell with a therapeutically effective amount of a KMT2D inhibitor.

In certain embodiments, the present invention further provides a method for lengthening the period of survival of a subject having a cancer comprising administering, to the subject, a therapeutically effective amount of a KMT2D inhibitor. In certain embodiments, the period of survival of the subject having cancer is lengthened by about 1 month, about 2 months, about 4 months, about 6 months, about 8 months, about 10 months, about 12 months, about 14 months, about 18 months, about 20 months, about 2 years, about 3 years, about 5 years or more. In certain embodiments, the cancer is breast cancer. In certain embodiments, the method can further include administering, to the subject, a therapeutically effective amount of a second anti-cancer agent. For example, and not by way of limitation, the second anti-cancer agent can be a PI3Kα inhibitor, e.g., BYL719.

The present invention further provides a pharmaceutical composition for treating a cancer that includes a therapeutically effective amount of a KMT2D inhibitor and a pharmaceutically acceptable carrier. In certain embodiments, the pharmaceutical composition further comprises a second anti-cancer agent. In certain embodiments, the second anti-cancer agent is a PI3Kα inhibitor, e.g., BYL719.

The present invention further provides a kit for treating a cancer comprising a KMT2D inhibitor. In certain embodiments, the kit comprises instructions for using the KMT2D inhibitor for treating a subject that has cancer. In certain embodiments, the kit further comprises a second anti-cancer agent. In certain embodiments, the second anti-cancer agent is a PI3Kα inhibitor. In certain embodiments, the PI3Kα inhibitor is BYL719. In certain embodiments, the cancer is breast cancer.

4. BRIEF DESCRIPTION OF FIGURES

FIG. 1A-H. FOXA1 and PBX1 are required for the activation of ER function upon PI3K inhibition. A, B. Volcano plot of ER ChIP-seq and FOXA1 ChIP-seq for T47D cells treated with DMSO or BYL719 (1 NM) for 24 h. The x-axis represents log FC (log fold change) and y-axis represents −log 10 (p-value). The light gray dots correspond to the ER or FOXA1 binding events that are significantly differentially bound upon BYL719 treatment. Also shown are the top enriched motifs observed at the gained ER or FOXA1 binding events upon BYL719 treatment. At the ER gained binding events: ERE, oestrogen responsive elements (p value: 1e−70) FOXA1, forkhead (p value: 1e−27) and homeobox motif (p value: 1e−20). At the FOXA1 gained bindings events: FOXA1, forkhead (p value: 1e−260), nuclear receptor class (p value: 1e−59) and homeobox motif (p value: 1e−29). C. Example of a binding region of a BYL719-induced ER and FOXA1 binding event presented as read per million (RPM). D. ChIP-qPCR for ER occupancy in the enhancer and promoter regions after FOXA1 was knockdown by two distinct shRNAs in T47D cells upon treatment with BYL719 (1 μM) for 24 h. Values are represented as relative enrichment; the ratio of mean percentage of input enrichment of the candidate gene over the mean percentage of input enrichment of a control gene. Data correspond to one representative assay from a total of 2 or 3 independent assays. E. mRNA levels measured by RT-qPCR in hormone depleted T47D cells for 3 days followed by treatment with DMSO, E2 (100 nm), BYL719 (1 μM) or E2+BYL719 for 24 h. F. MCF7 shFOXA1 doxycyline inducible in vivo xenograft treated daily with vehicle or BYL719 daily (25 mg/kg) (n=10/arm). G. Western blot analysis of tumors collected at the end of the experiment. H. Tissue ChIP-qPCR for ER occupancy in the candidate target genes of randomly collected tumors from each arm.

FIG. 2A-E. PI3K inhibition remodels the chromatin landscape towards an active ER-dependent transcription. A. Volcano plot of ATAC-seq from T47D cells treated with DMSO or BYL719 for 24 h. The x-axis represents log FC (log fold change) and y-axis represents −log 10 (p-value). The light gray dots correspond to the significant accessible sites upon BYL719 treatment. B. Heat map of gained accessible sites upon BYL719 treatment, shown in a horizontal window of ±3 kb from the peak center. C. The TOP enriched motifs of the accessible sites upon BYL719 treatment: ERE, oestrogen responsive elements, (p value: 1e−11), FOXA1, forkhead (p value: 1e−205) and PBX1, homeobox (p value: 1e−144). D. Examples of ER, FOXA1 ChIP-seq binding region and ATAC-seq open-chromatin regions in T47D cells and breast cancer patient samples treated with PI3Kα inhibitors presented as read per million (RPM). The patient samples were collected before the commencement of the treatment with PI3Kα inhibitors, and after about 14 days of treatment between 2 to 6 h after the daily drug administration. E. The enriched motifs of the gained accessible sites upon PI3Kα inhibitor treatment: Patient 1 enriched motifs: Esrra, nuclear receptor class (p value: 1e−15), FOXA1, forkhead (p value: 1e−22) and PBX1, homeobox (p value: 1e−24). Patient 2 enriched motifs: ERE, nuclear receptor (p value: 1e−6), Forkhead class (p value: 1e−7), PBX1, homeobox (p value: 1e−5).

FIG. 3A-H. Activation of ER-dependent transcription by PI3K pathway inhibition is orchestrated by KMT2D. A. ChIP-qPCR for ER, FOXA1, PBX1 and IgG control in promoter, enhancer regions of the specified regions upon treatment with BYL719 (1 μM) for 24 h after KMT2D knockdown by two distinct shRNAs. B. RT-qPCR in hormone depleted T47D cells for 3 days followed by treatment with DMSO, E2 (100 nM), BYL719 (1 μM) or E2+BYL719 for 24 h. Values represent the average of 2 or 3 replicates. C. MCF7 inducible shKMT2D in vivo xenograft treated with vehicle or BYL719 daily at 25 mg/kg dose (n=10/arm). D. Western blot analysis of the tumor lysates collected at the end of the experiment. RFP is red fluorescent protein. E. Tissue ChIP-qPCR of ER, FOXA1 and PBX1 binding of tumors collected at the end of the experiment from each arm. F. ChIP-qPCR for KMT2D, H3K4me1 and H3K4me2, and IgG control upon treatment with BYL719 (1 μM) for 2, 4, 8, 12, and 24 h. G. H3K4 methyltransferase activity of T47D nuclear extracts on a synthetic H3 peptide upon treatment with BYL719 (1 μM) for 4, 8 and 24 h as measured by H3K4methyltrasferase kit. H. Immunoblot analysis of H3K4me1, H3Kme2, Actin and H3 upon treatment with BYL719 (1 μM) for 2, 4, 8 and 24 h in T47D cells.

FIG. 4A-H. AKT1 interacts with and phosphorylates KMT2D, attenuating its activity. A. In silico analysis of RXRXXS/T (R is arginine, X is any amino acid, and (S/T) is a phosphorylatable Serine or Threonine) motifs of KMT2D primary structure in the specified species (SEQ ID NOS 37-46, respectively, in order of appearance). B. HA co-immunoprecipitation assay in 293T cells transfected with the indicated plasmids and probed with HA and V5 antibodies. WCL is whole cell lysate. C. KMT2D co-imunoprecipitation assay in T47D cells and immunobloted with KMT2D and AKT antibodies. D. Schematic representation of different KMT2D truncated fragments used for co-immunoprecipitation assays. Also shown are the key domains of KMT2D protein: PHD (plant homeodomain); HMG (high mobility group); FYRN (FY-rich N-terminal); FYRC (FY-rich C-terminal); SET: (Su(var)3-9, enhancer-of-zeste, trithorax) domain. E. Co-immunoprecipitation assays in 293T cells transfected with YFP-AKT1 and each of the indicated V5 tagged KMT2D fragments. F. In vitro kinase assay using recombinant His-AKT and wild type (WT) KMT2D or S1331A KMT2D immunoprecipitated from 293T cells as a substrate. G. H3K4 methyltransferase activity of control IgG, WT, S1331A, and S1331D KMT2D immunoprecipitated from 293T cells using a synthetic H3 substrate as measured using a H3K4 methyltransferase kit. H. Immunoblot analysis of the indicated histone methylation marks in 293T cells transfected with control, WT, S1331A and S1331D KMT2D vectors.

Figure 5A:
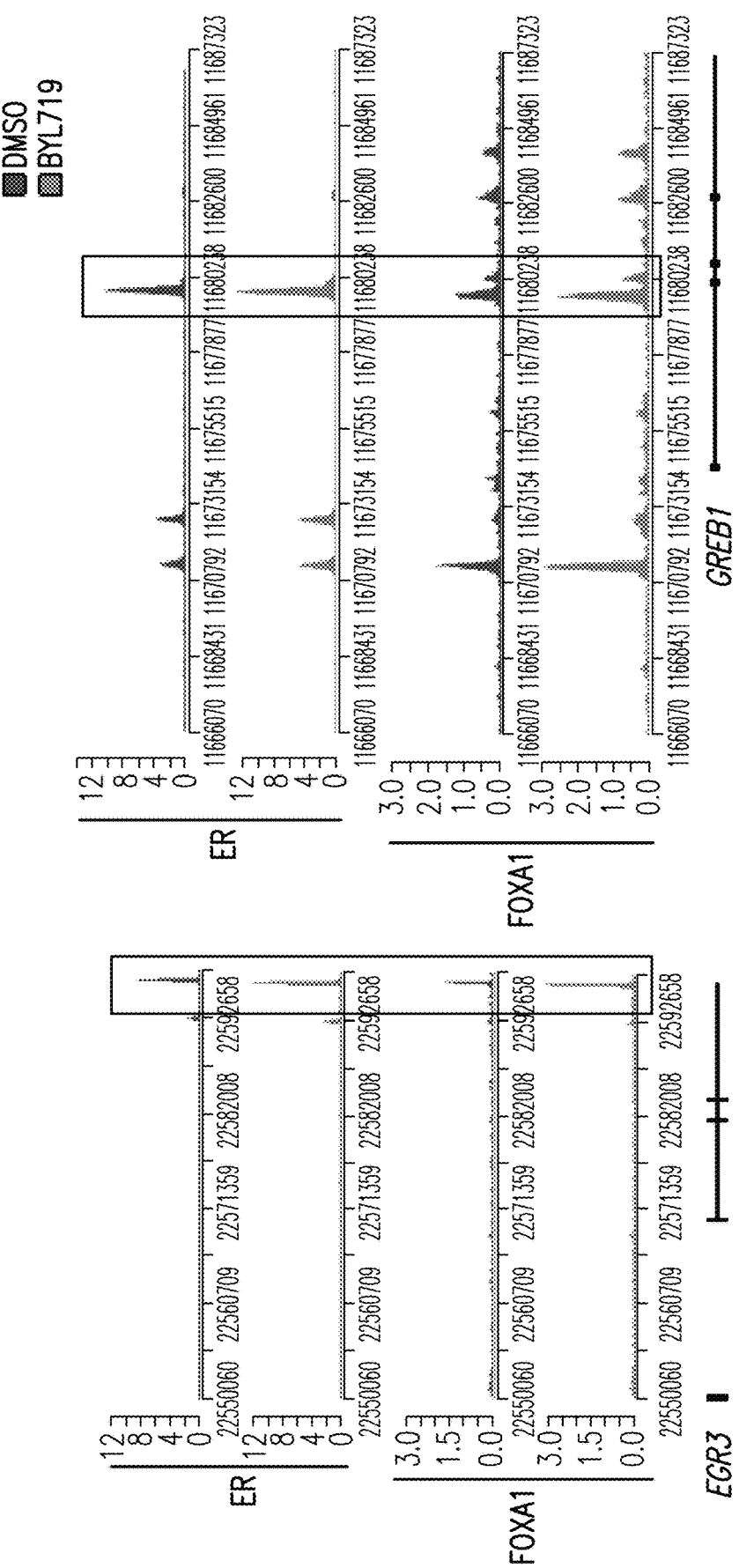
Figure 5B:
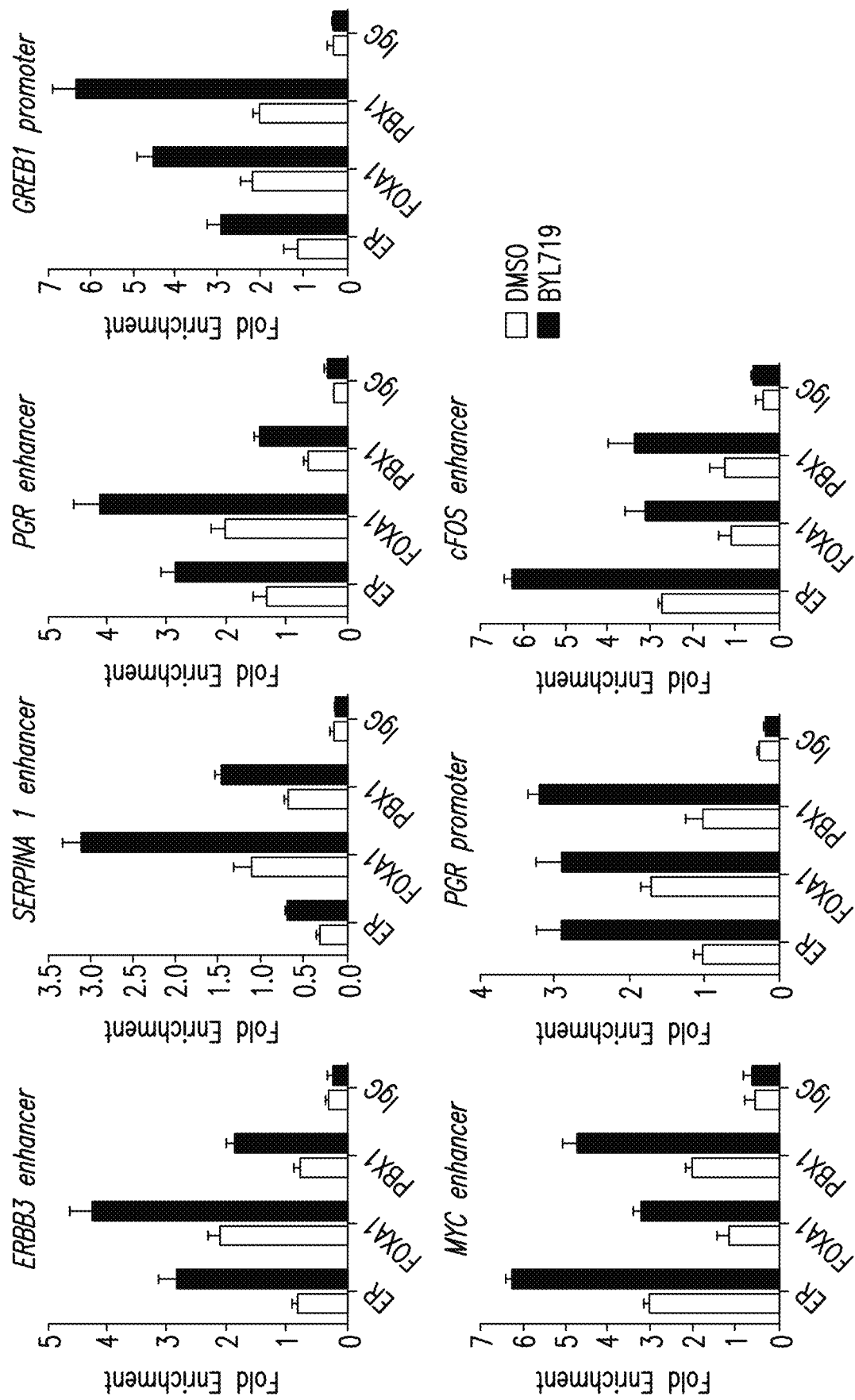
Figure 5C:
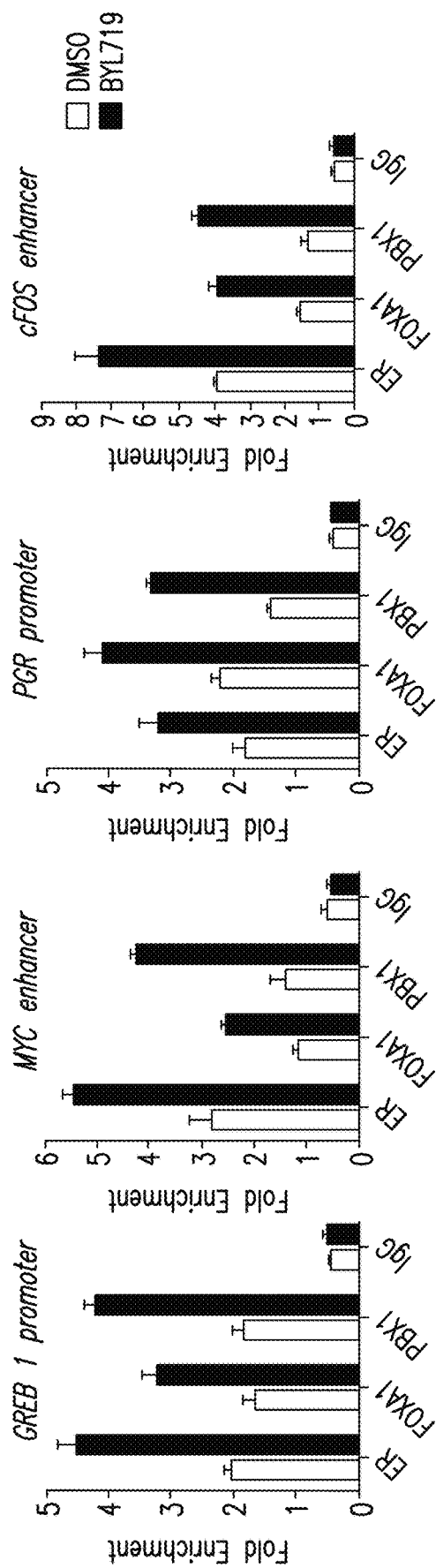

FIG. 5A-C. FOXA1, PBX1 and ER recruitment to shared target genes is enhanced upon PI3K blockage. A. Examples of ER and FOXA1 binding regions enhanced upon BYL719 treatment (1 μM) for 24 h in T47D cells. B. ChIP-qPCR for ER, FOXA1, PBX1 and IgG in T47D cells treated with DMSO or BYL719 (1 rpm) for 24 h. Values are represented as relative enrichment; the ratio of mean percentage of input enrichment of the candidate gene over the mean percentage of input enrichment of a control gene. C. Similar assay performed in MCF7 cells.

FIG. 6A-D. FOXA1 regulates the activation of ER upon PI3K inhibition. A. ChIP-qPCR to test ER occupancy in the enhancer or promoter regions of indicated target genes when FOXA1 is silenced by two distinct shRNAs in T47D cells treated with BYL719 (1 µM) for 24 h. B. mRNA levels were measured by RT-qPCR in hormone depleted shGFP or shFOXA1 T47D cells for 3 days followed by treatment with DMSO, E2 (100 nm), BYL719 (1 µM) or E2+BYL719 for 24 h. C, D. Same as (A and B) above but in MCF7 cells.

FIG. 7A-D. PBX1 regulates the activation of ER upon PI3K inhibition. A. ChIP-qPCR for ER occupancy in shGFP or shPBX1 (#1, #2) T47D cells treated with BYL719 (1 µM) for 24 h. B. RT-qPCR was used to measure mRNA levels of hormone depleted shGFP or shPBX1 T47D cells for 3 days followed by treatment with DMSO, E2, BYL719 or E2+BYL719 for 24 h. C, D. Same as above but in MCF7 cells.

FIG. 8A-J. FOXA1 or PBX1 silencing augments the clinical activity of BYL719. A. Dose response cell proliferation curves of T47D cells transduced with shGFP, shFOXA1 (#1, #2) and treated with increasing concentration of BYL719 for 5 days. Also shown is the western blot testing knockdown of FOXA1. B. Same as (A) but in MCF7 cells. C. Cell viability assays in MCF7 cells transduced with doxycycline (DOX) inducible FOXA1 knockdown (shFOXA1+DOX) and treated with increasing concentration of BYL719 for 5 days. Also shown is the western blot demonstrating knockdown of FOXA1 upon doxycycline administration. D. E. Proliferation curves of T47D cells (D) and MCF7 cells (E) transduced with shGFP, shPBX1 (#1, #2) and treated with BYL719 for 5 days. Also shown is the western blot demonstrating knockdown of PBX1. F. Proliferation curves of MCF7 cells transduced with doxycycline inducible shPBX1 and treated with BYL719 for 5 days. Also shown is the western blot demonstrating knockdown of PBX1 upon doxycycline administration. G. MCF7 shPBX1 in vivo xenograft activated in the presence of doxycycline and treated with vehicle or BYL719 daily (25 mg/kg) (n=10/arm). H. Western blot analysis of tumors collected at the end of the experiment. I. Tissue ChIP-qPCR to test the occupancy of ER in each tumor arm. J. Example of ER, FOXA1 ChIP-seq binding region and open chromatin region of PGR in T47D cells treated with DMSO and BYL719 (1 µM) for 24 h.

FIG. 9A-F. KMT2D is required for the FOXA1-PBX1-dependent ER activation upon PI3K blockage. A. ChIP-qPCR for ER, FOXA1, PBX1 and control IgG occupancy in cells silenced of KMT2D and treated with BYL719 (1 µM) for 24 h in MCF7 cells. B. ChIP-qPCR to test H3K4me1 and H3K4me2 binding in control cells or cells depleted of KMT2D by two distinct shRNAs (#1 and #2) and treated with BYL719 (1 µM) for 24 h. C. Hormone depleted shGFP or shKMT2D (#1, #2) MCF7 cells were subjected to treatment with DMSO, E2 (100 nM), BYL719 (1 µM) or E2+BYL719 for 24 h and mRNA levels were measured by RT-qPCR. D. ChIP-qPCR analysis to test the binding of ER, FOXA1, PBX1, and control IgG in the regions of the specified ER target genes after overexpression of H3K4me1/2 demethylase, KDM1, or empty vector (EV) in MCF7 cells and upon treatment with BYL719 (1 µM) for 24 h. Also shown is the western blot showing overexpression of FLAG-KDM1 in MCF7 cells. E. ChIP-qPCR analysis for H3K4me1/2 and IgG occupancy in the cells overexpressed with KDM1 or empty vector. F. mRNA levels were measured by RT-qPCR in MCF7 cells which were depleted of hormones for 3 days, transfected with empty vector or KDM1 and treated with DMSO, E2 (100 nM), BYL719 (1 µM) or E2+BYL719 for 24 h.

FIG. 10A-D. KMT2D silencing augments the activity of BYL719. A-C. Dose response curves from T47D or MCF7 cells transduced with shGFP, shKMT2D (#1, #2) and treated with BYL719 (1 µM) for 5 days. Also shown are the dose response proliferation curves from MCF7 cells transduced with doxycycline inducible shKMT2D and treated with BYL719 (1 µM) for 5 days. Moreover, RT-qPCR analysis demonstrating knockdown of KMT2D (#1, #2) is also shown. D. ChIP-qPCR for KMT2D, H3K4me1 and H3K4me2 and IgG control upon treatment with BYL719 (1 µM) for 2, 4, 8, 12, and 24 h.

FIG. 11A-I. Activation of PI3K results in phosphorylation of KMT2D. A, B. CAD and ETD mass spectra respectably recorded on the $(M+3H)^{3+}$ ions at m/z=776.72 and retention time 51.8 min. Tandem mass spectra recorded during targeted analyses (nHPLC-ESI-MS/MS) of peptides generated in an in gel tryptic digest of human KMT2D protein. A. CAD spectrum dominated by fragment ions corresponding to the low mass y-type ion and high mass b-type ions. B. ETD spectrum containing 22 of 41 possible c- and z-type product ions. C. Due to the large size of KMT2D (~553 kDa), the in vitro kinase were also performed using recombinant AKT and KMT2D (1222-1819) fragment containing the S1331 phosphorylation site immunoprecipitated from 293T as a substrate. D. Isogenic MCF10A cells expressing wild type (WT) or an activating mutation (H1047R) of PIK3CA were subjected to western blot with the indicated antibodies. E-G. Western blots of whole cell lysates of ER+ breast cancer cell lines, T47D, ZR751 and CAMA1 with the indicated antibodies. H. Western blot of T47D cell lysates blotted with pKMT2D (S1331) antibody or pKMT2D antibody pre-incubated for 2 h with KMT2D S1331 phosphospecific peptide. I. Proposed model: Upon activation of PI3K pathway, activated AKT phosphorylates KMT2D at S1331. Phosphorylation of KMT2D attenuates its activity, leading to loss of H3K4me1/2 and loss of binding of FOXA1-PBX1-ER transcriptional network and target gene expression off (left). Inhibition of the PI3Kα pathway by BYL719 inhibits AKT, leading to an increase of KMT2D activity and H3K4me1/2 methylation that facilitates the recruitment of FOXA1-PBX1 to allow subsequent binding of ER TF and target gene expression on (right).

5. DETAILED DESCRIPTION

For clarity, and not by way of limitation, the detailed description of the invention is divided into the following subsections:
(i) definitions;
(ii) KMT2D
(iii) KMT2D inhibitors;
(iv) PI3Kα inhibitors;
(v) pharmaceutical compositions;
(vi) methods of use; and
(vii) kits.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the formulations and methods of the invention and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, a "protein" or "polypeptide" refers to a molecule comprising at least one amino acid residue.

The terms "homology" or "homologous thereto," as used herein, refer to the degree of homology between nucleic acid or amino acid sequences as determined using methods known in the art, for example, but not limited to, software such as BLAST or FASTA.

"Inhibitor" as used herein, refers to a compound or molecule (e.g., small molecule, peptide, peptidomimetic, natural compound, siRNA, anti-sense nucleic acid, aptamer, or antibody) that interferes with (e.g., reduces, prevents, decreases, suppresses, eliminates or blocks) the signaling function of a protein or pathway. An inhibitor can be any compound or molecule that changes any activity of a named protein (signaling molecule, any molecule involved with the named signaling molecule or a named associated molecule), such as KMT2D, or interferes with the interaction of a named protein, e.g., KMT2D, with signaling partners. Inhibitors also include molecules that indirectly regulate the biological activity of a named protein, e.g., KMT2D, by intercepting upstream signaling molecules.

The terms "inhibiting," "eliminating," "decreasing," "reducing" or "preventing," or any variation of these terms, referred to herein, includes any measurable decrease or complete inhibition to achieve a desired result.

As used herein, the term "contacting" cancer cells (or a tumor) with a compound or molecule (e.g., one or more inhibitors, activators and/or inducers) refers to placing the compound in a location that will allow it to touch the cell (or the tumor). The contacting may be accomplished using any suitable methods. For example, contacting can be accomplished by adding the compound to a collection of cells, e.g., contained with a tube or dish. Contacting may also be accomplished by adding the compound to a culture medium comprising the cells. Contacting may also be accomplished by administering a compound to a subject that has one or more cancer cells, even where the site of administration is distant from the location of the cancer cell(s), provided that the compound would reasonably be expected access to the cancer cell(s), for example, by circulation through blood, lymph or extracellular fluid.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "treating" or "treatment" (and grammatical variations thereof such as "treat") refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder. In certain embodiments, "treatment" can refer to a decrease in the severity of complications, symptoms and/or cancer or tumor growth. For example, and not by way of limitation, the decrease can be a 10%, 20%, 30%, 40%, 50%, 60%, 70%, 80%, 90%, 95%, 98% or 99% decrease in severity of complications, symptoms and/or cancer or tumor growth, for example relative to a comparable control subject not receiving the treatment. In certain embodiments, "treatment" can also mean prolonging survival of a subject as compared to expected survival if treatment is not received.

An "effective amount" (or "therapeutically effective amount") is an amount sufficient to affect a beneficial or desired clinical result upon treatment. In certain embodiments, a therapeutically effective amount refers to an amount that is able to achieve one or more of an anti-cancer effect, prolongation of survival and/or prolongation of period until relapse. For example, and not by way of limitation, a therapeutically effective amount can be an amount of a compound (e.g., inhibitor) that produces an "anti-cancer effect." A therapeutically effective amount can be administered to a subject in one or more doses. The therapeutically effective amount is generally determined by the physician on a case-by-case basis and is within the skill of one in the art. Several factors are typically taken into account when determining an appropriate dosage to achieve a therapeutically effective amount. These factors include age, sex and weight of the subject, the condition being treated, the severity of the condition and the form and effective concentration of the cells administered.

An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a patient diagnosed with cancer.

An "anti-cancer agent," as used herein, can be any molecule, compound, chemical or composition that has an anti-cancer effect. Anti-cancer agents include, but are not limited to, chemotherapeutic agents, radiotherapeutic agents, cytokines, anti-angiogenic agents, apoptosis-inducing agents, anti-cancer antibodies and/or agents which promote the activity of the immune system including, but not limited to, cytokines such as but not limited to interleukin 2, interferon, anti-CTLA4 antibody, anti-PD-1 antibody and/or anti-PD-L1 antibody. In certain embodiments, an anti-cancer agent can be a PI3K inhibitor, e.g., a PI3Kα inhibitor.

5.2 KMT2D

Myeloid/lymphoid or mixed-lineage leukemia protein 2 is denoted herein as KMT2D herein. KMT2D is encoded by the Histone-lysine N-methyltransferase 2D (KMT2D) gene. In certain embodiments, KMT2D can be referred to as MLL2 or MLL4.

In a specific, non-limiting embodiment, KMT2D may be a human KMT2D protein having an amino acid sequence as set forth in NCBI/UniProtKB Accession No. NP_003473.3 or an amino acid sequence at least about 95 percent or at least about 98 percent homologous thereto.

In certain embodiments, KMT2D may be a mouse KMT2D protein having an amino acid sequence as set forth in NCBI/UniProtKB Accession No. NP_001028448.3 or an amino acid sequence at least about 95 percent or at least about 98 percent homologous thereto.

In certain embodiments, KMT2D may be a rat KMT2D protein having an amino acid sequence as set forth in NCBI/UniProtKB Accession No. XP_008764081.1 or an amino acid sequence at least about 95 percent or at least about 98 percent homologous thereto.

In certain embodiments, a nucleic acid encoding a KMT2D protein of the present invention can comprise a nucleic acid sequence as set forth in NCBI/UniProtKB Accession No. NM_003482.3 or a nucleic acid sequence at least about 95 percent or at least about 98 percent homologous thereto.

5.3 KMT2D Inhibitors

Non-limiting examples of KMT2D inhibitors include compounds, molecules, chemicals, polypeptides and proteins that inhibit and/or reduce the expression, function and/or activity of KMT2D. In certain embodiments, a KMT2D inhibitor prevents, reduces and/or eliminates the histone methyltransferase activity of KMT2D. For example, and not by way of limitation, a KMT2D inhibitor interacts with the SET domain of KMT2D to prevent, reduce and/or eliminate the histone methyltransferase activity of KMT2D.

Non-limiting examples of KMT2D inhibitors include ribozymes, antisense oligonucleotides, shRNA molecules and siRNA molecules that specifically inhibit and/or reduce the expression or activity of KMT2D. One non-limiting example of a KMT2D inhibitor comprises an antisense, shRNA or siRNA nucleic acid sequence homologous to at least a portion of a KMT2D nucleic acid sequence, wherein the homology of the portion relative to the KMT2D sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Antisense, shRNA or siRNA molecules may comprise DNA or atypical or non-naturally occurring residues, for example, but not limited to, phosphorothioate residues. Non-limiting examples of shRNAs that can be used to specifically inhibit and/or reduce the expression or activity of KMT2D are disclosed in Table 1.

The RNA molecules of the invention can be expressed from a vector or produced chemically or synthetically. Methods for selecting an appropriate dsRNA or dsRNA-encoding vector are well known in the art for genes whose sequence is known (e.g., see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and PCT Patent Application Nos. WO 2001/036646, WO 1999/032619 and WO 2001/068836, the contents of which are incorporated by reference herein in their entireties).

In certain non-limiting embodiments, the KMT2D inhibitor can be an antibody or antibody fragment that can partially or completely block KMT2D signaling and/or activity.

In certain embodiments, a KMT2D inhibitor of the present invention can be conjugated to a modality that specifically targets cancer cells. For example, and not by way of limitation, a KMT2D inhibitor can be conjugated to an antibody or antibody fragment and/or peptide, e.g., that recognizes an epitope on the surface of a cancer cell. In certain embodiments, the modality can be a nanoparticle that specifically targets cancer cells, e.g., by the presence of a targeting moiety conjugated to the nanoparticle.

In certain non-limiting embodiments, inhibition and/or reduction of KMT2D expression, function and/or activity can be obtained by targeted degradation of KMT2D (see, e.g., Winter et al. Science. 348(6241):1376-1381 (2015), the contents of which are hereby incorporated by reference). For example, and not by way of limitation, a KMT2D inhibitor and/or a compound that interacts with KMT2D can be conjugated to a phthalimide, e.g., a derivatized phthalimide. Non-limiting examples of derivatized phthalimides include thalidomide, lenalidomide and pomalidomide. In certain embodiments, a KMT2D inhibitor and/or a compound that interacts with KMT2D can be conjugated to a phthalimide, e.g., a derivatized phthalimide, to promote targeted degradation of KMT2D, e.g., by using the Cereblon E3 ubiquitin ligase complex.

5.4 PI3Kα Inhibitors

Non-limiting examples of PI3Kα inhibitors include compounds, molecules, chemicals, polypeptides and proteins that inhibit and/or reduce the expression, function and/or activity of PI3Kα. Additional non-limiting examples of PI3Kα inhibitors include ATP-competitive inhibitors of PI3Kα. In particular non-limiting embodiments, the PI3Kα inhibitor is derived from imidazopyridine or 2-aminothiazole compounds. Further non-limiting examples include BYL719, INK-1114, INK-1117, SRX2523, LY294002, PIK-75, PKI-587, A66, CH5132799, GDC-0032 (taselisib) and GDC-0077. In certain embodiments, the PI3Kα inhibitor is BYL719.

Further non-limiting examples of PI3Kα inhibitors are disclosed in Hayakawa et al., Bioorg. Med. Chem. (2007) 15(17):5837-5844 and PCT Patent Application Nos. WO 2013/049581 and WO 2012/052745, the contents of which are herein incorporated by reference in their entireties.

In particular non-limiting embodiments, PI3Kα inhibitors include ribozymes, antisense oligonucleotides, shRNA molecules and siRNA molecules that specifically inhibit and/or reduce the expression or activity of PI3Kα. One non-limiting example of a PI3Kα inhibitor comprises an antisense, shRNA, or siRNA nucleic acid sequence homologous to at least a portion of a PI3Kα nucleic acid sequence, e.g., the nucleic acid sequence of a PI3Kα subunit such as PIK3CA, wherein the homology of the portion relative to the PI3Kα sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Antisense, shRNA, or siRNA molecules may comprise DNA or atypical or non-naturally occurring residues, for example, but not limited to, phosphorothioate residues. As disclosed above, the RNA molecules of the invention can be expressed from a vector or produced chemically or synthetically. Methods for selecting an appropriate dsRNA or dsRNA-encoding vector are also disclosed above.

5.5 Pharmaceutical Formulations

In certain non-limiting embodiments, the present invention provides for pharmaceutical formulations of the KMT2D inhibitors disclosed above in section 5.3 for therapeutic use. In certain embodiments, the pharmaceutical formulation comprises a KMT2D inhibitor and a pharmaceutically acceptable carrier. In certain embodiments, a pharmaceutical formulation of the present invention can include a KMT2D inhibitor and/or a compound that interacts with KMT2D that is conjugated to a phthalimide compound (or a derivative thereof) as described herein. In certain embodiments, a pharmaceutical formulation of the present invention can include a KMT2D inhibitor, a PI3Kα inhibitor and a pharmaceutically acceptable carrier. In certain embodiments, pharmaceutical formulations described herein can include a KMT2D inhibitor and/or an anti-cancer agent at the doses disclosed in section 5.6 below.

"Pharmaceutically acceptable carrier," as used herein, includes any carrier which does not interfere with the effectiveness of the biological activity of the active ingredients, e.g., inhibitors, and that is not toxic to the patient to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers can include gels, bioadsorbable matrix materials, implantation elements containing the inhibitor and/or any other suitable vehicle, delivery or dispensing means or material. Such carriers can be formulated by conventional methods and can be administered to the subject. In certain embodiments, the pharmaceutical acceptable carrier can include buffers such as phosphate, citrate, and other organic acids; antioxidants including ascorbic acid and methionine; preservatives (such as, but not limited to, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). In certain embodiments, a suitable pharmaceutically acceptable carrier can include one or more of water, saline, phosphate buffered saline, dextrose, glycerol, ethanol or combinations thereof.

In certain embodiments, the methods and formulations of the present invention can be used for reducing, inhibiting, preventing or reversing cancer and/or tumor growth. Standard methods for intracellular delivery can be used (e.g., delivery via liposome). Such methods are well known to those of ordinary skill in the art. Therapeutic administration of an inhibitor intracellularly can also be accomplished using gene therapy, e.g., by using shRNAs. The route of administration eventually chosen will depend upon a number of factors and can be ascertained by one skilled in the art.

In certain non-limiting embodiments, the pharmaceutical formulations of the present invention can be formulated using pharmaceutically acceptable carriers well known in the art that are suitable for oral administration. Such carriers enable the pharmaceutical compositions to be formulated as tablets, pills, capsules, liquids, gels, syrups, slurries, suspensions and the like, for oral or nasal ingestion by a patient to be treated. In certain embodiments, the pharmaceutical formulation can be a solid dosage form. In certain embodiments, the tablet can be an immediate release tablet. Alternatively or additionally, the tablet can be an extended or controlled release tablet. In certain embodiments, the solid dosage can include both an immediate release portion and an extended or controlled release portion.

In certain embodiments, the pharmaceutical formulations of the present invention can be formulated using pharmaceutically acceptable carriers well known in the art that are suitable for parenteral administration. The terms "parenteral administration" and "administered parenterally," as used herein, refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. For example, and not by way of limitation, formulations of the present invention can be administered to the patient intravenously in a pharmaceutically acceptable carrier such as physiological saline. In certain embodiments, the present invention provides a parenteral formulation comprising a KMT2D inhibitor and/or a PI3Kα inhibitor.

In certain embodiments, the pharmaceutical formulations suitable for use in the present invention can include formulations where the active ingredients, e.g., KMT2D inhibitors, are contained in a therapeutically effective amount. The therapeutically effective amount of an active ingredient can vary depending on the active ingredient, e.g., KMT2D inhibitor, formulation used, the cancer and its severity, and the age, weight, etc., of the subject to be treated. In certain embodiments, a patient can receive a therapeutically effective amount of a KMT2D inhibitor in single or multiple administrations of one or more formulations, which can depend on the dosage and frequency as required and tolerated by the patient.

In certain non-limiting embodiments, the KMT2D inhibitors described above can be used alone or in combination with one or more anti-cancer agents. "In combination with," as used herein, means that a KMT2D inhibitor and the one or more anti-cancer agents are administered to a subject as part of a treatment regimen or plan. In certain embodiments, being used in combination does not require that the inhibitor and the one or more anti-cancer agents are physically combined prior to administration or that they be administered over the same time frame. Accordingly, a second anti-cancer agent may be administered prior to, concurrently with, or subsequent to, administration of one or more doses of a KMT2D inhibitor.

In certain non-limiting embodiments, the KMT2D inhibitor can be used in combination with a PI3Kα inhibitor, as disclosed above. For example, and not by way of limitation, a pharmaceutical formulation of the present invention can include one or more KMT2D inhibitors and one or more PI3Kα inhibitors. For example, and not by way of limitation, a pharmaceutical formulation of the present invention can include a therapeutically effective amount of one or more KMT2D inhibitors and a therapeutically effective amount of one or more PI3Kα inhibitors. Non-limiting examples of PI3Kα inhibitors include BYL719, INK-1114, INK-1117, SRX2523, LY294002, PIK-75, PKI-587, A66, CH5132799 and GDC-0032 (taselisib). In certain embodiments, the PI3Kα inhibitor is BYL719.

In certain embodiments, where an inhibitor is used in combination with an anti-cancer agent, the amount of each may in some instances be less than a therapeutically effective amount for that agent taken singly, but when both are used therapeutically effectiveness is achieved.

5.6 Methods of Use

The present invention relates to methods for treating cancer by inhibiting KMT2D activity, expression and/or function. Accordingly, the present invention provides methods of treating cancer by reducing and/or inhibiting KMT2D activity by the administration of a KMT2D inhibitor, disclosed above. Non-limiting examples of KMT2D inhibitors, and pharmaceutical formulations thereof, are disclosed in sections 5.3 and 5.5 above. As such, the present invention relates to methods for inhibiting and/or reducing KMT2D expression, functionality and/or activity to produce an anti-cancer effect in a subject.

In certain embodiments, the cancer is breast cancer. In certain embodiments, the cancer is ER+ breast cancer.

In certain embodiments, the cancer is a cancer, which, upon treating the cancer, or a cell of the cancer, with PI3Kα inhibitor, exhibits an increase in KMT2D activity in response to PI3Kα inhibitor treatment.

In certain non-limiting embodiments, the present invention provides for a method of treating and/or reducing the severity, growth and/or presence of cancer or a tumor, by administering to a subject in need thereof, an effective amount of a formulation comprising a KMT2D inhibitor, as described herein. In certain embodiments, subjects in need of such treatment or formulations include subjects that have a cancer that comprises cells exhibiting elevated KMT2D activity as compared to a control sample. For example, and not by way of limitation, one or more cells of a cancer to be treated using the methods and formulations of the present invention can exhibit about 1.5 fold, about 2.0 fold, about 2.5 fold, about 3.0 fold, about 3.5 fold, about 4.0 fold, about 4.5 fold or greater KMT2D activity, e.g., H3K4 methyltransferase activity, compared to a control sample. In certain embodiments, the control sample can be a sample, e.g., one or more healthy cells, adjacent to the cancer in the subject or a sample, e.g., one or more cells, from a healthy subject.

In certain non-limiting embodiments, the present invention provides for a method of treating a subject having a cancer comprising administering, to the subject, a therapeutically effective amount of a KMT2D inhibitor that promotes an anti-cancer effect. In certain embodiments, the cancer can be breast cancer.

In certain embodiments, the present invention provides a method of producing an anti-cancer effect in a subject having a cancer comprising administering, to the subject, a therapeutically effective amount of a KMT2D inhibitor, disclosed above, e.g., to inhibit, reduce, prevent and/or eliminate KMT2D expression, functionality and/or activity.

In certain non-limiting embodiments, the present invention further provides for a method of treating a subject having a cancer that includes the targeted degradation of KMT2D to produce an anti-cancer effect in the subject. For example, and not by way of limitation, the present invention provides for a method of treating a subject having a cancer that comprises administering, to the subject, a therapeutically effective amount of a KMT2D inhibitor and/or a compound that interacts with KMT2D that is conjugated to a phthalimide compound (or a derivative thereof) to produce an anti-cancer effect in the subject. In certain embodiments, the cancer can be breast cancer.

The present invention further provides a method of preventing, minimizing and/or reducing the growth of a tumor comprising administering to the tumor and/or contacting the tumor with a therapeutically effective amount of a KMT2D inhibitor.

The present invention provides a method of preventing, minimizing and/or reducing the growth and/or proliferation of a cancer cell comprising administering to the cancer cell and/or contacting the cancer cell with a therapeutically effective amount of a KMT2D inhibitor.

In certain non-limiting embodiments, the present invention provides for methods of treating and/or inhibiting the progression of cancer and/or tumor growth, in a subject in need thereof by administering a KMT2D inhibitor in an amount effective to decrease, eliminate and/or reduce the activity of KMT2D.

In certain embodiments, the present invention provides a method for lengthening the period of survival of a subject having a cancer comprising administering, to the subject, a therapeutically effective amount of a KMT2D inhibitor, disclosed above. In certain embodiments, the cancer is breast cancer. In certain embodiments, the period of survival of a subject having cancer can be lengthened by about 1 month, about 2 months, about 4 months, about 6 months, about 8 months, about 10 months, about 12 months, about 14 months, about 18 months, about 20 months, about 2 years, about 3 years, about 5 years or more using the disclosed methods.

In certain embodiments, the methods of the present invention can include determining whether one or more cells of the cancer exhibit enhanced KMT2D activity. For example, and not by way of limitation, a method for detecting whether the activity of KMT2D has increased can include determining the level of methylation of H3K4 compared to a control sample, as disclosed herein. In certain embodiments, chromatin immunoprecipitation (ChIP) can be used to determine if the levels of H3K4 methylation are enhanced compared to a control sample. Non-limiting examples of methods for analyzing H3K4 methylated chromatin are disclosed in U.S. Patent Publication No. 2014/0148355, the contents of which are hereby incorporated by reference herein in its entirety.

In certain embodiments, the methods of the present invention can further comprise administering to the subject a second anti-cancer agent, as described above. For example, and not by way of limitation, the methods of the present invention can comprise administering, to the subject, a therapeutically effective amount of a KMT2D inhibitor and a therapeutically effective amount of a PI3Kα inhibitor. In certain embodiments, the KMT2D inhibitor and the PI3Kα inhibitor can be administered concomitantly. Alternatively or additionally, the PI3Kα inhibitor can be administered prior to the KMT2D inhibitor or the PI3Kα inhibitor can be administered after the KMT2D inhibitor. In other non-limiting embodiments, a regimen may comprise alternately administering a PI3Kα inhibitor and a KMT2D inhibitor (or a KMT2D inhibitor and a PI3Kα inhibitor, depending on which agent is used first).

In a specific non-limiting embodiment, a KMT2D inhibitor can be administered at an amount of about 1 mg/kg to about 100 mg/kg, e.g., by administration of a pharmaceutical formulation disclosed herein. For example, and not by way of limitation, a KMT2D inhibitor can be administered at an amount of about 1 mg/kg to about 95 mg/kg, about 1 mg/kg to about 90 mg/kg, about 1 mg/kg to about 85 mg/kg, about 1 mg/kg to about 80 mg/kg, about 1 mg/kg to about 75 mg/kg, about 1 mg/kg to about 70 mg/kg, about 1 mg/kg to about 65 mg/kg, about 1 mg/kg to about 60 mg/kg, about 1 mg/kg to about 55 mg/kg, about 1 mg/kg to about 50 mg/kg, about 1 mg/kg to about 45 mg/kg, about 1 mg/kg to about 40 mg/kg, about 1 mg/kg to about 35 mg/kg, about 1 mg/kg to about 30 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 100 mg/kg, about 10 mg/kg to about 100 mg/kg, about 15 mg/kg to about 100 mg/kg, about 20 mg/kg to about 100 mg/kg, about 25 mg/kg to about 100 mg/kg, about 30 mg/kg to about 100 mg/kg, about 35 mg/kg to about 100 mg/kg, about 40 mg/kg to about 100 mg/kg, about 45 mg/kg to about 100 mg/kg, about 50 mg/kg to about 100 mg/kg, about 55 mg/kg to about 100 mg/kg, about 60 mg/kg to about 100 mg/kg, about 65 mg/kg to about 100 mg/kg, about 70 mg/kg to about 100 mg/kg, about 75 mg/kg to about 100 mg/kg, about 80 mg/kg to about 100 mg/kg, about 85 mg/kg to about 100 mg/kg, about 90 mg/kg to about 100 mg/kg or about 95 mg/kg to about 100 mg/kg.

In certain non-limiting embodiments, the KMT2D inhibitor can be administered at an amount of about 1 mg to about 500 mg, e.g., by administration of a pharmaceutical formulation disclosed herein that includes about 1 mg to about 500 mg of a KMT2D inhibitor. In certain embodiments, the KMT2D inhibitor can be administered at an amount of about 1 mg to about 200 mg. For example, and not by way of limitation, a KMT2D inhibitor can be administered at an amount of about 5 mg to about 200 mg, about 10 mg to about 200 mg, about 20 mg to about 200 mg, about 30 mg to about 200 mg, about 40 mg to about 200 mg, about 50 mg to about 200 mg, about 60 mg to about 200 mg, about 70 mg to about 200 mg, about 80 mg to about 200 mg, about 90 mg to about 200 mg, about 100 mg to about 200 mg, about 110 mg to about 200 mg, about 120 mg to about 200 mg, about 130 mg to about 200 mg, about 140 mg to about 200 mg, about 150 mg to about 200 mg, about 160 mg to about 200 mg, about 170 mg to about 200 mg, about 180 mg to about 200 mg, about 190 mg to about 200 mg, about 1 mg to about 190 mg, about 1 mg to about 180 mg, about 1 mg to about 170 mg, about 1 mg to about 160 mg, about 1 mg to about 150 mg, about 1 mg to about 140 mg, about 1 mg to about 130 mg, about 1 mg to about 120 mg, about 1 mg to about 110 mg, about 1 mg to about 100 mg, about 1 mg to about 90 mg, about 1 mg to about 80 mg, about 1 mg to about 70 mg, about 1 mg to about 60 mg, about 1 mg to about 50 mg, about 1 mg to about 40 mg, about 1 mg to about 30 mg, about 1 mg to about 20 mg, about 1 mg to about 10 mg or about 1 mg to about 5 mg.

In certain non-limiting embodiments, a KMT2D inhibitor may be administered to achieve a local concentration that inhibits cellular KMT2D activity by about 20%, about 25%, about 30%, about 35%, about 40%, about 45%, about 50%, about 55%, about 60% or more. For example, such concentration may be determined in cell culture.

In a specific non-limiting embodiment, an anti-cancer agent, e.g., a PI3Kα inhibitor, can be administered at an amount of about 1 nM to about 50 μM (see Reagan-Shaw et al., The FASEB J., Vol. 22: 659-661 (2008)), e.g., by administration of a pharmaceutical formulation disclosed herein. For example, and not by way of limitation, the anti-cancer agent can be administered at an amount of about 1 nM to about 45 μM, about 1 nM to about 40 μM, about 1 nM to about 35 μM, about 1 nM to about 30 μM, about 1 nM to about 25 μM, about 1 nM to about 20 μM, about 1 nM to about 15 μM, about 1 nM to about 10 μM, about 1 nM to about 5 μM, about 1 nM to about 1 μM, about 1 nM to about 100 nM, about 1 nM to about 90 nM, about 1 nM to about 80 nM, about 1 nM to about 70 nM, about 1 nM to about 60 nM, about 1 nM to about 50 nM, about 1 nM to about 40 nM, about 1 nM to about 30 nM, about 1 nM to about 20 nM, about 1 nM to about 10 nM, about 1 nM to about 5 nM, about 5 nM to about 50 μM, about 10 nM to about 50 μM, about 20 nM to about 50 μM, about 30 nM to about 50 μM, about 40 nM to about 50 μM, about 50 nM to about 50 μM, about 60 nM to about 50 μM, about 70 nM to about 50 μM, about 80 nM to about 50 μM, about 90 nM to about 50 μM, about 100 nM to about 50 μM, about 1 μM to about 50 μM, about 10 μM to about 50 μM, about 15 μM to about 50 μM, about 20 μM to about 50 μM, about 25 μM to about 50 μM, about 30 μM to about 50 μM, about 35 μM to about 50 μM, about 40 NM to about 50 μM or about 45 μM to about 50 μM.

In a specific non-limiting embodiment, an anti-cancer agent, e.g., a PI3Kα inhibitor, can be administered at an amount of about 0.1 mg/kg to about 500 mg/kg (see Reagan-Shaw et al., The FASEB J., Vol. 22: 659-661 (2008)), e.g., by administration of a pharmaceutical formulation disclosed herein. In certain embodiments, the anti-cancer agent can be administered at an amount of about 0.1 mg/kg to about 450 mg/kg, about 0.1 mg/kg to about 400 mg/kg, about 0.1 mg/kg to about 350 mg/kg, about 0.1 mg/kg to about 300 mg/kg, about 0.1 mg/kg to about 250 mg/kg, about 0.1 mg/kg to about 200 mg/kg, about 0.1 mg/kg to about 150 mg/kg, about 0.1 mg/kg to about 100 mg/kg, about 0.1 mg/kg to about 50 mg/kg, about 0.1 mg/kg to about 45 mg/kg, about 0.1 mg/kg to about 40 mg/kg, about 0.1 mg/kg to about 35 mg/kg, about 0.1 mg/kg to about 30 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 1 mg/kg, about 0.1 mg/kg to about 0.5 mg/kg, about 0.5 mg/kg to about 500 mg/kg, about 1 mg/kg to about 500 mg/kg, about 10 mg/kg to about 500 mg/kg, about 15 mg/kg to about 500 mg/kg, about 20 mg/kg to about 500 mg/kg, about 25 mg/kg to about 500 mg/kg, about 30 mg/kg to about 500 mg/kg, about 35 mg/kg to about 500 mg/kg, about 40 mg/kg to about 500 mg/kg, about 45 mg/kg to about 500 mg/kg, about 50 mg/kg to about 500 mg/kg, about 55 mg/kg to about 500 mg/kg, about 60 mg/kg to about 500 mg/kg, about 65 mg/kg to about 500 mg/kg, about 70 mg/kg to about 500 mg/kg, about 75 mg/kg to about 500 mg/kg, about 80 mg/kg to about 500 mg/kg, about 85 mg/kg to about 500 mg/kg, about 90 mg/kg to about 500 mg/kg, about 95 mg/kg to about 500 mg/kg, about 100 mg/kg to about 500 mg/kg, about 150 mg/kg to about 500 mg/kg, about 200 mg/kg to about 500 mg/kg, about 250 mg/kg to about 500 mg/kg, about 300 mg/kg to about 500 mg/kg, about 350 mg/kg to about 500 mg/kg, about 400 mg/kg to about 500 mg/kg or about 450 mg/kg to about 500 mg/kg. In a specific non-limiting embodiment, an anti-cancer agent can be administered at an amount of about 0.1 mg/kg to about 5 mg/kg, e.g., 2 mg/kg (see Reagan-Shaw et al., The FASEB J., Vol. 22: 659-661 (2008)).

In certain embodiments, the KMT2D inhibitors of the present invention can be administered once, twice, three, four, five or six times per week, or daily, for a period of at least one week, or at least two weeks, or at least one month, or at least two months, or at least three months, or at least four months, or at least five months, or at least six months, or at least seven months, or at least eight months, or at least nine months, or at least ten months, or at least eleven months or at least one year or until a desired therapeutic effect is achieved. In certain embodiments, the second anti-cancer agent of the present invention can be administered once, twice, three, four, five, or six times per week, or daily, for a period of at least one week, or at least two weeks, or at least one month, or at least two months, or at least three months, or at least four months, or ar least five months, or at least six months, or at least seven months, or at least eight months, or at least nine months, or at least ten months, or at least eleven months, or at least one year or until a desired therapeutic effect is achieved. In certain embodiments, the inhibitors and/or anti-cancer agents of the presently disclosed subject matter can be administered one or more times per day. For example, and not by way of limitation, the KMT2D inhibitors and/or anti-cancer agents of the present invention can be administered once, twice, three, four, five or more times a day. Any of the foregoing regiments may be repeated as necessary to achieve a desired therapeutic effect. In certain non-limiting embodiments, the desired therapeutic effect is remission of the cancer where there is no presently detectible evidence of disease.

A KMT2D inhibitor and/or an anti-cancer agent, disclosed herein, can be administered to the subject using standard methods of administration. In certain embodiments, the inhibitor can be administered to the subject orally or parenterally. For example, and not by way of limitation, the route of administration can be intravenous, intraarterial, intrathecal, intraperitoneal, intramuscular, subcutaneous, topical, intradermal, intranasal, vaginal, rectal, route, locally to the cancer, or combinations thereof. In certain embodiments, the inhibitor can be administered to the patient from a source implanted in the patient. In certain embodiments, administration of the inhibitor can occur by continuous infusion over a selected period of time.

5.7 Kits

The present invention further provides kits that can be used to practice the invention. For example, and not by way of limitation, a kit of the present invention can comprise a KMT2D inhibitor or a pharmaceutical formulation comprising a therapeutically effective amount of a KMT2D inhibitor. In certain embodiments, a kit of the present invention can further include a second anti-cancer agent, e.g., within the same container as the KMT2D inhibitor (or formulation thereof) or within a second container. For example, and not by way of limitation, the anti-cancer agent can be a PI3Kα inhibitor such as, but not limited to, BYL719.

In certain non-limiting embodiments, the present invention provides for a kit for use in treating cancer in a subject comprising a KMT2D inhibitor or a pharmaceutical formulation thereof, a second anti-cancer agent and instructions for use. For example, and not by way of limitation, the instructions can indicate that the KMT2D inhibitor and the second anti-cancer can be administered together or separately. In certain embodiments, the kit is for use in treating breast cancer.

In certain non-limiting embodiments, the present invention provides for a kit that includes a vial comprising a KMT2D inhibitor, e.g., a therapeutically effective amount of a KMT2D inhibitor, and/or a vial comprising a second anti-cancer agent, e.g., a therapeutically effective amount of a second anti-cancer agent, with instructions to use any combination of the components of the one or more vials together or separately for treating cancer. For example, and not by way of limitation, the instructions can include a description of a KMT2D inhibitor and/or a second anti-cancer agent, and, optionally, other components present in the kit. In certain embodiments, the instructions can describe methods for administration of the components of the kit, including methods for determining the proper state of the subject, the proper dosage amount and the proper administration method for administering one or more of the KMT2D inhibitor and/or other anti-cancer agent. Instructions can also include guidance for monitoring the subject over the duration of the treatment time. In certain embodiments, the kit may further comprise one or more vials comprising additional KMT2D inhibitors and/or other anti-cancer agents. In certain embodiments, a kit of the present invention comprises a vial that includes a KMT2D inhibitor and an anti-cancer agent.

In certain non-limiting embodiments, the present invention provides for a kit of this disclosure further including one or more of the following: devices and additional reagents, and components, such as tubes, containers, cartridges, and syringes for performing the methods disclosed below.

The following example is offered to more fully illustrate the disclosure, but is not to be construed as limiting the scope thereof.

6. EXAMPLE 1: KMT2D-DEPENDENT REGULATION OF ESTROGEN RECEPTOR ACTIVATION BY THE PI3K PATHWAY IN BREAST CANCER

6.1 Methods

Human Cell Lines, Transient Transfection Assays and Lentiviral Production.

All cell lines were obtained from ATCC and used at low passages. T47D cells were maintained in RPMI 1640 with 10% FBS, 1% L-glutamine and 1% penicillin-streptomycin. MCF7 cells were maintained in DF-12 DMEM Dulbecco medium with 10% FBS, 1% L-glutamine and 1% penicillin-streptomycin. HEK 293T cells were maintained in DMEM Dulbecco medium supplemented with 10% FBS, 1% L-glutamine and 1% penicillin-streptomycin. For RNA analysis, MCF7 cells or T47D cells underwent hormonal starvation. MCF7 and T47D were cultured for 3 days in phenol-red-free DF12 DMEM and phenol-red-free RPMI respectively, media was supplemented with 5% charcoal/dextran-treated FCS. Cells were induced with E2 (100 nM), BYL719 (1 µM) or vehicle (DMSO) for 24 hours.

When indicated, MCF7 or T47D cells were transduced with lentiviruses expressing empty vector (pLKO. 1) or an shRNA against KMT2D (pLKO. 1) (disclosed in Table 1) or shRNA against FOXA1, shFOXA1 #1 TRCN0000014882; shFOXA1 #2: TRCN0000014880; or shRNA against PBX1, shPBX1 #1: TRCN0000020390; shPBX1 #2: TRCN0000020391). When indicated, MCF7 cells were transduced with pTRIPZ vectors (TRE-RFP-miR30/shRNA-UBC-IRES-PURO) targeting PBX1 or FOXA1 knockdown upon doxycycline administration. When indicated, MCF7 cells were transduced with LT3REPIR (pRRL) vector (T3G-dsRED-mirE/shRNA-PGK-PURO-IRES-rtTA3) targeting KMT2D knockdown upon doxycycline administration. For lentiviral production, 293T cells were transfected with pCMV-VSVG, pCMV-dR8.2 and the plasmid of interest using lipofectamine 3000 according to the manufacture's protocol.

TABLE 1

KMT2D shRNAs

| Name | Sequence |
|---|---|
| shKMT2D #1:<br>TRCN0000013140 | CCGGCCTCGCCTCAAGAAATGGAAACTCGAGTTTC<br>CATTTCTTGAGGCGAGGTTTTT (SEQ ID<br>NO: 33) |
| shKMT2D #2:<br>TRCN0000013139 | CCGGCCTGAATTGAACAACAGTCTTCTCGAGAAGA<br>CTGTTGTTCAATTCAGGTTTTT (SEQ ID<br>NO: 34) |
| shKMT2D #3:<br>TRCN0000013138 | CCGGCCCACCTGAATCATCACCTTTCTCGAGAAAG<br>GTGATGATTCAGGTGGGTTTTT (SEQ ID<br>NO: 35) |

For transient transfections, HEK 293T cells were transfected with equimolar amounts (1 μg/ml) of wild-type and mutant pCMV-HA-KMT2D plasmids using the polyethylenimine method, following published protocols. Cells were collected 48 h after transfection and used for protein extraction or for isolation of semipurified HA-KMT2D proteins, as described below. MCF7 cells were transiently transfected with pCMV3-FLAG-KDM1 plasmid using Lipofectamine 3000 according to the manufacture's protocol.

Reagents and Cell Viability.

BYL719 was obtained from the Stand Up to Cancer (SU2C) pharmacy. BYL719 was dissolved in DMSO for in vitro experiments. The MTT assay was used to measure cell viability. Briefly, 5000 cells were seeded in 96 well plates, treated with BYL719 for 5 days and assayed using 0.25% MTT (Sigma) and 50 mM sodium succinate (Sigma) for 3 hours. After the formazan crystals were dissolved with DMSO, the absorbance was measured at 570 nm of wavelength. Doxycycline was purchased from Sigma.

Immunoblot, Immunoprecipitation and In Vitro Kinase Assay.

For immunoblot analysis, RIPA buffer supplemented with protease and phosphatase inhibitors (Roche) was used to lyse the cell pellets. The supernatant was collected by centrifugation for 10 min at 12,000 g. Protein lysates were separated using SDS-PAGE gradient gels (4-12%). The KMT2D probed gels were separated using low percentage SDS-PAGE gradient gels (3-8%). The gels were transferred to a PVDF membrane for 2 hours at 70 V. The membranes were probed using specific antibodies. Actin, pAKT (S473), H3 and phospho-RXRXX(S/T) were from Cell Signaling Technology (CST). The rabbit KMT2D and pKMT2D (S1331) were generated by Eurogentec (third bleed) and affinity purified against GRARLKSTASSIC (SEQ ID NO: 36) and GRARLKS(PO$_3$H2)TASSIC (SEQ ID NO: 36) peptides respectively. Histone H3 (mono methyl K4) (ab8895), histone H3 (di methyl K4) (ab7766), FOXA1 (ab5089) were from Abcam. PBX1 antibodies (H00005087-MO1) were from Abnova and ER alpha antibodies were (sc-543) from Santa Cruz.

For immunoprecipitation assays, cells were transfected with appropriate plasmids and 48 h post transfection, cells were lysed using NP-40 buffer (150 mM NaCl, 10 mM Tris pH 8, 1% NP-40, 10% glycerol). Lysates were incubated at 4° C. overnight with EZview™ RED Anti-HA agarose beads (Sigma) or protein G agarose beads (Thermo Scientific) followed by the appropriate antibody. The immunocomplexed were washed three times using NP-40 buffer. For in vitro kinase assay, immunoprecipitated V5-KMT2D (1222-1819) or HA-KMT2D (full length) were used as a substrate in a reaction with recombinant His-AKT (MRC-PPU Reagents DU1850) and ATP (Signalchem) in kinase buffer (25 mM MOPS, pH 7.2, 12.5 mM 0-glycerolphosphate, 25 mM MgCl$_2$, 5 mM EGTA, 2 mM EDTA and 0.25 mM DTT) at 30° C. for 30 minutes.

In Vitro Histone Methyltransferase (KMT) Assay.

Partially purified HA-KMT2D wild-type and mutant derivative proteins (S1331A and S1331D) were obtained from transfecting the appropriate plasmids into HEK 293T cells, followed by immunoprecipitation assays using HA beads. Briefly, the cells were lysed in IP buffer (50 mM Tris, pH 7.5, 250 mM NaCl, 1% TritonX-100, 1 mM EDTA), the supernatants were collected by centrifugation for 10 minutes at 12,000 g and the lysates were incubated overnight with EZview Red Anti-HA Affinity beads (Sigma-Aldrich) at 4° C. After three washes, the beads were eluted in BC100 buffer (20 mM Tris pH 7.5, 10% Glycerol, 0.2 mM EDTA, 1% TritonX-100, 100 mM NaCl) containing 100 μM HA peptide (Sigma-Aldrich). Vivaspin Sample Concentrators (GE Healthcare, 10 kDa cutoff) were used to concentrate the samples at 12,000 g for 10 min. KMT2D protein amounts were quantified by Coomassie staining and western blot analysis using rat monoclonal antibodies to HA (clone 3F10, Roche).

KMT activity against an artificial H3 peptide was measured by the EpiQuik Histone Methyltransferase Activity-Inhibition Assay Kit (H3K4) (Epigentek), following the manufacturer's protocol. Relative activity was calculated as the fold change in OD$_{450nm}$ over the mean reading of control IgG samples. Experiments were performed in triplicate and repeated independently three times.

Plasmids and Generation of pCMV-HA-KMT2D Mutant Expression Constructs.

The pCMV-HA-KMT2D plasmid was a gift from Dr. Laura Pasqualucci from Columbia University. The mutants KMT2D (S1331A and S1331D) were generated from the wild-type pCMV-HA-KMT2D using PCR-based site-directed mutagenesis approach. All plasmids were verified for integrity by diagnostic restriction enzyme digestions followed by Sanger sequencing of the full-length KMT2D coding sequence. pCMV3-FLAG-KDM1 plasmid was obtained from Sino Biological Inc.

Animal Studies.

Animals were maintained based on the institutional guidelines of Memorial Sloan Kettering Cancer Center (Protocol number 12-10-019). 6×10$^6$ MCF7 cells in 1:1 DF12 media/Matrigel (Corning) were injected subcutaneously into four to six week old female athymic Foxn1$^{nu}$ mice. Mice were randomized when tumors reached ~130 mm$^2$ of volume. 5 mice, 10 tumors were then treated with BYL719 (25 mg×kg$^{-1}$ in 0.5%) in carboxymethylcellulose (Sigma) daily for the indicated times. Tumors were collected at the end of the experiments, two to four hours after the last treatment.

Mass Spectrometry.

Proteins were resolved using SDS-polyacrylamide gel electrophoresis, stained with SimplyBlue SafeStain (Life Technologies) and gel sections excised with in situ trypsin digestion of polypeptides in each gel slice were performed as described[33]. The tryptic peptides were desalted using a 2 µl bed volume of Poros 50 R2 (Applied Biosystems) reversed-phase beads packed in Eppendorf gel-loading tips and eluted with 40% acetonitrile. The purified peptides were diluted to 0.1% formic acid and each gel section was analyzed separately by microcapillary liquid chromatography with tandem mass spectrometry using the NanoAcquity (Waters) with a 100-µm-inner-diameter×10-cm-length C18 column (1.7 µm BEH130, Waters) configured with a 180-µm×2-cm trap column coupled to an OrbiElite mass spectrometer (Thermo Fisher Scientific) scanning 300-1650 m/z at 120000 resolution with AGC set at $1 \times 10^6$. Peptides were eluted with a linear gradient of 0-50% acetonitrile (0.1% formic acid) in water (0.1% formic acid) over 90 min with a flow rate of 300 nL/min. Key parameters for the data dependent MS were top 10 DDA, AGC $10^4$ and CID ms/ms collected in the linear ion trap. Key parameters for the targeted MS/MS were isolation width 2 and for ETD anion target $5 \times 10^5$, reaction time 150 ms, with product ions collected in the ion trap using enhanced resolution scan mode from 50 to 2000 m/z.

Initial protein/peptide identifications from the LC-MS/MS data were performed using the Mascot search engine (Matrix Science, version 2.3.02; www.matrixscience.com) with the Uniprot human protein database (downloaded on Feb. 23, 2015). The search parameters were as follows: (i) two missed cleavage tryptic sites were allowed; (ii) precursor ion mass tolerance 10 ppm; (iii) fragment ion mass tolerance 0.8 Da; and (iv) variable protein modifications were allowed for methionine oxidation, deamidated (NQ), protein N-terminal acetylation, phosphoserine, phosphothreonine and phosphotyrosine.

RNA Extraction, cDNA Synthesis, Quantitative Real-Time PCR.

Total RNA was extracted from patient biopsies tissue using TRIzol (Life Technologies) and treated with DNAse before cDNA synthesis. cDNA synthesis was performed using the Bio-Rad cDNA synthesis kit according to the manufacturer's instructions. RNA was isolated from cells using the QIAGEN RNeasy kit. The qPCR SYBR green mix (Applied Biosystems) was used to amplify specific cDNA fragments with the oligonucleotides listed in Extended figure using the ViiA™ Real Time PCR system (Applied Biosystems). The data were analyzed by the change-in-threshold ($2^{-\Delta\Delta CT}$) method using Actin or GAPDH as a housekeeping genes to obtain relative RNA expression. Primers used for mRNA expression were:

GREB1:
(SEQ ID NO: 1)
5'-GTGGTAGCCGAGTGGACAAT-3';

(SEQ ID NO: 2)
5'-ATTTGTTTCCAGCCCTCCTT-3'

PGR:
(SEQ ID NO: 3)
5'-GGCATGGTCCTTGGAGGT-3';

(SEQ ID NO: 4)
5'-CCACTGGCTGTGGGAGAG-3' cFOS:
(SEQ ID NO: 5)
5'-TGATGACCTGGGCTTCCCAG-3';

(SEQ ID NO: 6)
5'-CAAAGGGCTCGGTCTTCAGC-3'

EGR3:
(SEQ ID NO: 7)
5'-GGAGCAAATGAAATGTTGGTG-3';

(SEQ ID NO: 8)
5'AGGAAAACCTATGGGGAATG-3'

ERBB3:
(SEQ ID NO: 9)
5'-CTGATCACCGGCCTCAAT-3';

(SEQ ID NO: 10)
5'GGAAGACATTGAGCTTCTCTGG-3'

SERPINA1:
(SEQ ID NO: 11)
5'-AATGGGGCTGACCTCTCC-3';

(SEQ ID NO: 12)
5'-GTCAGCACAGCCTTATGCAC-3'

MYC:
(SEQ ID NO: 13)
5'-GCTGCTTAGACGCTGGATTT-3';

(SEQ ID NO: 14)
5'-TAACGTTGAGGGGCATCG-3'

ACTIN:
(SEQ ID NO: 15)
5'-CGTCTTCCCCTCCATCGT-3';

(SEQ ID NO: 16)
5'-GAAGGTGTGGTGCCAGATTT-3'

GAPDH:
(SEQ ID NO: 17)
5'-ACAGTCAGCCGCATCTTCTT-3';

(SEQ ID NO: 18)
5'-ACGACCAAATCCGTTGACTC-3'

Chromatin Immunoprecipitation (ChIP).

Cells were crosslinked with 1% paraformaldehyde added directly to the culture medium to a final concentration of 1% and incubated at room temperature for 15 minutes. The crosslinked cells were quenched with ice-cold glycine for 5 minutes, washed with PBS and collected. The cells were then lysed with SDS lysis buffer (10 ml of 1% SDS, 10 mM EDTA, 50 mM Tris-HCl, pH 8.1) containing protease and phosphatase inhibitors for 15 minutes prior to sonication. Cells were sonicated in 10-s pulses for a total of 10 min. The sheared chromatin was diluted with ChIP Dilution buffer (0.01% SDS, 1.1% Triton X-100, 1.2 mM EDTA, 16.7 mM Tris-HCl, pH 8.1, 167 mM NaCl) and incubated overnight with Protein G Dynabeads (Thermo Fisher Scientific), which were pre-incubated with specific antibodies. ChIP antibodies to the following proteins were used: FOXA1 (ab5089) Abcam, PBX1 (H00005087-MO1) from Abnova, ER alpha (sc-543) from Santa Cruz and rabbit KMT2D homemade antibody which was generated by Eurogentec (third bleed) and affinity purified against GRARLKSTAS-SIC peptide (SEQ ID NO: 36). The immune-complexes were washed twice with low salt wash buffer (0.1% SDS, 1% Triton X-100, 2 mM EDTA, 20 mM Tris-HCl, pH 8.1, 150 mM NaCl), high salt was buffer (0.1% SDS, 1% Triton X-100, 2 mM EDTA, 20 mM Tris-HCl, pH 8.1, 500 mM NaCl), LiCl wash buffer (0.25M LiCl, 1% NP40, 1% doexycholate, 1 mM EDTA, 10 mM Tris-HCl, pH 8.1) and 1× TE buffer (10 mM Tris-HCl, 1 mM EDTA pH 8.0). The complexes were eluted with elution buffer (1% SDS, 0.1M NaHCO$_3$). The eluates were reverse crosslinked at 65° C. for 4 hours by adding 20 μM of 5M NaCl following by proteinase K treatment for one hour at 4° C. The DNA was purified using Qiagen PCR quick. Primers used for ChIP-qPCR analysis are:

```
GREB1:
                                (SEQ ID NO: 19)
5'-GAAGGGCAGAGCTGATAACG-3';

(SEQ ID NO: 20)
5'-GACCCAGTTGCCACACTTTT-3'

PGR:
                                (SEQ ID NO: 21)
5'-AGGGAGGAGAAAGTGGGTGT-3';

(SEQ ID NO: 22)
5'-GGAGAACTCCCCGAGTTAGG-3' cFOS:
                                (SEQ ID NO: 23)
5'-TGATGACCTGGGCTTCCCAG-3';

(SEQ ID NO: 24)
5'-TGATGACCTGGGCTTCCCAG-3'

EGR3:
                                (SEQ ID NO: 25)
5'-ACCTCCAAGAGGGAGAGGAG-3';

(SEQ ID NO: 26)
5'-GGACCAAGCAGTCATTTGGT-3'

SERPINA1:
                                (SEQ ID NO: 27)
5'-AGGTATGGGCACAAGACCTG-3';

(SEQ ID NO: 28)
5'-TCAGGGGAAAATTGTCTTCG-3'

MYC:
                                (SEQ ID NO: 29)
5'-GTCAGCCAATCTTCGCACTT-3';

(SEQ ID NO: 30)
5'-TGCCAGAGGAAGCTACTGGT-3'

ACTIN:
                                (SEQ ID NO: 31)
5'-TGTTCCAGGCTCTGTTCCTC-3';

(SEQ ID NO: 32)
5'-AGAAAAGAACGCAGGCAGAA-3'
```

ChIP-Seq Library Preparation, Illumina Sequencing, ChIP-Seq Analysis.

Paired ends 36 bp sequencing was performed at the Genomics Core of Memorial Sloan Kettering Cancer Center using HiSeq (Illumina). Reads were first processed with Trimmomatic to remove the adaptor sequences and bases with quality scores below 20 and reads with less than 30 remaining bases were discarded[34]. Trimmed reads were then aligned to hg19 human genome with the bowtie aligner[35]. ER and FOXA1 peaks were called using MACS2 using p value cut-off 0.01[36]. To find a set of peaks that are reproducible across the two biological replicates of a given cell condition, the per-replicate P-value of each peak was calculated using only the read count at the peak from the individual replicate and estimated the irreproducible discovery rate (IDR)[37] from the two sets of P-values that the replicates produced. Only peaks with an IDR of 0.05 or less were kept for downstream analyses.

Differentially accessible peaks from combined atlas were identified with DESeq[38] by counting all read ends overlapping peaks in each condition. DESeq was run with a fold-change threshold of 1.5 and FDR <0.1. The distribution of the peaks around the TSS was calculated using the ChIPpeakAnno package[39]. DNA motif analysis was performed with the HOMER[40].

Transposase-Accessible Chromatin Using Sequencing (ATAC-Seq) and Analysis.

Starting from fastq files containing ATAC-seq paired-end reads, sequencing adaptors were removed using Trimmomatic[34]. Trimmed reads were mapped to the hg19 human genome using Bowtie2[35] allowing at most 1 seed mismatch and keeping only uniquely aligned reads. Duplicates were removed using Picard (http://picard.sourceforge.net). For peak-calling the read start sites were adjusted (reads aligning to the +/−strand were offset by +4 bp/−5 bp, respectively) to represent the center of the transposon binding-event, as described in Buenrostro et al.[21] For each samples, ATAC-seq was run on two biological replicates. Peak calling was performed on each condition individually by pooling reads from biological replicates and using MACS2[36] with a permissive P-value threshold (−p 1e−2). To find a set of peaks that are reproducible across the two biological replicates of a given cell condition, we calculated the per-replicate P-value of each peak using only the read count at the peak from the individual replicate and estimated the irreproducible discovery rate (IDR)[37] from the two sets of P-values that the replicates produced. Only peaks with an IDR of 0.05 or less were kept for downstream analyses. This procedure generated a set of reproducible accessible sites for each condition. To create a single atlas of accessible sites for the before and after treatment, peaks from two conditions were merged if their overlap was 75% or more; if they overlapped by 25% or less, two peaks were kept separate by removing the overlapping region. In this way an atlas of 52070 accessible sites (or peaks) that were reproducible in at least one condition were created. To link site accessibility to regulation of gene expression, we associated each peak to its nearest gene in the human genome using ChIPpeakAnno package[39]. Differentially accessible peaks from this atlas were identified with edgeR[38] by counting all read ends overlapping peaks in each condition. edgeR was run with default settings, a fold-change threshold of 2 and FDR <0.01. The Bioconductor[41] and deepTools[42] were used for visualization.

Statistical Analyses.

Two way t-tests were performed using GraphPad Prism (GraphPad Software), P-values are indicated in the respective graphs. All cellular experiments were repeated at least three times. The in vivo experiments contained 10 tumors for each treatment arm and the sample size was chosen to reflect a difference in means of 20% with a power of 90%. Before the commencement of the in vivo experiments, animals were measured and randomized in groups with similar average tumor volume. Bioinformatics statistics are indicated in the respective method descriptions.

6.2 Results

The PI3K pathway is essential for growth, proliferation, survival and metabolism of cancer cells[1-3]. Upon activation by receptor tyrosine kinases and other extracellular stimuli, PI3K catalyzes the production of phosphatidylinositol-3,4,5-trisphosphate (PIP3) that recruits to the cellular membrane a subset of proteins containing pleckstrin-homology (PH) domains, including the serine-threonine kinase AKT. Activation of AKT results in the phosphorylation of a myriad of substrates that are involved in cell cycle and apoptosis, among other cellular processes[4]. The importance of the PI3K pathway in breast cancer is highlighted by the high frequency of activating somatic mutations of PIK3CA, the gene encoding the alpha isoform of the catalytic subunit (p110α)[5,6]. In addition, other activating mutations are also found in genes of the same pathway such as ERBB2 and AKT1[5,6]. As a result, clinical studies with PI3Kα inhibitors have been initiated and have shown anti-tumor activity in PIK3CA-mutant, ER-positive breast cancer[7,8]. As with other targeted agents, however, a number of mechanisms of resistance have emerged that could potentially limit their efficacy[9,10]. In this regard, a highly uniform adaptive tumor response to PI3K inhibitors that is characterized by an increase in ER-dependent transcription has been observed, which mediates therapeutic resistance and can be reversed by the addition of anti-ER therapies[11]. These findings have led to pilot clinical studies of PI3Kα inhibitors with anti-ER agents that have shown high response rates and prolonged clinical benefit, even in tumors refractory to ER therapies[12-14]. These findings have triggered the launch of two phase III registration clinical studies testing PI3Kα inhibitors in combination with the anti-ER agent fulvestrant that are currently enrolling patients with advanced PIK3CA-mutant ER-positive breast cancer[15,16]. This clinical approach, however, is somewhat empirical as the mechanisms by which tumor cells exposed to PI3Kα inhibitors activate ER signaling are not well understood. ER is a hallmark of luminal breast cancers that acts as a master regulator to control transcriptional repertoires aimed to favour tumor growth and survival[17]. Binding of ER to the estrogen responsive elements (EREs) is accompanied by the association with other cooperating TFs that are essential for the function of this intricate network[17-19]. In this Example, the chromatin-based epigenetic regulation that results in the activation of ER function upon PI3Kα blockage has been investigated.

Figure 1A:
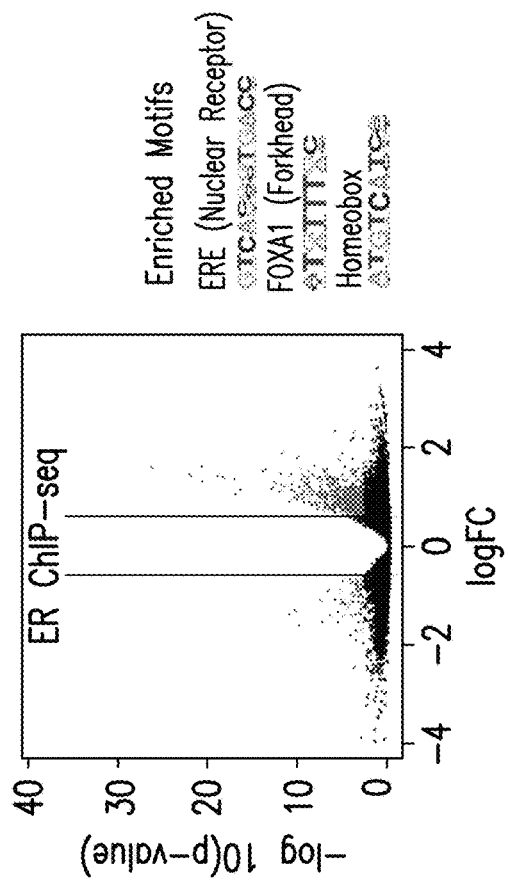

The transcription factors FOXA1 and PBX1 are required for enhanced ER-dependent transcription upon PI3K inhibition. PI3Kα inhibition increases ER transcriptional output in breast cancer cells[11]. ER activity requires co-operating TFs that determine and guide ER function[18,19]. Therefore, in order to understand the cis-regulatory elements and cofactors involved in the ER-dependent transcription upon treatment with a PI3Kα inhibitor (namely BYL719)[20], ER chromatin immunoprecipitation followed by high throughput sequencing (ChIP-seq) experiments were performed. PI3K inhibition induced differential ER binding, as demonstrated by gained or lost ER binding events (FIG. 1A). Motif analysis in the ER gained binding sites predicted, as expected, the ERE motif to be highly enriched. Forkhead Box A1 (FOXA1) and a homeobox class motif were also enriched, suggesting the presence of these cooperative factors at the ER binding sites. FOXA1 is an important pioneer TF required for ER-chromatin interactions[18]. On the other hand, PBX1 (Pre-B-cell leukaemia homeobox 1), a member of the homeobox family and also a known ER regulator[19], was most likely associated with the homeobox class motif found in our analysis.

Figure 1C:
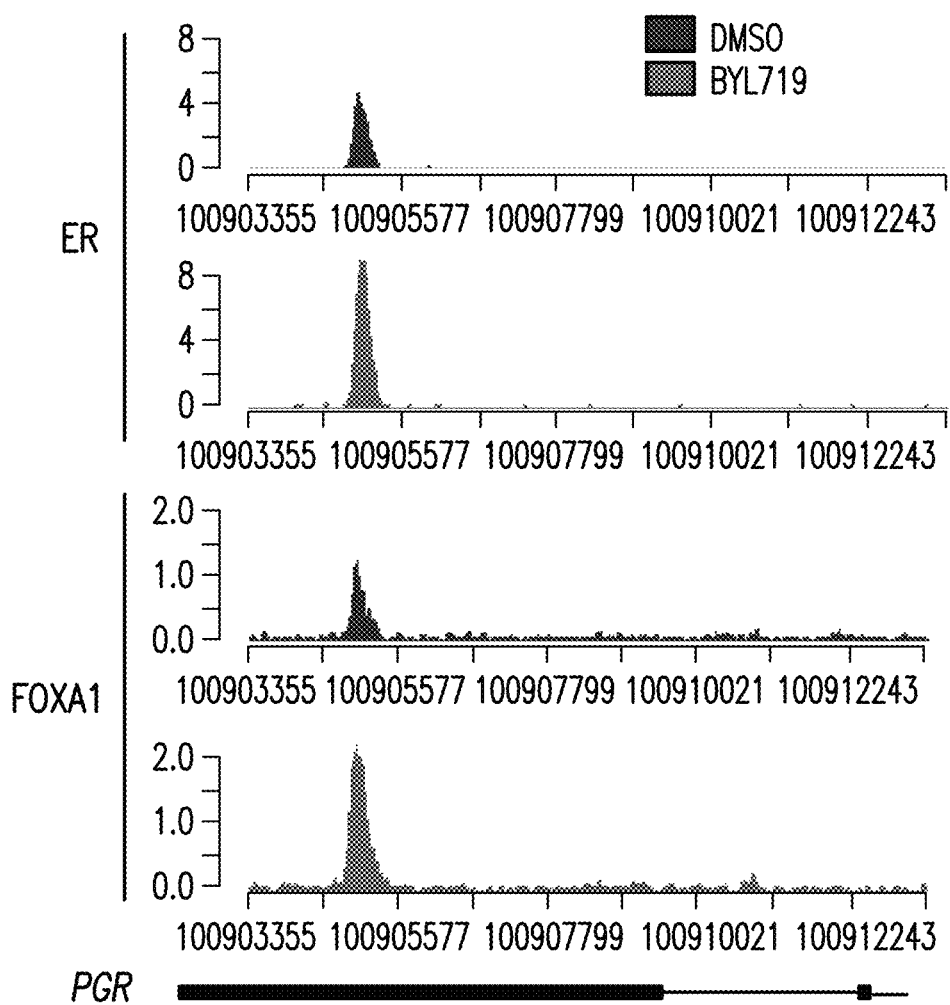

FOXA1 ChIP-seq was further performed, which also revealed a differential binding profile of FOXA1 upon PI3K inhibition. A nuclear receptor and a homeobox class motif, suggestive of ER and PBX1, respectively, were among the most enriched motifs within the FOXA1 enhanced binding regions (FIG. 1B). An increased co-occupancy of ER and FOXA1 was also observed upon BYL719 treatment at specific target loci (FIG. 1C and FIG. 5A). Hence, it was hypothesized that PI3K inhibition enhances the binding of the FOXA1-PBX1-ER regulatory network to chromatin, indicating that FOXA1 or PBX1 may be involved in the ER activation upon PI3K blockage.

Figure 1D:
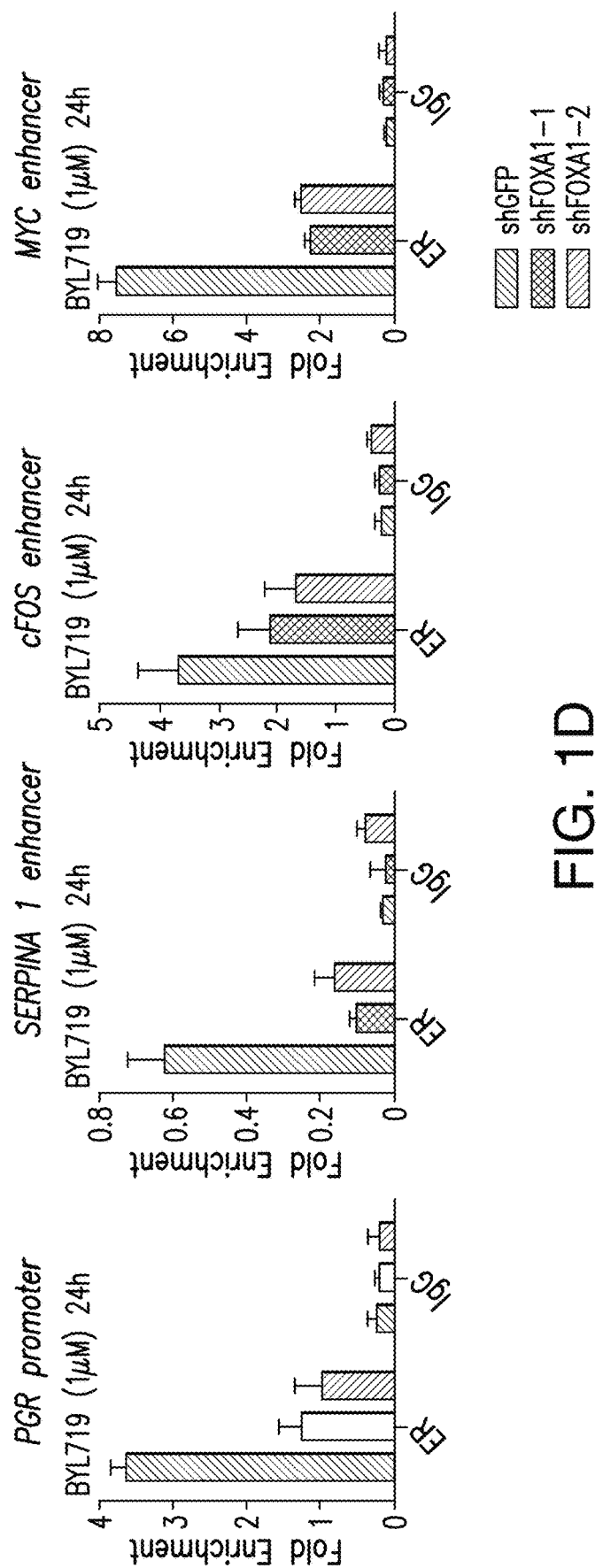
Figure 1E:
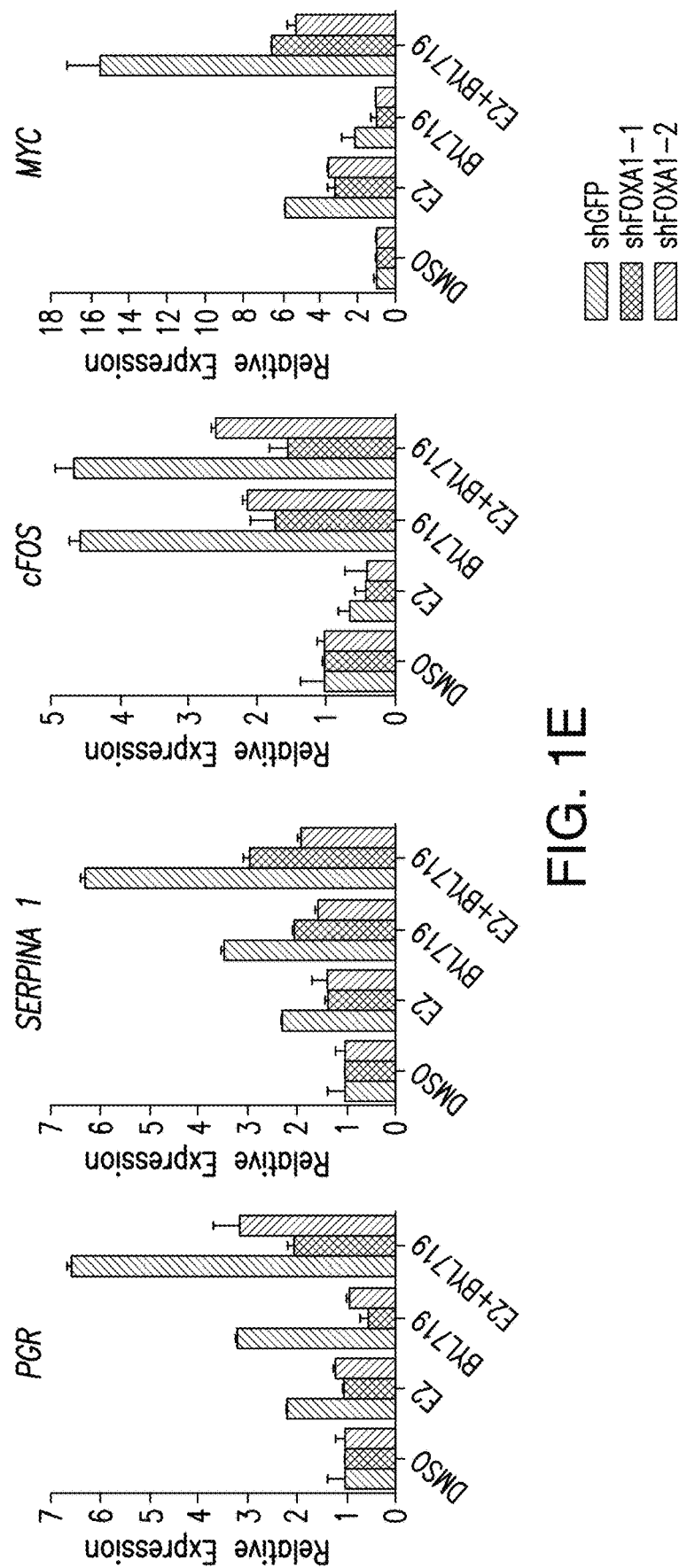
Figure 6C:
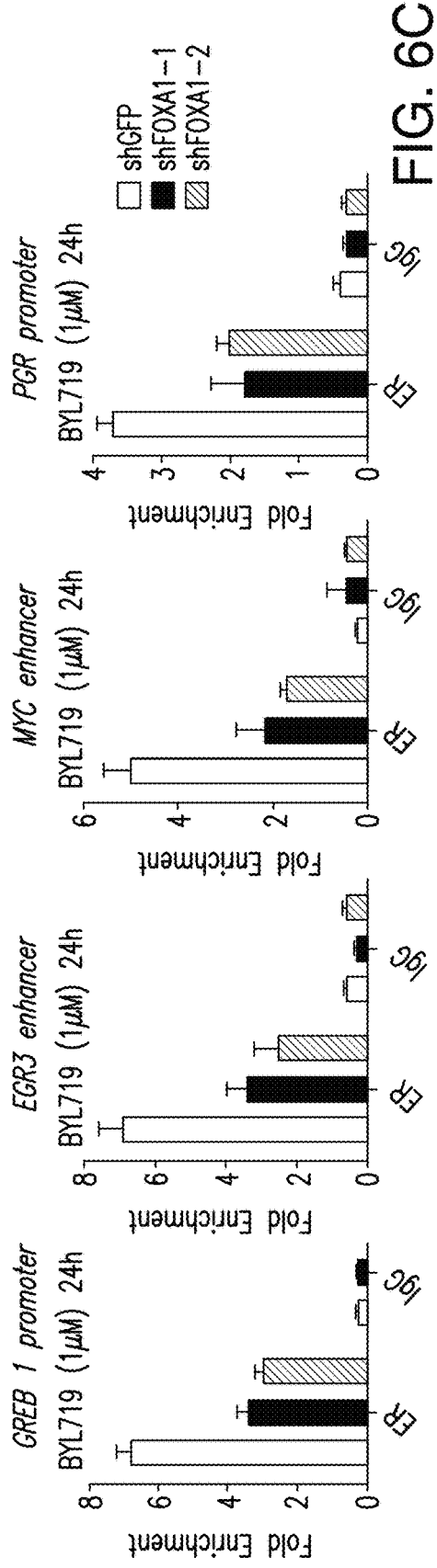
Figure 6D:
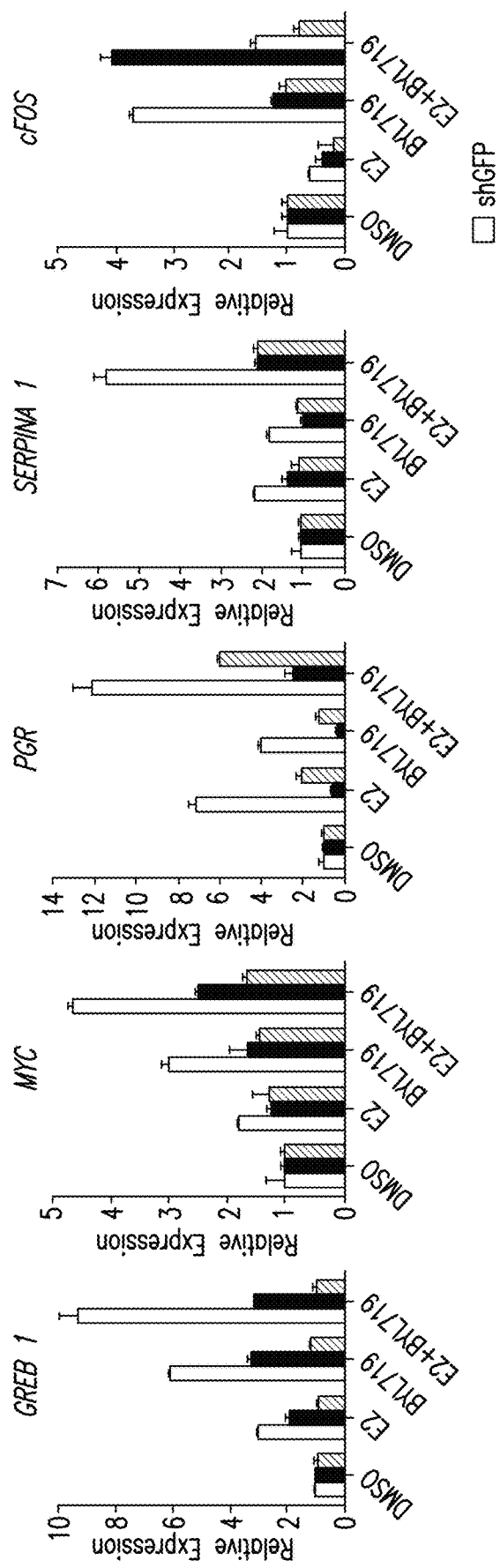
Figure 7A:
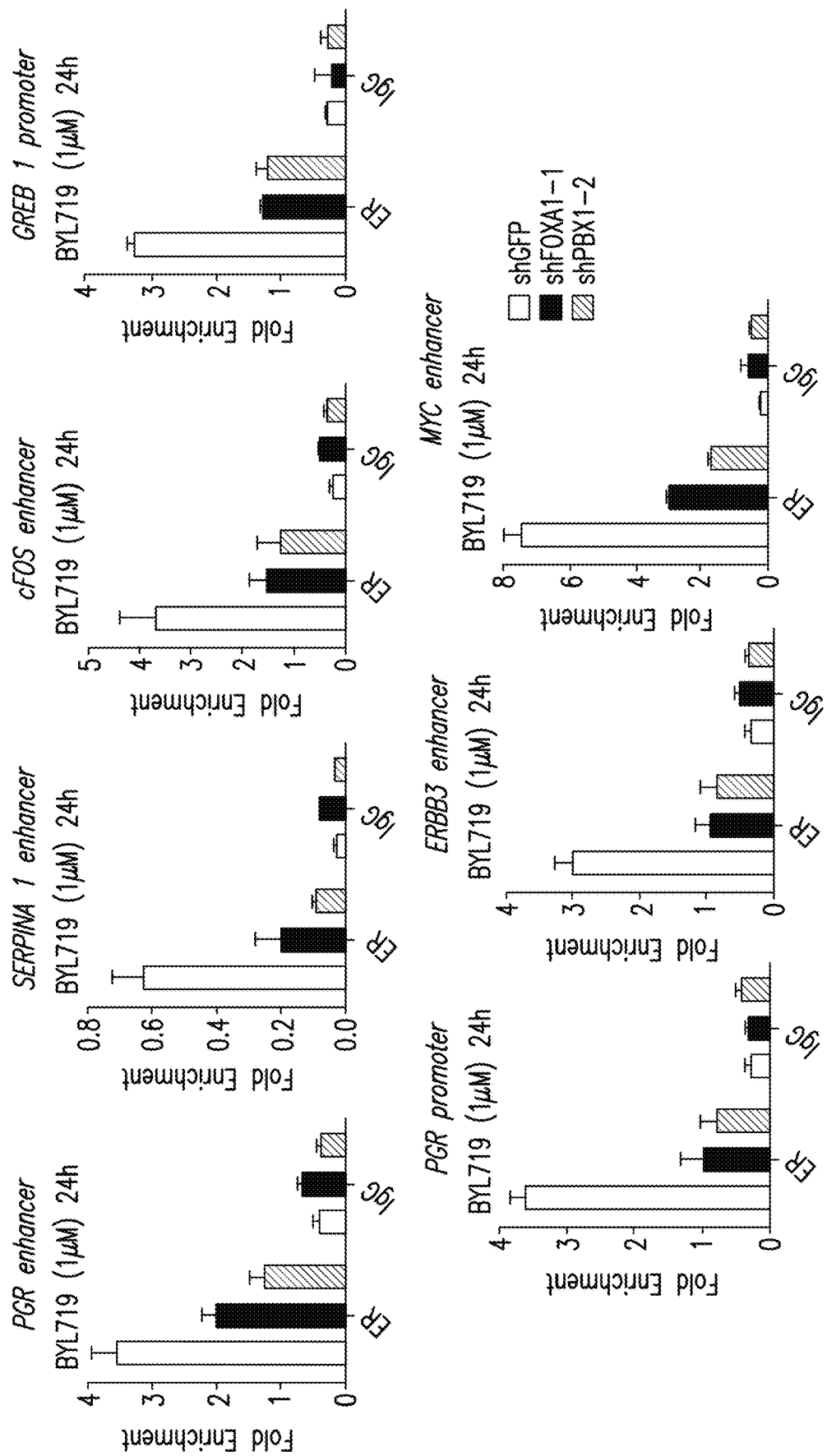
Figure 7B:
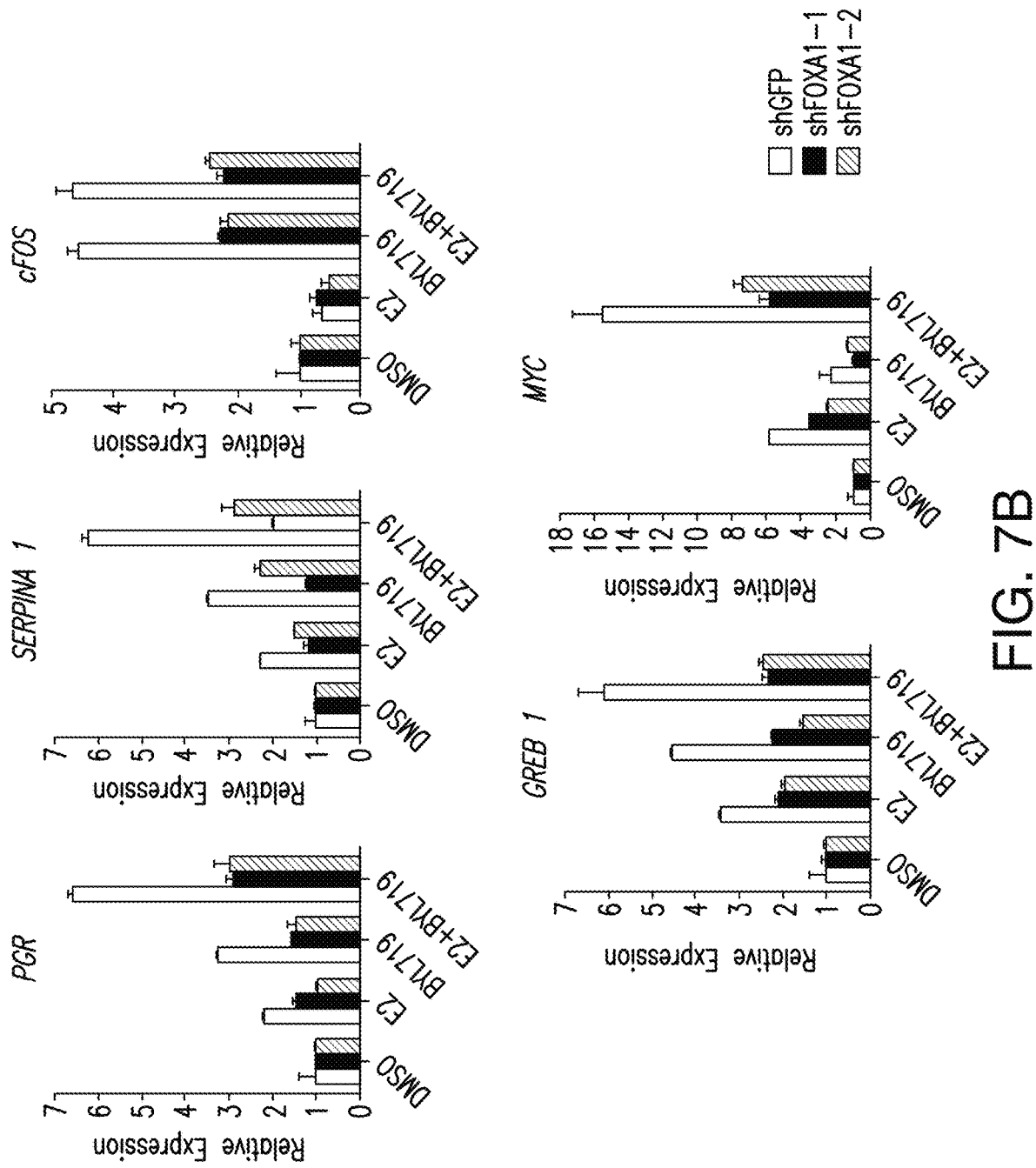
Figure 7C:
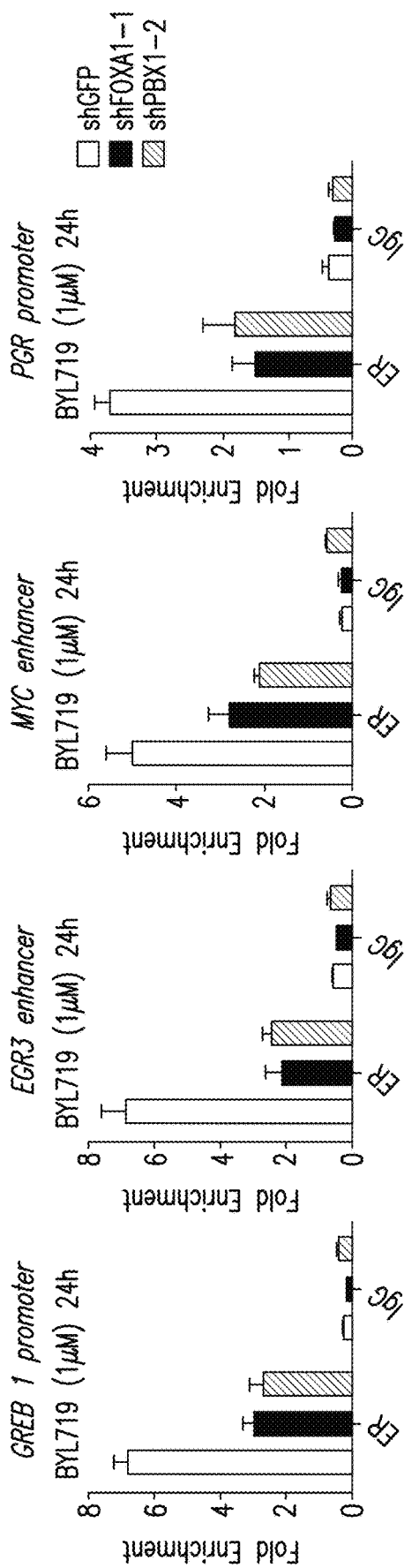
Figure 7D:
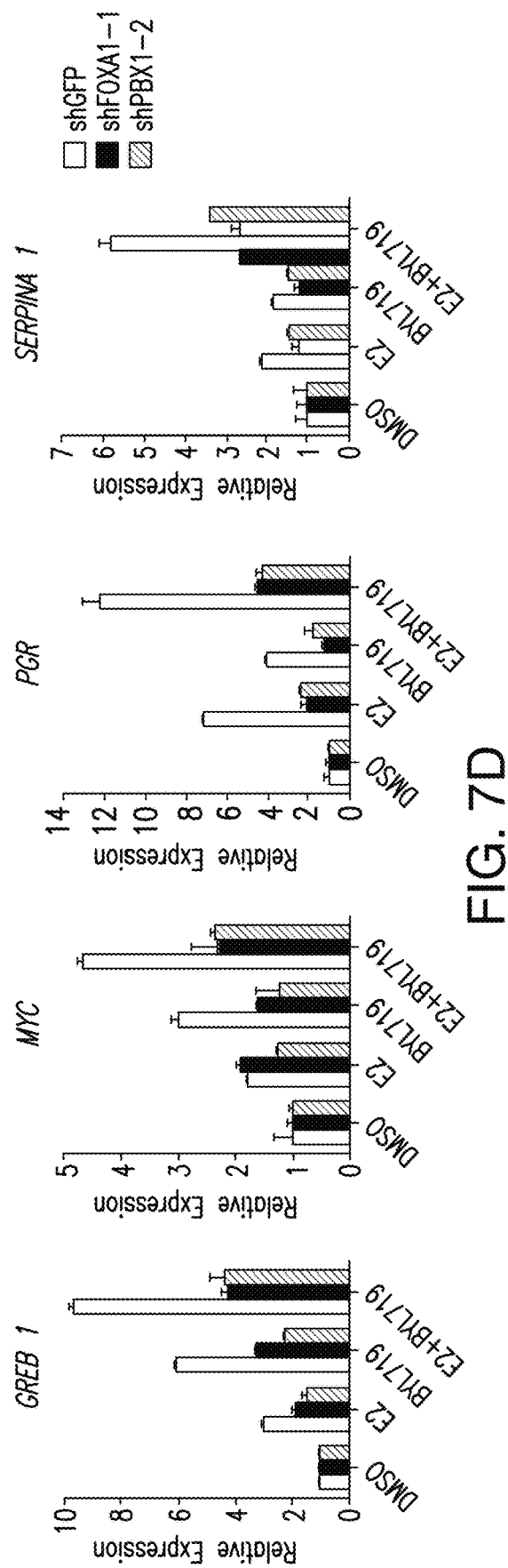

To assess the cooperative role that FOXA1 and PBX1 play on the activation of ER-mediated gene expression at the chromatin level, ChIP-qPCR was performed to examine the binding of these TFs to the enhancers or promoters of canonical ER target genes. The binding of ER, FOXA1 and PBX1 was significantly enhanced upon PI3K inhibition (FIG. 5B, C). The impact FOXA1 or PBX1 played on enhancing ER-chromatin interactions upon treatment with BYL719 was then determined. FOXA1 was silenced and ChIP-qPCR was performed to examine the recruitment of ER upon PI3K inhibition. The silencing of FOXA1 in T47D cells resulted in a marked loss of ER binding for the indicated ER target genes and prevented BYL719-mediated induction of ER-target genes (FIG. 1D, E and FIG. 6A, B). These findings were also recapitulated in MCF7, another ER-positive cell line (FIG. 6C, D).

In a similar fashion, PBX1 was silenced and the effects on ER occupancy and target gene expression upon PI3K inhibition was measured. PBX1 knockdown, much alike to FOXA1 silencing, resulted in a marked loss of ER occupancy upon PI3K inhibition that significantly affected the expression of ER target genes (FIG. 7). Without being limited to a particular theory, these findings suggest that both FOXA1 and PBX1 TFs are required, for ER function in the context of PI3K therapeutic inhibition, as evident by the loss of binding and activity of ER upon FOXA1 and PBX1 knockdown.

Figure 1H:
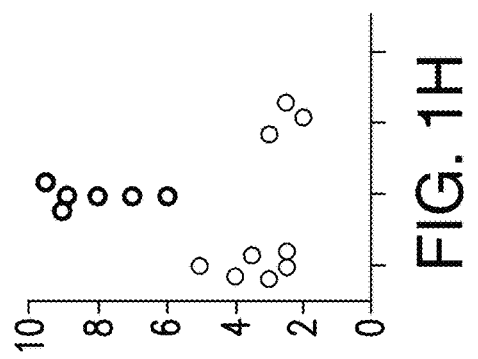
Figure 1G:
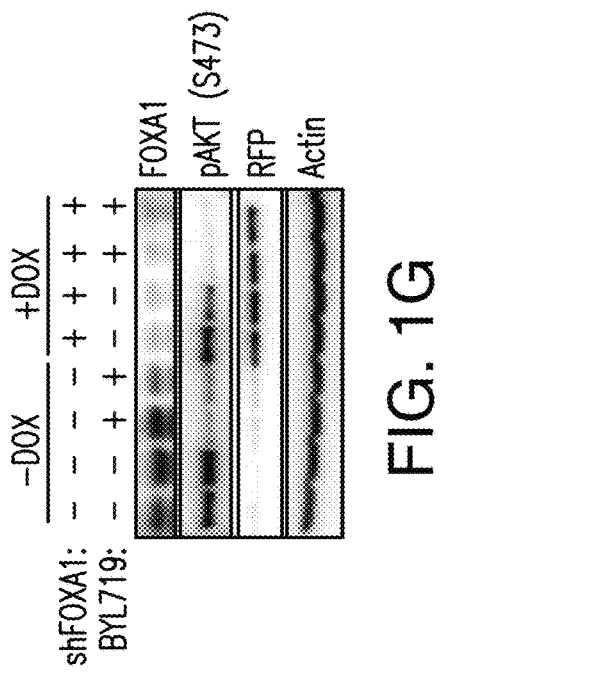
Figure 1F:
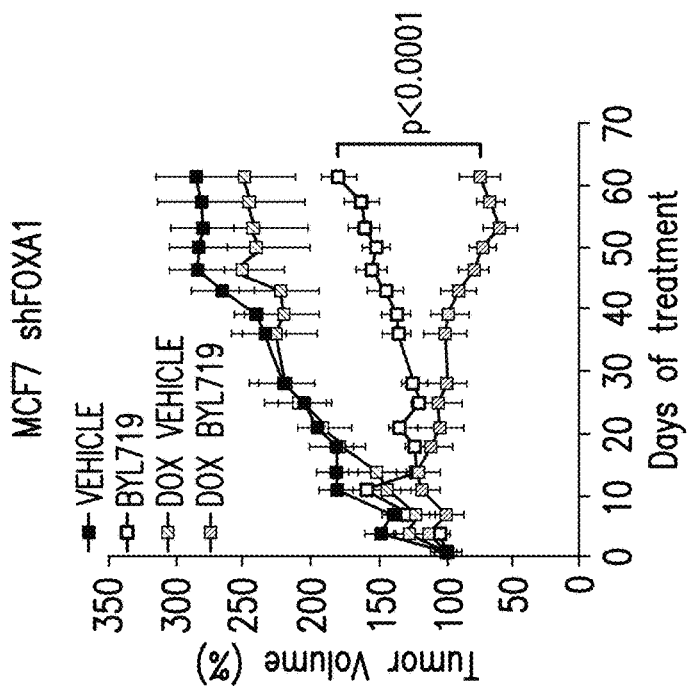
Figure 8H:
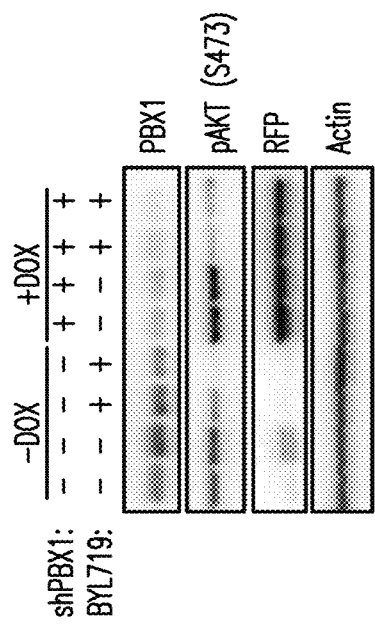
Figure 8G:
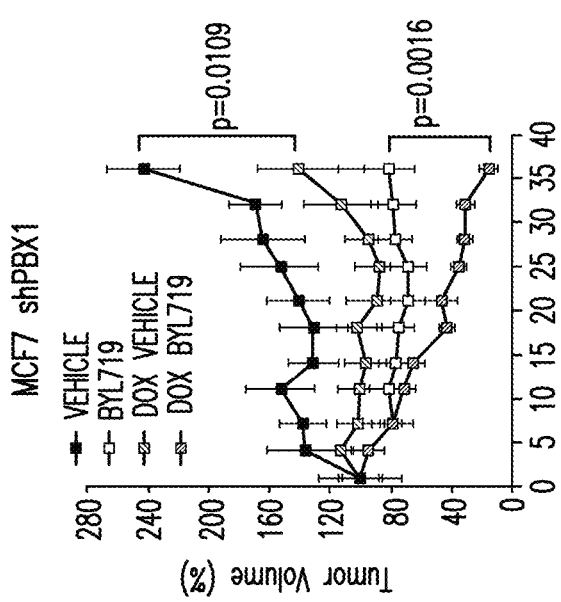
Figure 8I:
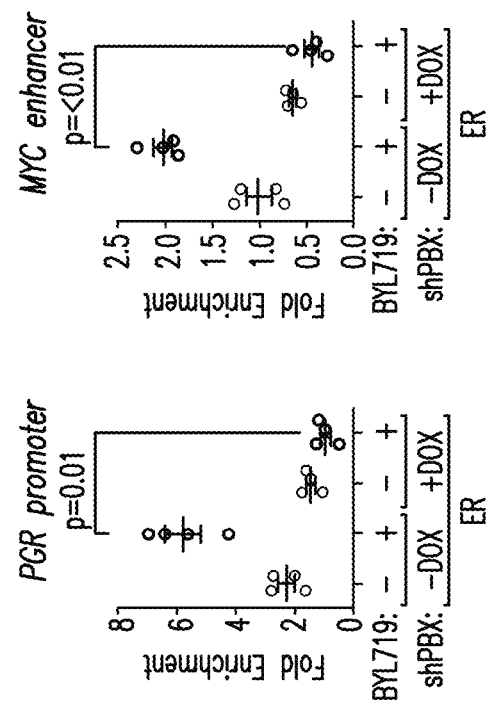

Given the requirement of FOXA1 and PBX1 to enhance ER function as a response to PI3K blockade, the role of these TFs on the pharmacologic response to PI3Kα inhibitors were determined. FOXA1 and PBX1 silencing by either constitutive or inducible shRNAs were sufficient to decrease the viability of cells treated with BYL719 (FIG. 8A-F). Next, the in vivo activity of BYL719 in MCF7 xenografts expressing inducible shRNA against FOXA1 was tested. While FOXA1 silencing alone had no discernible effects in tumor growth, it markedly increased the anti-tumor activity of BYL719 (FIG. 1F, G). Consistently, similar results were observed when PBX1 was knocked down in MCF7 xenografts (FIG. 8G, H). In these tumors, the reduction of ER occupancy when either FOXA1 or PBX1 were silenced was confirmed (FIG. 1H and FIG. 8I). These data indicate that FOXA1 or PBX1 silencing sensitizes cells to PI3Kα inhibition via suppression of ER activity.

Figure 8J:
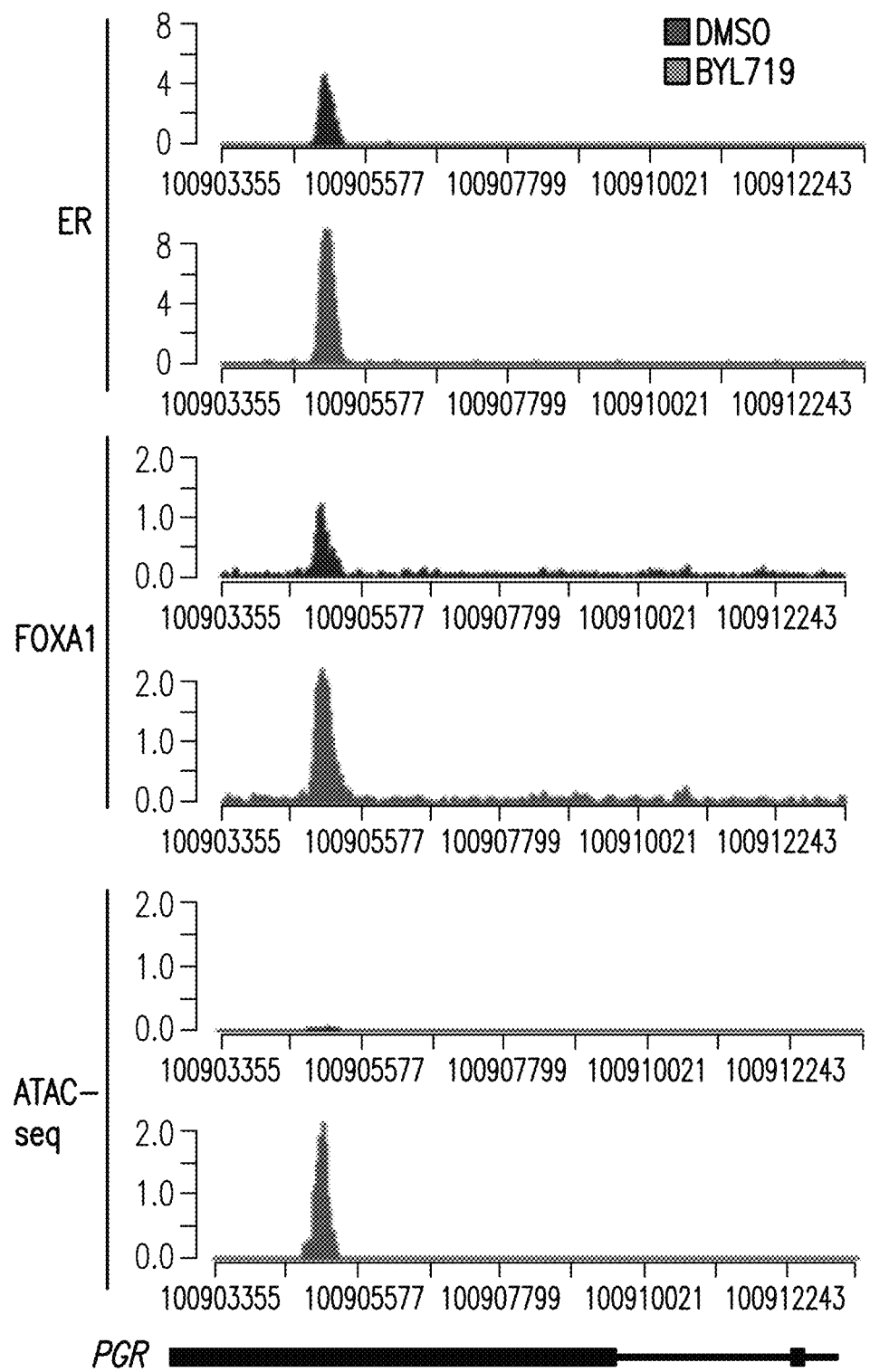

PI3K inhibition actively mediates a chromatin competent state at ER target loci. In order to gain insights into the overall impact that PI3K inhibition plays on regulating global chromatin structure of the breast cancer epigenome, assays for transposase-accessible chromatin using sequencing (ATAC-seq) were performed that enabled the study of chromatin openness and the interplay between TFs and chromatin accessible regions. Genome-wide ATAC-seq assays revealed that PI3Kα inhibition induces substantial changes in chromatin state, as demonstrated by an increase in the gained and lost chromatin accessible sites (FIG. 2A). Analysing the open chromatin patterns (FIG. 2B), a feature of active transcription, motif analysis inferred enriched responsive elements for ER, FOXA1 and PBX1 (FIG. 2C). In fact, ATAC-seq signals peaked at the same regions where ER and FOXA1 binding events were found by ChIP-seq, namely ER canonical target genes (FIG. 8J).

Figure 2D:
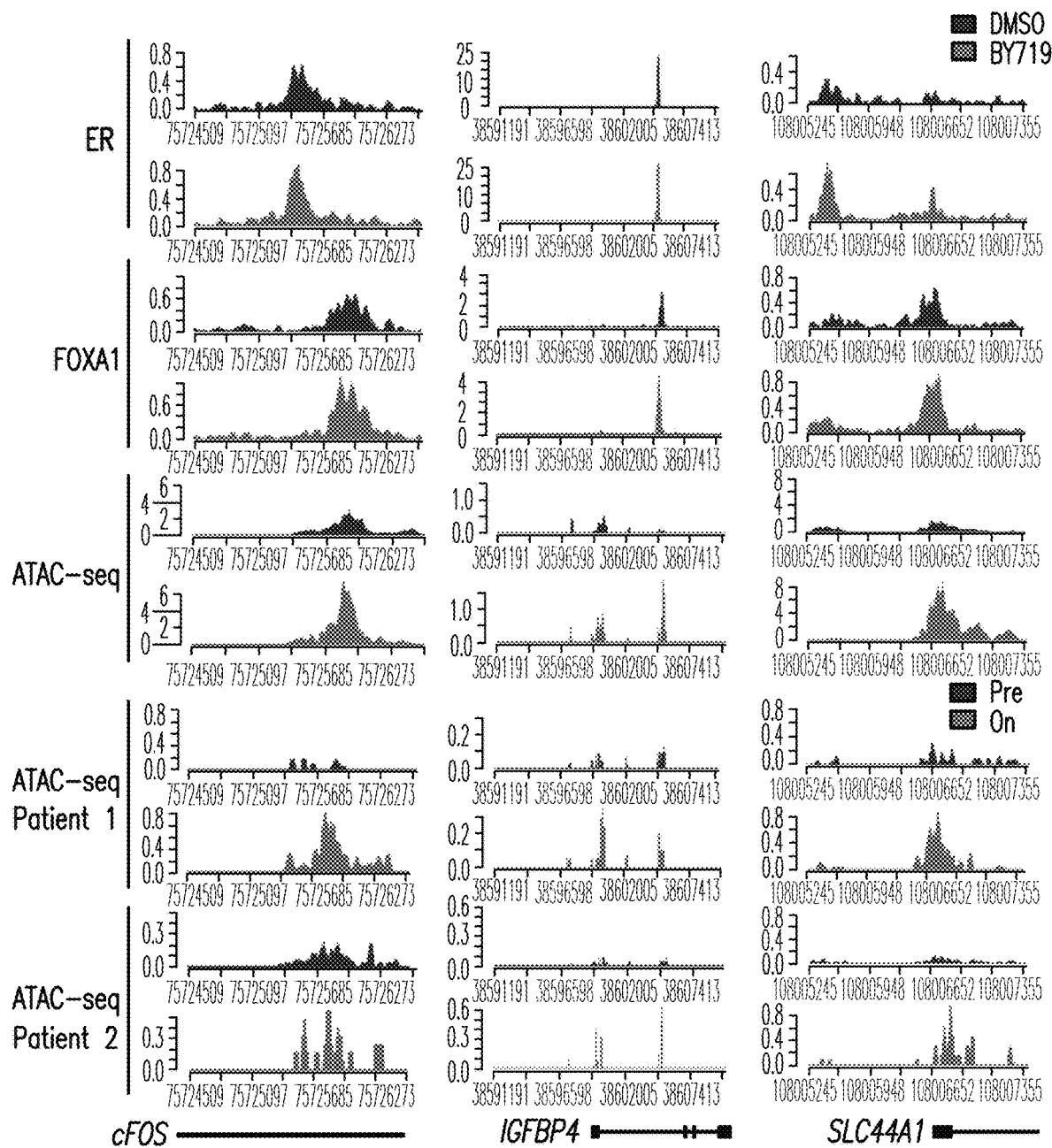

Taking advantage from the feasibility of performing ATAC-seq with limited number of cells[21], the epigenetic landscape of breast tumor samples from patients that had participated in the initial clinical trial with BYL719 were explored[8]. In paired tumor biopsies obtained prior to therapy and on-therapy, treatment with BYL719 was observed to induce an increase in chromatin accessibility in the regions previously identified to be responsive to PI3K inhibition (FIG. 2D). The ATAC-seq footprints of patients' samples peaked at the same genomic regions that showed increase binding of ER, FOXA1 and chromatin accessibility in our cell line model. Moreover, similar to the in vitro data, responsive elements for ER, FOXA1 and PBX1 were present in the open chromatin regions after in silico motif analysis, highlighting the specificity of our assay in clinical breast tumor specimens (FIG. 2E). These data revealed that PI3K inhibition results in reprogramming of the chromatin landscape to enhance ER-dependent transcription in breast cancer cell lines and patient samples.

Figure 9C:
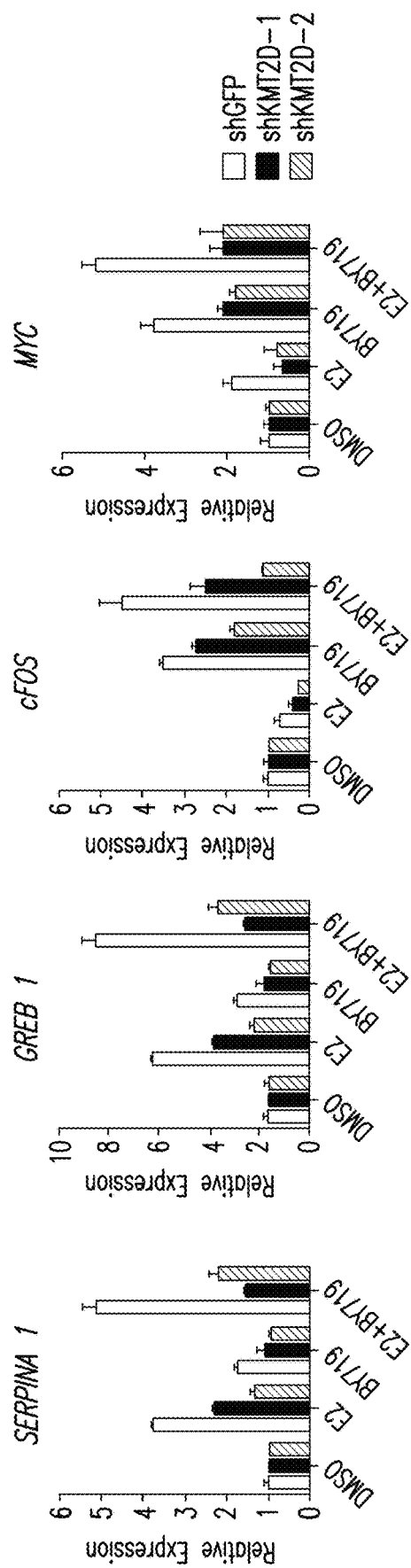
Figure 9D:
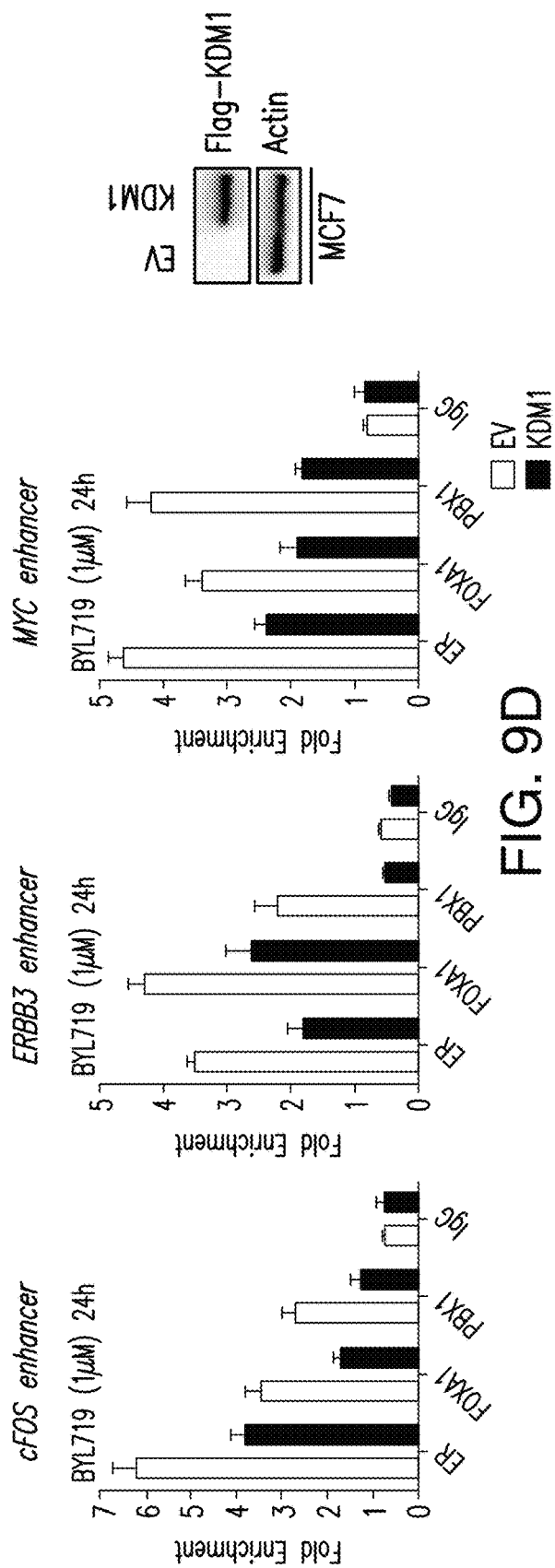

KMT2D orchestrates ER-dependent transcription upon PI3K inhibition. Since PI3K inhibition affects chromatin accessibility leading to a more ER-dependent transcription, in a FOXA1 and PBX1 dependent fashion, the chromatin regulators that might orchestrate this mechanism were investigated. It has been previously shown that active histone modifications, mono- and dimethylated H3K4 (H3K4me1/2), are associated with FOXA1 and PBX1 binding at both promoter and enhancer regions[19,22,23]. Additionally, KMT2D (also known as MLL2 or MLL4), a member of the COMPASS-like (Complex of Proteins Associated with Set1) family, is a major H3K4me1/2 methyltransferase that facilitates gene expression[24-27] and has the ability to interact with ER through LXXLL motifs[28]. Therefore, whether KMT2D played a role in the activation of the ER regulatory network after PI3Kα inhibition was explored. To this end, KMT2D was knocked down and ChIP-qPCR experiments were performed to examine the recruitment of ER, FOXA1 and PBX1. KMT2D knockdown resulted in a marked loss of binding of these TFs at shared target genes (FIG. 3A and FIG. 9A). KTM2D silencing also led to a significant decrease of H3K4me1/2 occupancy at representative ER canonical genes consistent with the notion that KMT2D is responsible for implementing these modifications in breast cancer cells (FIG. 9B). In the absence of KMT2D, a decrease of expression in ER-dependent genes were observed when cells were treated with BYL719 (FIG. 3B and FIG. 9C). Similarly, overexpression of the H3K4me1/2 demethylase KDM1[29], which antagonizes KMT2D enzymatic action, abrogated the occupancy of ER, FOXA1 and PBX1 and the expression of ER-dependent genes upon PI3Kα inhibition (FIG. 9D-F). Without being bound by a particular theory, these findings suggest that KMT2D is required for the activation of ER-dependent transcription upon PI3Kα blockage by implementing H3K4me1/2 modifications that guide FOXA1, PBX1 and ER recruitment to specific chromatin sites.

Figure 10A:
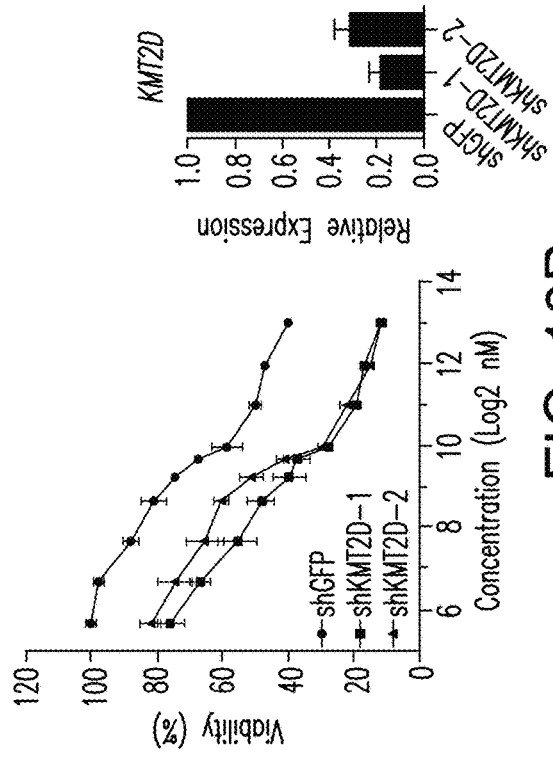
Figure 10B:
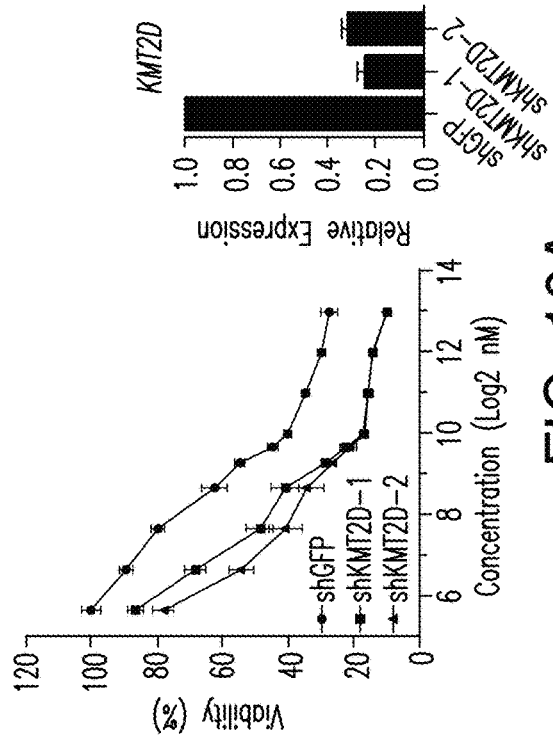
Figure 10C:
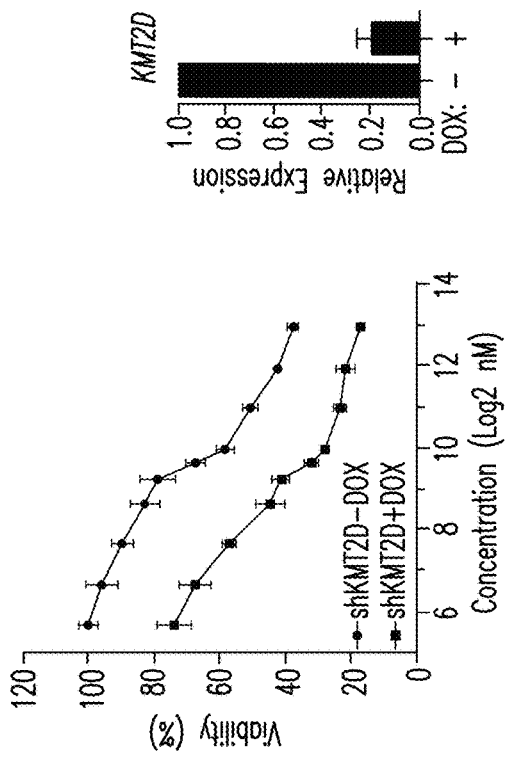

Since KMT2D silencing suppresses ER activation, it was hypothesized that loss of function of KMT2D might augment the therapeutic activity of BYL719 in ER-positive cells. Indeed, KMT2D knockdown was found to decrease cell viability in ER-positive cell lines and had a greater effect when combined with BYL719 (FIG. 10A-C). In xenografts, silencing KMT2D resulted in a marked antitumor effect that was enhanced in the presence of the PI3Kα inhibitor BYL719 (FIG. 3C, D). By performing ChIP-qPCR experiments in the in vivo tumor samples, a marked loss of binding of ER, FOXA1 and PBX1 when KMT2D was knocked down was confirmed (FIG. 3E). Hence, KMT2D silencing substantially augmented BYL719 anti-tumor effects by suppressing the binding of ER-FOXA1-PBX1 transcriptional regulatory network. These findings suggest that targeting KMT2D in ER-positive breast cancers could be a potential therapeutic strategy to enhance the sensitivity of PI3Kα inhibitors.

Figure 3F:
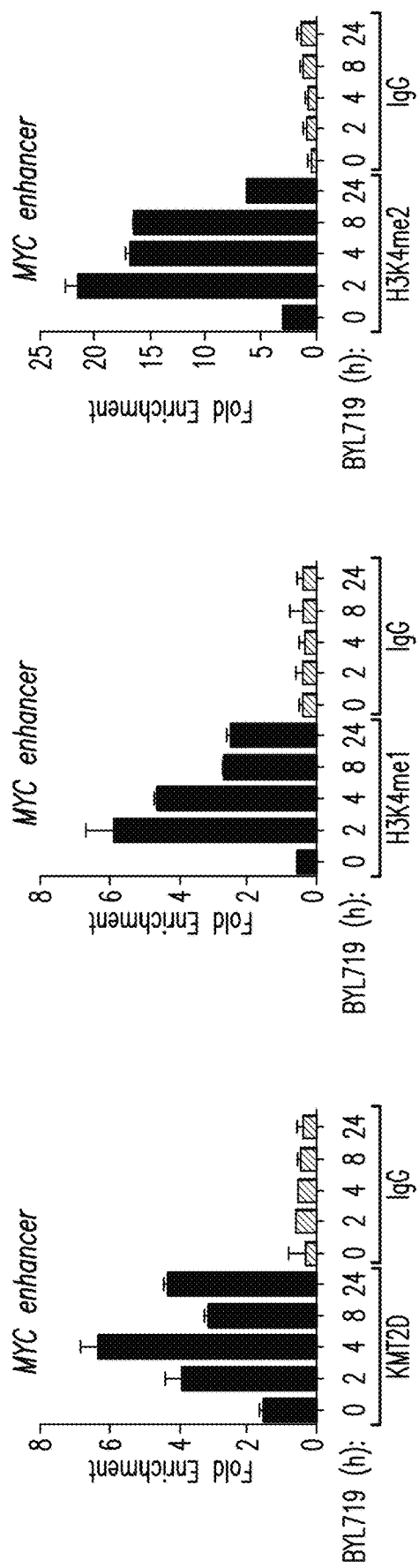
Figure 3G:
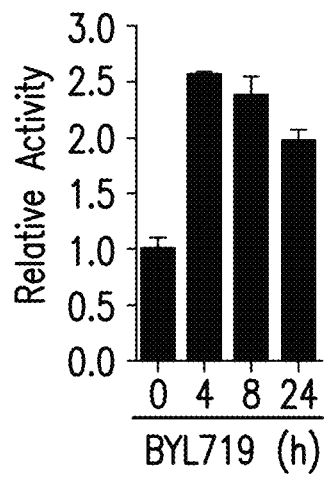
Figure 3H:
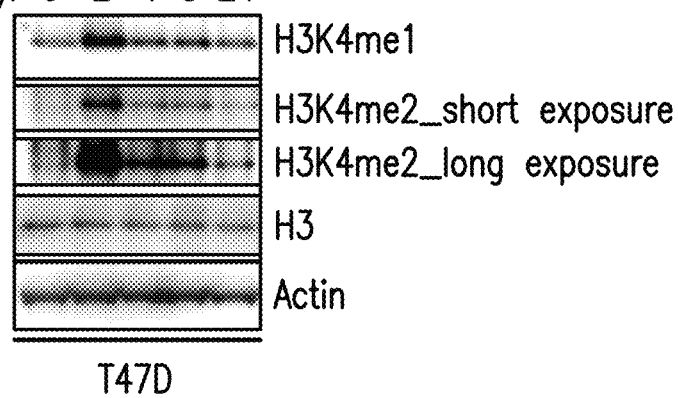
Figure 10D:
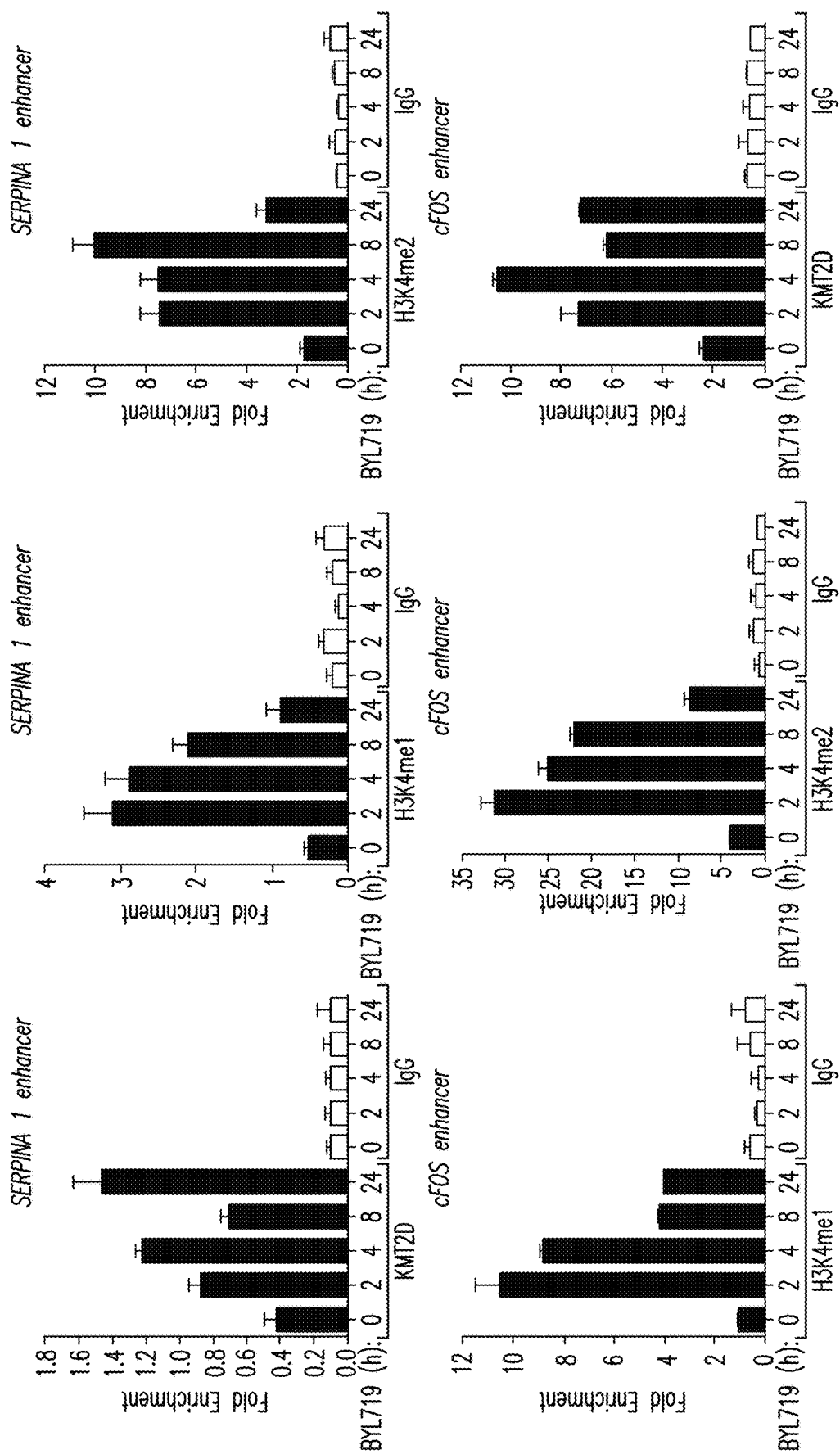
Figure 111:
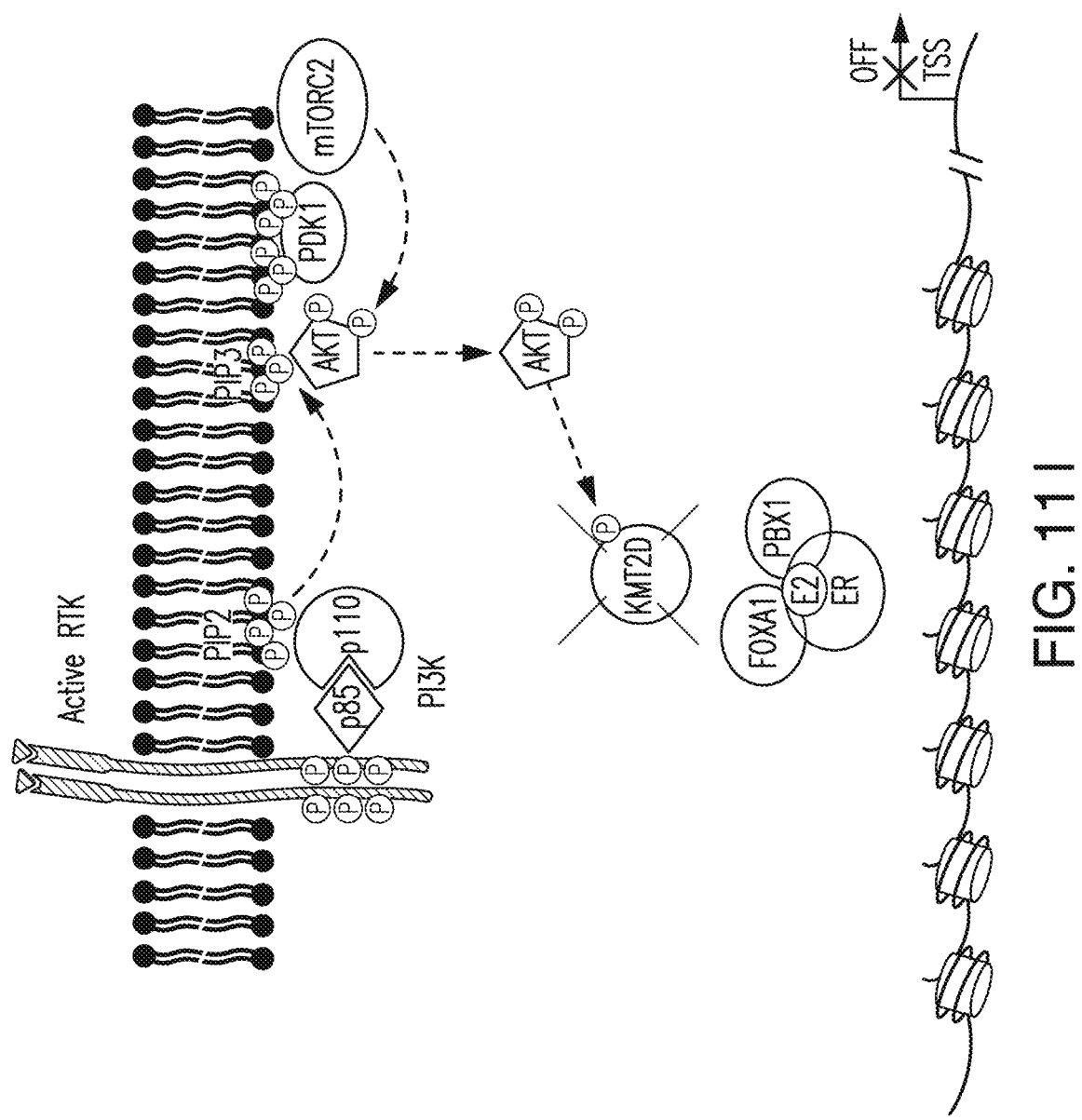

The findings that KMT2D is a determinant of ER function upon PI3Kα targeting, prompted the study of the mechanism by which PI3K inhibition is affecting the binding dynamics of KMT2D at the chromatin level. It was found that KMT2D recruitment at regulatory regions peaked at early hours of BYL719 treatment (FIG. 3F and FIG. 10D). The abundance of H3K4me1/2 occupying these regions were also elevated at the same time points, in agreement with total H3K4 methyltransferase activity and H3K4me1/2 protein levels (FIG. 3G-H and FIG. 10D). The tight temporal correlation between PI3Kα inhibition and changes in KMT2D recruitment, H3K4 methyltransferase activity and abundance of H3K4me1/2 suggested a direct regulation of KMT2D activity by the PI3K pathway.

Figure 4F:
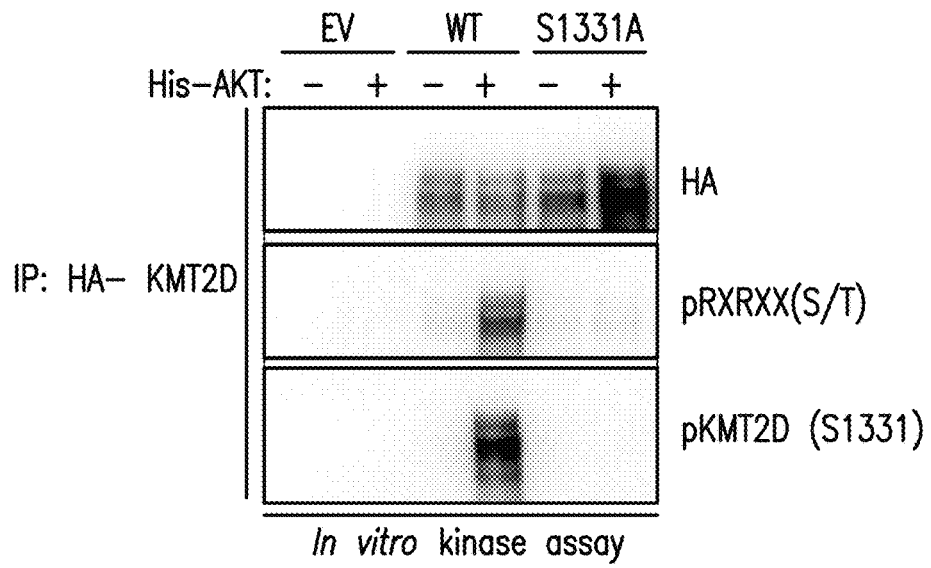
Figure 4G:
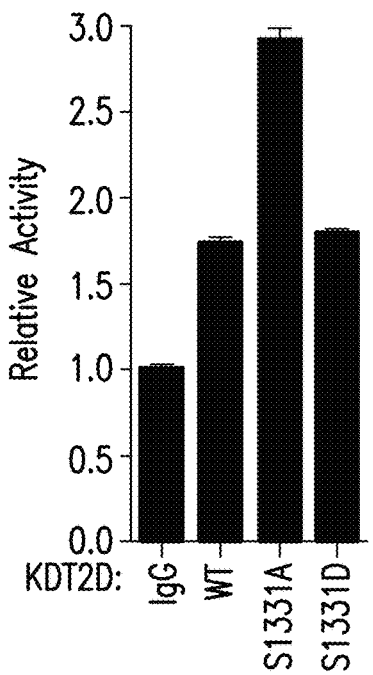
Figure 4H:
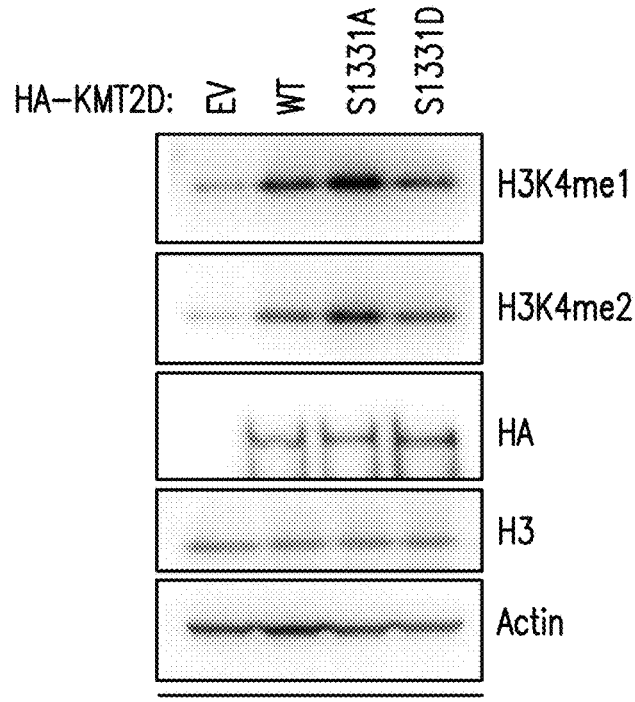

AKT interacts with and phosphorylates KMT2D. Oncogenic PI3K signaling regulates several downstream effectors through kinases that have the ability to phosphorylate and regulate their activity. Among these kinases, the Ser/Thr kinase AKT phosphorylates a large number of substrates by recognizing the consensus motif RXRXX(S/T)[30]. It was noticed that KMT2D protein sequence contains two RXRXX(S/T) consensus sites that are evolutionary conserved (FIG. 4A). While the consensus site at S1762 could not be detected by mass spectrometry (MS) due to the surrounding lysine-rich region, which renders it sensitive to trypsin digestion, the site at S1331 was found to be phosphorylated by MS (FIG. 11A, B). Co-immunoprecipitation assays of recombinant HA-tagged KMT2D and V5-tagged AKT1 revealed that KMT2D physically interacts with AKT1 (FIG. 4B). This interaction was also shown when endogenous KMT2D was immunoprecipitated and probed with AKT antibodies (FIG. 4C). To further identify the interacting region between KMT2D and AKT and given the large size of KMT2D (~553 kDa), co-immunoprecipitation assays using five non-overlapping fragments of KMT2D were performed (FIG. 4D), which demonstrated that AKT binds the 1222-1819 region of KMT2D, where the S1331 phosphorylation site is present (FIG. 4E). To test the ability of AKT to directly phosphorylate S1331, in vitro kinase assays using recombinant active AKT and KMT2D as a substrate were performed. The kinase assay confirmed the ability of AKT to directly phosphorylate S1331, as detected by the phospho-RXRXX(S/T) and phospho-KMT2D (S1331) antibodies (FIG. 4F and FIG. 11C). Mutation of serine to alanine (S1331A) completely abrogated the ability of AKT to phosphorylate KMT2D in vitro (FIG. 4F and FIG. 11C). Endogenously, KMT2D was found to be more phosphorylated at S1331 in isogenic PIK3CA H1047R cells as compared to WT cells and treatment with either PI3K or AKT inhibitors in ER-positive cell lines reduced S1331 phosphorylation (FIG. 11D-F). Next, how phosphorylation of KMT2D by AKT affects KMT2D activity was determined. Mutation of KMT2D S1331 to the non-phosphorylatable amino acid alanine (S1331A) increased H3K4 methyltransferase activity and the levels of H3K4me1/2. Conversely, mutation of this site to the phosphomimetic amino acid aspartic acid (S1331D) decreased the levels of KMT2D activity (FIG. 4G, H), suggesting that the functional role of this phosphorylation is the suppression of KMT2D methyltransferase activity. These data suggest that the PI3K pathway and its direct effector AKT inhibits KMT2D activity through a direct phosphorylation event.

In summary, these findings indicate that ER-dependent transcription is tightly regulated by the PI3K signaling pathway via KMT2D. In scenarios where PI3K signaling is active, such as tumors with oncogenic PIK3CA mutations, AKT phosphorylates KMT2D at S1331. KMT2D phosphorylation decreases its methyltransferase activity, causing the reduction of H3K4me1/2 and subsequent decreased binding of the FOXA1-PBX1-ER transcriptional network, leading to the transcriptional suppression of ER target genes. Conversely, inhibition of the PI3K/AKT pathway would increase KMT2D activity and H3K4me1/2 methylation that facilitates the recruitment of FOXA1-PBX1 regulatory network to allow successive binding of ER, unleashing a robust ER-dependent transcriptional program (FIG. 11G). Thus, these data support a role for KMT2D in modulating the chromatin competence necessary for the assembly of the ER-FOXA1-PBX1 transcriptional regulatory network, causing a dominant impact on transcription output that leads to therapeutic resistance to PI3K inhibitors. Moreover, without being limited to a particular theory, it appears that phosphorylated KMT2D may function as a biomarker of resistance to therapeutic agents targeting PI3K/AKT in the context of hormone-dependent malignancies. These findings delineate the epigenetic mechanisms of ER activation by the PI3K pathway and directly connect an oncogenic signaling pathway with chromatin-based control of gene expression. In agreement with other studies in which AKT has been shown to regulate the function of the chromatin remodelers EZH2[31] and KDM5A[32], these findings also highlight the importance of investigating the less well-understood mechanisms by which protein kinase activation controls the cancer epigenome. Therapeutically, the discovery of the specific role of KMT2D in the interplay between ER and PI3K signaling provides a rationale for epigenetically informed combination therapies with PI3K inhibitors in ER-positive breast cancer, perhaps with novel small molecules targeting KMT2D.

6.3 References

1. Engelman, J. A. Targeting PI3K signaling in cancer: opportunities, challenges and limitations. *Nature reviews. Cancer* 9, 550-562, doi:10.1038/nrc2664 (2009).
2. Cantley, L. C. The phosphoinositide 3-kinase pathway. *Science* 296, 1655-1657, doi:10.1126/science.296.5573.1655 (2002).
3. Thorpe, L. M. et al. PI3K in cancer: divergent roles of isoforms, modes of activation and therapeutic targeting. *Nature reviews. Cancer* 15, 7-24, doi:10.1038/nrc3860 (2015).
4. Manning, B. D. & Cantley, L. C. AKT/PKB signaling: navigating downstream. *Cell* 129, 1261-1274, doi:10.1016/j.cell.2007.06.009 (2007).
5. Cancer Genome Atlas, N. Comprehensive molecular portraits of human breast tumors. *Nature* 490, 61-70, doi:10.1038/nature 11412 (2012).
6. Ciriello, G. et al. Comprehensive Molecular Portraits of Invasive Lobular Breast Cancer. *Cell* 163, 506-519, doi: 10.1016/j.cell.2015.09.033 (2015).
7. Juric, D. et al. GDC-0032, a beta isoform-sparing PI3K inhibitor: Results of a first-in-human phase Ia dose escalation study. *Cancer research* 73, LB-64-LB-64 (2013).
8. Juric, D. et al. BYL719, a next generation PI3K alpha specific inhibitor: Preliminary safety, PK, and efficacy results from the first-in-human study. *Cancer research* 72, CT-01-CT-01 (2012).
9. Costa, C. et al. Measurement of PIP3 levels reveals an unexpected role for p110beta in early adaptive responses to p110alpha-specific inhibitors in luminal breast cancer. *Cancer cell* 27, 97-108, doi:10.1016/j.ccell.2014.11.007 (2015).
10. Juric, D. et al. Convergent loss of PTEN leads to clinical resistance to a PI3Kalpha inhibitor. *Nature* 518, 240-244, doi:10.1038/naturel3948 (2015).
11. Bosch, A. et al. PI3K inhibition results in enhanced estrogen receptor function and dependence in hormone receptor-positive breast cancer. *Science translational medicine* 7, 283ra251, doi:10.1126/scitranslmed.aaa4442 (2015).
12. Janku, F. et al. Phase I study of the PI3Kα inhibitor BYL719 plus fulvestrant in patients with PIK3CA-altered and wild type ER+/HER2− locally advanced or metastatic breast cancer. *Cancer research* 75, PD5-5-PD5-5, doi: 10.1158/1538-7445.sabcs14-pd5-5 (2015).
13. Mayer, I. A. et al. A Phase Ib Study of Alpelisib (BYL719), a PI3Kalpha-specific Inhibitor, with Letrozole in ER+/HER2−Negative Metastatic Breast Cancer. *Clinical cancer research: an official journal of the American Association for Cancer Research*, doi:10.1158/1078-0432.CCR-16-0134 (2016).
14. Juric, D. et al. Ph1b study of the PI3K inhibitor GDC-0032 in combination with fulvestrant in patients with hormone receptor-positive advanced breast cancer. *Cancer research* 73, doi:10.1158/0008-5472. SABCS13-PD1-3 (2013).
15. Baselga, J. et al. SANDPIPER: Phase III study of the PI3-kinase (PI3K) inhibitor taselisib (GDC-0032) plus fulvestrant in patients (pts) with estrogen receptor (ER)-positive, HER2-negative locally advanced or metastatic breast cancer (BC) enriched for pts with PIK3CA-mutant tumors. *J Clin Oncol* 34 (2016).
16. Andre, F. et al. SOLAR-1: A phase III study of alpelisib+fulvestrant in men and postmenopausal women with HR+/HER2− advanced breast cancer (BC) progressing on or after prior aromatase inhibitor therapy. *J Clin Oncol* 34 (2016).
17. Green, K. A. & Carroll, J. S. Oestrogen-receptor-mediated transcription and the influence of co-factors and chromatin state. *Nature reviews. Cancer* 7, 713-722, doi:10.1038/nrc2211 (2007).
18. Hurtado, A. et al. FOXA1 is a key determinant of estrogen receptor function and endocrine response. *Nature genetics* 43, 27-33, doi:10.1038/ng.730 (2011).
19. Magnani, L. et al. PBX1 genomic pioneer function drives ERalpha signaling underlying progression in breast cancer. *PLoS genetics* 7, e1002368, doi:10.1371/journal.pgen.1002368 (2011).
20. Fritsch, C. et al. Characterization of the novel and specific PI3Kalpha inhibitor NVP-BYL719 and development of the patient stratification strategy for clinical trials. *Molecular cancer therapeutics* 13, 1117-1129, doi: 10.1158/1535-7163.MCT-13-0865 (2014).
21. Buenrostro, J. D. et al. Transposition of native chromatin for fast and sensitive epigenomic profiling of open chromatin, DNA-binding proteins and nucleosome position. *Nature methods* 10, 1213-1218, doi:10.1038/nmeth.2688 (2013).
22. Eeckhoute, J. et al. Cell-type selective chromatin remodeling defines the active subset of FOXA1-bound enhancers. *Genome research* 19, 372-380, doi:10.1101/gr.084582.108 (2009).

23. Lupien, M. et al. FoxA1 translates epigenetic signatures into enhancer-driven lineage-specific transcription. *Cell* 132, 958-970, doi:10.1016/j.cell.2008.01.018 (2008).
24. Herz, H. et al. Enhancer malfunction in cancer. *Molecular cell* 53, 859-866, doi:10.1016/j.molcel.2014.02.033 (2014).
25. Herz, H. M. et al. Enhancer-associated H3K4 monomethylation by Trithorax-related, the *Drosophila* homolog of mammalian M113/M114. *Genes & development* 26, 2604-2620, doi:10.1101/gad.201327.112 (2012).
26. Hu, D. et al. The MLL3/MLL4 branches of the COMPASS family function as major histone H3K4 monomethylases at enhancers. *Molecular and cellular biology* 33, 4745-4754, doi:10.1128/MCB.01181-13 (2013).
27. Shilatifard, A. The COMPASS family of histone H3K4 methylases: mechanisms of regulation in development and disease pathogenesis. *Annual review of biochemistry* 81, 65-95, doi:10.1146/annurev-biochem-051710-134100 (2012).
28. Mo, R. et al. Identification of the MLL2 complex as a coactivator for estrogen receptor alpha. *The Journal of biological chemistry* 281, 15714-15720, doi:10.1074/jbc.M513245200 (2006).
29. Kooistra, S. M. & Helin, K. Molecular mechanisms and potential functions of histone demethylases. *Nature reviews. Molecular cell biology* 13, 297-311, doi:10.1038/nrm3327 (2012).
30. Pearce, L. R. et al. The nuts and bolts of AGC protein kinases. *Nature reviews. Molecular cell biology* 11, 9-22, doi:10.1038/nrm2822 (2010).
31. Cha, T. L. et al. Akt-mediated phosphorylation of EZH2 suppresses methylation of lysine 27 in histone H3. *Science* 310, 306-310, doi:10.1126/science. 1118947 (2005).
32. Spangle, J. M. et al. PI3K/AKT Signaling Regulates H3K4 Methylation in Breast Cancer. *Cell reports* 15, 2692-2704, doi:10.1016/j.celrep.2016.05.046 (2016).
33. Erdjument-Bromage, H. et al. Examination of micro-tip reversed-phase liquid chromatographic extraction of peptide pools for mass spectrometric analysis. *Journal of chromatography. A* 826, 167-181 (1998).
34. Bolger, A. M. et al. Trimmomatic: a flexible trimmer for Illumina sequence data. *Bioinformatics* 30, 2114-2120, doi:10.1093/bioinformatics/btu170 (2014).
35. Langmead, B. et al. Ultrafast and memory-efficient alignment of short DNA sequences to the human genome. *Genome Biol* 10, R25, doi:10.1186/gb-2009-10-3-r25 (2009).
36. Zhang, Y. et al. Model-based analysis of ChIP-Seq (MACS). *Genome Biol* 9, R137, doi:10.1186/gb-2008-9-9-r137 (2008).
37. Li, Q. et al. Measuring reproducibility of high-thoughput experiments. *The Annals of Applied Statistics* 5, 1752-1779 (2011).
38. Robinson, M. D. et al. edgeR: a Bioconductor package for differential expression analysis of digital gene expression data. *Bioinformatics* 26, 139-140, doi:10.1093/bioinformatics/btp616 (2010).
39. Zhu, L. J. et al. ChIPpeakAnno: a Bioconductor package to annotate ChIP-seq and ChIP-chip data. *BMC Bioinformatics* 11, 237, doi:10.1186/1471-2105-11-237 (2010).
40. Heinz, S. et al. Simple combinations of lineage-determining transcription factors prime cis-regulatory elements required for macrophage and B cell identities. *Mol Cell* 38, 576-589, doi:10.1016/j.molcel.2010.05.004 (2010).
41. Gentleman, R. C. et al. Bioconductor: open software development for computational biology and bioinformatics. *Genome Biol* 5, R80, doi:10.1186/gb-2004-5-10-r80 (2004).
42. Ramirez, F. et al. deepTools: a flexible platform for exploring deep-sequencing data. *Nucleic Acids Res* 42, W187-191, doi:10.1093/nar/gku365 (2014).

Various references are cited herein, the contents of which are hereby incorporated by reference in their entireties herein. Various nucleic acid and amino acid sequence accession numbers are cited herein, and the complete sequences referenced by those accession numbers are hereby incorporated by reference in their entireties herein.

What is claimed is:

1. A method for treating a subject having a cancer comprising administering, to the subject, a therapeutically effective amount of a KMT2D inhibitor and a therapeutically effective amount of a PI3Kα inhibitor.

2. The method of claim 1, wherein the cancer is breast cancer.

3. The method of claim 1, wherein the PI3Kα inhibitor is BYL719.

4. A method of reducing or inhibiting the growth or proliferation rate of a cancer cell comprising administering to the cancer cell or contacting the cancer cell with a therapeutically effective amount of a KMT2D inhibitor and a therapeutically effective amount of a PI3Kα inhibitor.

5. The method of claim 4, wherein the cancer cell is a breast cancer cell.

6. The method of claim 4, wherein the PI3Kα inhibitor is BYL719.

7. The method of claim 2, wherein the breast cancer is an ER-positive breast cancer.

8. The method of claim 5, wherein the breast cancer cell is an ER-positive breast cancer cell.

* * * * *

SEQUENCE LISTING

```
<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtggtagccg agtggacaat                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atttgtttcc agccctcctt                                                  20
```

```
<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcatggtcc ttggaggt                                                       18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccactggctg tgggagag                                                       18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgatgacctg ggcttcccag                                                     20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caaagggctc ggtcttcagc                                                     20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggagcaaatg aaatgttggt g                                                   21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggaaaacct atggggaatg                                                     20

<210> SEQ ID NO 9
```

<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgatcaccg gcctcaat                                              18

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggaagacatt gagcttctct gg                                         22

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatggggctg acctctcc                                              18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtcagcacag ccttatgcac                                            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctgcttaga cgctggattt                                            20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taacgttgag gggcatcg                                              18

<210> SEQ ID NO 15
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgtcttcccc tccatcgt                                                    18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaaggtgtgg tgccagattt                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acagtcagcc gcatcttctt                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgaccaaat ccgttgactc                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaagggcaga gctgataacg                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gacccagttg ccacactttt                                                  20

<210> SEQ ID NO 21
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 21
agggaggaga aagtgggtgt                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggagaactcc ccgagttagg                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgatgacctg ggcttcccag                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgatgacctg ggcttcccag                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acctccaaga gggagaggag                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggaccaagca gtcatttggt                                                   20

<210> SEQ ID NO 27
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 27
aggtatgggc acaagacctg                                                     20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcaggggaaa attgtcttcg                                                     20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtcagccaat cttcgcactt                                                     20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgccagagga agctactggt                                                     20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgttccaggc tctgttcctc                                                     20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32 agaaagaac gcaggcagaa                                                      20

<210> SEQ ID NO 33
<211> LENGTH: 57
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 33
ccggcctcgc ctcaagaaat ggaaactcga gtttccattt cttgaggcga ggttttt    57

<210> SEQ ID NO 34
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccggcctgaa ttgaacaaca gtcttctcga gaagactgtt gttcaattca ggttttt    57

<210> SEQ ID NO 35
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccggcccacc tgaatcatca cctttctcga gaaaggtgat gattcaggtg ggttttt    57

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Ala Arg Leu Lys Ser Thr Ala Ser Ser Ile Cys
1               5                   10

<210> SEQ ID NO 37
<211> LENGTH: 8
<212> TYPE: PRT
<213> ORGANISM: Homo sapiens

<400> SEQUENCE: 37

Gly Arg Ala Arg Leu Lys Ser Thr
1               5

<210> SEQ ID NO 38
<211> LENGTH: 8
<212> TYPE: PRT
<213> ORGANISM: Homo sapiens

<400> SEQUENCE: 38

Arg Arg Gly Arg Lys Lys Ser Lys
1               5

<210> SEQ ID NO 39
<211> LENGTH: 8
<212> TYPE: PRT
<213> ORGANISM: Pan troglodytes

<400> SEQUENCE: 39

Gly Arg Ala Arg Leu Lys Ser Thr
1               5

<210> SEQ ID NO 40
<211> LENGTH: 8
<212> TYPE: PRT
<213> ORGANISM: Pan troglodytes

<400> SEQUENCE: 40

Arg Arg Gly Arg Lys Lys Ser Lys
1               5

<210> SEQ ID NO 41
<211> LENGTH: 8
<212> TYPE: PRT
<213> ORGANISM: Mus musculus

<400> SEQUENCE: 41

Gly Arg Ala Arg Leu Lys Ser Thr
1               5

<210> SEQ ID NO 42
<211> LENGTH: 8
<212> TYPE: PRT
<213> ORGANISM: Mus musculus

<400> SEQUENCE: 42

Arg Arg Ala Arg Lys Lys Ser Lys
1               5

<210> SEQ ID NO 43
<211> LENGTH: 8
<212> TYPE: PRT
<213> ORGANISM: Xenopus laevis

<400> SEQUENCE: 43

Gly Arg Ser Arg Leu Lys Ser Thr
1               5

<210> SEQ ID NO 44
<211> LENGTH: 8
<212> TYPE: PRT
<213> ORGANISM: Xenopus laevis

<400> SEQUENCE: 44

Arg Arg Gly Arg Lys Lys Ser Lys
1               5

<210> SEQ ID NO 45
<211> LENGTH: 8
<212> TYPE: PRT
<213> ORGANISM: Danio rerio

<400> SEQUENCE: 45

Gly Arg Gly Arg Gly Arg Ser Arg
1               5

<210> SEQ ID NO 46
<211> LENGTH: 8
<212> TYPE: PRT
<213> ORGANISM: Danio rerio

<400> SEQUENCE: 46

Arg Arg Gly Arg Lys Lys Ser Lys
1               5